US012686722B2

(12) United States Patent

Greenberg et al.

(10) Patent No.: US 12,686,722 B2

(45) Date of Patent: Jul. 21, 2026

(54) ANTI-HVEM ANTIBODIES AND USE THEREOF

(71) Applicants: 4C BIOMED LIMITED, London (GB); TEL HASHOMER MEDICAL RESEARCH INFRASTRUCTURE AND SERVICES LTD., Ramat Gan (IL)

(72) Inventors: Eyal Greenberg, Even Yehuda (IL); Gilli Galore-Haskel, Tel Mond (IL); Efrat Merhavi-Shoham, Rehovot (IL); Gal Markel, Ramat Gan (IL); Jacob Schachter, Givatayim (IL)

(73) Assignees: 4C BIOMED LIMITED, London (GB); TEL HASHOMER MEDICAL RESEARCH INFRASTRUCTURE AND SERVICES LTD., Ramat Gan (IL)

( * ) Notice: Subject to any disclaimer, the term of this patent is extended or adjusted under 35 U.S.C. 154(b) by 1056 days.

(21) Appl. No.: 17/607,189

(22) PCT Filed: Apr. 28, 2020

(86) PCT No.: PCT/IL2020/050479

§ 371 (c)(1),
(2) Date: Oct. 28, 2021

(87) PCT Pub. No.: WO2020/222235

PCT Pub. Date: Nov. 5, 2020

(65) Prior Publication Data

US 2022/0227879 A1 Jul. 21, 2022

Related U.S. Application Data

(60) Provisional application No. 62/965,921, filed on Jan. 26, 2020, provisional application No. 62/839,841, filed on Apr. 29, 2019.

(51) Int. Cl.

| | |
|---|---|
| *C07K 16/28* | (2006.01) |
| *A61K 39/395* | (2006.01) |
| *A61K 45/06* | (2006.01) |
| *A61P 35/00* | (2006.01) |
| *G01N 33/575* | (2026.01) |
| *A61K 39/00* | (2006.01) |

(52) U.S. Cl.

CPC ...... *C07K 16/2878* (2013.01); *A61K 39/3955* (2013.01); *A61K 45/06* (2013.01); *A61P 35/00* (2018.01); *G01N 33/5759* (2026.01); *A61K 2039/505* (2013.01); *C07K 2317/565* (2013.01); *C07K 2317/622* (2013.01); *C07K 2317/76* (2013.01); *G01N 2333/70578* (2013.01)

(58) Field of Classification Search

CPC .......... C07K 16/2878; C07K 2317/565; C07K 2317/622; C07K 2317/76; C07K 2317/33; C07K 2317/52; C07K 16/30; C07K 16/3053; C07K 2317/73; C07K 2317/74; C07K 16/2818; A61K 39/3955; A61K 45/06; A61K 2039/505; A61K 2039/507; A61P 35/00; A61P 31/00; G01N 33/57492; G01N 2333/70578; G01N 33/6872; G01N 2800/52

See application file for complete search history.

(56) References Cited

U.S. PATENT DOCUMENTS

| | | | |
|---|---|---|---|
| 8,318,166 B2 | 11/2012 | Olive et al. | |
| 2016/0090420 A1 | 3/2016 | Olive et al. | |
| 2016/0122434 A1* | 5/2016 | Olive ...................... | A61P 15/00 |
| | | | 424/143.1 |
| 2018/0055882 A1 | 3/2018 | Rosenblum et al. | |

FOREIGN PATENT DOCUMENTS

| | | | |
|---|---|---|---|
| JP | 2015-517470 A | 6/2015 | |
| JP | 2016518436 A | 6/2016 | |
| JP | 2017-534247 A | 11/2017 | |
| WO | 2014184360 A1 | 11/2014 | |
| WO | 2018/129332 A1 | 7/2018 | |
| WO | 2020/072705 A1 | 4/2020 | |
| WO | 2020/222235 A1 | 11/2020 | |
| WO | 2022/074648 A1 | 4/2022 | |

OTHER PUBLICATIONS

Pasero C, Speiser DE, Derré L, Olive D. The HVEM network: new directions in targeting novel costimulatory/co-inhibitory molecules for cancer therapy. Curr Opin Pharmacol. Aug. 2012;12(4):478-85. (Year: 2012).*

Gershoni et al. Epitope mapping: the first step in developing epitope-based vaccines. BioDrugs. 2007;21(3):145-56. (Year: 2007).*

Schreiber et al. 3D-Epitope-Explorer (3DEX): localization of conformational epitopes within three-dimensional structures of proteins. J Comput Chem. Jul. 15, 2005;26(9):879-87. (Year: 2005).*

Blythe et al. Benchmarking B cell epitope prediction: underperformance of existing methods. Protein Sci. Jan. 2005;14(1):246-8. (Year: 2005).*

Ladner RC. Mapping the epitopes of antibodies. Biotechnol Genet Eng Rev. 2007;24:1-30. (Year: 2007).*

Spodzieja et al. Design of short peptides to block BTLA/HVEM interactions for promoting anticancer T-cell responses. PLoS One. Jun. 8, 2017;12(6):e0179201. (Year: 2017).*

(Continued)

*Primary Examiner* — Julie Wu

*Assistant Examiner* — Amber K Faust

(74) *Attorney, Agent, or Firm* — The Roy Gross Law Firm, LLC; Roy D. Gross

(57) ABSTRACT

Agents that bind HVEM, inhibit HVEM-BTLA interaction and activate downstream HVEM signaling are provided. Methods of treating disease with those agents and kits comprising those agents are also provided.

14 Claims, 25 Drawing Sheets

Specification includes a Sequence Listing.

(56) References Cited

OTHER PUBLICATIONS

Fourcade et al. CD8(+) T cells specific for tumor antigens can be rendered dysfunctional by the tumor microenvironment through upregulation of the inhibitory receptors BTLA and PD-1. Cancer Res. Feb. 15, 2012;72(4):887-96. (Year: 2012).*

Moreno et al. Anti-PD-1 therapy in melanoma. Semin Oncol. Jun. 2015;42(3):466-73. (Year: 2015).*

Peretz et al. CD160 and PD-1 co-expression on HIV-specific CD8 T cells defines a subset with advanced dysfunction. PLoS Pathog. 2012;8(8):e1002840. (Year: 2012).*

Grabmeier-Pfistershammer et al Antibodies targeting BTLA or TIM-3 enhance HIV-1 specific T cell responses in combination with PD-1 blockade. Clin Immunol. Oct. 2017;183:167-173. (Year: 2017).*

Murphy TL, Murphy KM. Slow down and survive: Enigmatic immunoregulation by BTLA and HVEM. Annu Rev Immunol. 2010;28:389-411. (Year: 2010).*

Alsaab HO, Sau S, Alzhrani R, Tatiparti K, Bhise K, Kashaw SK, Iyer AK. PD-1 and PD-L1 Checkpoint Signaling Inhibition for Cancer Immunotherapy: Mechanism, Combinations, and Clinical Outcome. Front Pharmacol. Aug. 23, 2017;8:561. (Year: 2017).*

Stecher C, Battin C, Leitner J, Zettl M, Grabmeier-Pfistershammer K, Höller C, Zlabinger GJ, Steinberger P. PD-1 Blockade Promotes Emerging Checkpoint Inhibitors in Enhancing T Cell Responses to Allogeneic Dendritic Cells. Front Immunol. May 22, 2017;8:572. (Year: 2017).*

Ren S, Tian Q, Amar N, Yu H, Rivard CJ, Caldwell C, Ng TL, Tu M, Liu Y, Gao D, Ellison K, Suda K, Rozeboom L, Rivalland G, Mitchell P, Zhou C, Hirsch FR. The immune checkpoint, HVEM may contribute to immune escape in non-small cell lung cancer lacking PD-L1 expression. Lung Cancer. Nov. 2018;125:115-120. doi: 10.1016/j.lungcan.2018.09.004. Epub Sep. 12, 2018. PMID: 30429008.

Brunel, S., et al. "HVEM blockade initiates tumor cell death by innate immunity and improves anti-tumor response by human T cells in NSG immuno-compromised mice." bioRxiv (2019): 711119.

Khandelwal N, Breinig M, Speck T, Michels T, Kreutzer C, Sorrentino A, Sharma AK, Umansky L, Conrad H, Poschke I, Offringa R, König R, Bernhard H, Machlenkin A, Boutros M, Beckhove P. A high-throughput RNAi screen for detection of immune-checkpoint molecules that mediate tumor resistance to cytotoxic T lymphocytes. EMBO Mol Med. Apr. 2015;7(4):450-63. doi: 10.15252/emmm.201404414. PMID: 25691366; PMCID: PMC4403046.

International Search Report of PCT/IL2020/050479 Completed Jun. 25, 2020; Mailed Jun. 29, 2022 6 pages.

Written Opinion of PCT/IL2020/050479 Completed Jun. 25, 2020; Mailed Jun. 29, 2022 8 pages.

Cai, G. & Freeman, G. J. The CD160, BTLA, LIGHT/HVEM pathway: a bidirectional switch regulating t-cell activation. Immunological Reviews, 2009, vol. 229, p. 244-258.

Clémence Demerlé, et al., "Anti-HVEM mAb therapy improves antitumoral immunity both in vitro and in vivo, in a novel transgenic mouse model expressing human HVEM and BTLA molecules challenged with HVEM expressing tumors", J Immunother Cancer 2023; 15 pages. 11:e006348. doi:10.1136/jitc-2022-006348.

European Search Report for EP 22779311.4 mailed Feb. 5, 2025, 14 pages.

Ren et al. Lung Cancer. The immune checkpoint, HVEM may contribute to immune escape in non-small cell lung cancer lacking PD-L1 expression. Lung Cancer. Nov. 2018; 125:115-120. doi: 10.1016/j.lungcan.2018.09.004. Epub Sep. 1, 20182. PMID: 30429008.

Sedy, J., Gavrieli, M., Potter, K et al. B and T lymphocyte attenuator regulates T cell activation through interaction with herpesvirus entry mediator. Nat Immunol 6, 90-98 (2005). https://doi.org/10.1038/ni1144.

* cited by examiner

Human spleen (X400)

Human colon (X400)

|  | Normal | Tumor | | | | |
|---|---|---|---|---|---|---|
| Skin | NA | 0 | 2 | 2 | 2 | NA |
| Pancreas Gland | 0 | 0 | 2 | 2 | 2 | 2 |
| Lung | 0 | 0 | 2 | 2 | 3 | 4 |
| Breast | 0 | 0 | 1 | 1 | 2 | 2 |
| Bladder | 0 | 0 | 1 | 2 | 2 | 3 |
| Ovary | 0 | 0 | 1 | 2 | 4 | 5 |
| Lymph Node | 1 | 0 | 0 | 0 | 0 | 1 |
| Larynx/oral cavitiy/tongue | 1 | 0 | 1 | 1 | 2 | 3 |
| Brain | 1 | 0 | 1 | 1 | 2 | 3 |
| Kidney | 2 | 1 | 1 | 2 | 3 | NA |
| Liver | 2 | 3 | 5 | 5 | 5 | NA |
| Stomach | 5 | 0 | 1 | 1 | 3 | 3 |

Grade

0   No cells are positive
1   few cells 1-5 are positive
2   few cells 6-15 are positive
3   few cells 16-25 are positive
4   few cells 26-50 are positive
5   few cells >50 are positive

| CONDITION | Final sample concentration (µg/ml) | IL-6 | IL-8 | IL-10 | IFN-γ | TNF-α |
|---|---|---|---|---|---|---|
| Anti-ACB1 | 100 | 7.4 | 134.7 | 10.0 | 8.0 | 2.8 |
|  | 10 | 7.2 | 74.6 | 6.6 | 6.9 | 2.3 |
|  | 1 | 6.2 | 68.5 | 6.9 | 6.5 | 1.9 |
|  | 0.1 | 5.5 | 60.4 | 8.2 | 5.9 | 2.0 |
| Erbitux® | 100 | 7.3 | 103.5 | 8.9 | 7.3 | 2.6 |
| Lemtrada® | 10 | 72.6 | 616.6 | 9.9 | 38.1 | 32.0 |

Figure 13

ANTI-HVEM ANTIBODIES AND USE THEREOF

CROSS REFERENCE TO RELATED APPLICATIONS

This application is a National Phase of PCT Patent Application No. PCT/IL2020/050479 having International filing date of Apr. 28, 2020 which claims the benefit of priority of U.S. Provisional Patent Application No. 62/965, 921, filed Jan. 26, 2020 and U.S. Provisional Patent Application No. 62/839,841, filed Apr. 29, 2019, the contents of which are all incorporated herein by reference in their entirety.

FIELD OF INVENTION

The present invention is in the field of immunotherapy.

BACKGROUND OF THE INVENTION

Immunotherapies designed to enhance an immune response are considered activating immunotherapies and are at the forefront of cancer treatment. Currently, immune checkpoint blockade therapy is successfully being used for treatment of advanced non-small cell lung cancers (NSCLC), metastatic melanoma and advanced renal cell carcinoma (RCC). A few such drugs, developed and manufactured by different companies, have shown great promise in different cancer types and have been FDA approved, including antibodies to the immune checkpoints programmed cell death protein 1 receptor (PD1), programmed cell death protein 1 ligand (PDL1) and cytotoxic T lymphocyte-associated protein 4 (CTLA-4). Patient response rate, however, is still not optimal, as only 10%-40% of treated patients usually benefit, and at the same time patients may suffer from Post Immunotherapy Treatments Side-Effects. In addition, treatment with these agents, may induce resistance through upregulation of additional immune checkpoints. Combination of anti-PD1 and anti-CTLA-4 therapy in melanoma patients has demonstrated higher response rate (60%) as compared to single agent, however this combination therapy involves also severe treatment-related adverse effects. Thus, there is a clear need for new antitumor immune activating agents.

Herpesvirus entry mediator (HVEM) is a protein found on the surface of various cell types, including hematopoietic and non-hematopoietic cells. HVEM acts as a receptor for canonical TNF-related ligands such as LIGHT and LTα, thus acting as a signaling receptor. However, it also acts as a ligand for immunoglobulin (Ig) superfamily molecules such as inhibitory receptors BTLA and CD160. Therefore, bidirectional signaling is possible for the HVEM-mediated signaling network, which can be involved in positive or negative immunological reactions under different contexts. Dysregulation of this network is involved in the pathogenesis of autoimmune diseases, inflammatory diseases as well as cancer, making HVEM a target for immunotherapy.

SUMMARY OF THE INVENTION

The present invention provides agents that bind HVEM, inhibit HVEM-BTLA interaction, inhibit downstream BTLA signaling and activate downstream HVEM signaling. Methods of treating disease with those agents and kits comprising those agents are also provided.

According to a first aspect, there is provided an agent that specifically binds to Herpesvirus entry mediator (HVEM) on a cell,
- a. inhibits interaction between the HVEM and B- and T-lymphocyte attenuator (BTLA); and
- b. activates downstream signaling through the HVEM within the cell.

According to another aspect, there is provided an antibody or antigen binding fragment thereof comprises three heavy chain CDRs (CDR-H) and three light chain CDRs (CDR-L), wherein: CDR-H1 comprises the amino acid sequence set forth in SEQ ID NO: 1 (SYAMS), CDR-H2 comprises the amino acid sequence as set forth in SEQ ID NO: 2 (AISGSGGSTYYADSVKG), CDR-H3 comprises the amino acid sequence as set forth in SEQ ID NO: 3 (APGDYTAYFDY), CDR-L1 comprises the amino acid sequence as set forth in SEQ ID NO: 4 (RASQSVSSYLA), CDR-L2 comprises the amino acid sequence as set forth in SEQ ID NO: 5 (GASSRAT), and CDR-L3 comprises the amino acid sequence as set forth in SEQ ID NO: 6 (QQYGSSPPYT).

According to another aspect, there is provided a pharmaceutical composition comprising an agent of the invention, or an antibody or antigen binding fragment thereof of the invention and a pharmaceutically acceptable carrier, excipient or adjuvant.

According to another aspect, there is provided a method of treating a disease or condition characterized by HVEM positive cells, the method comprising administering the pharmaceutical composition of the invention, thereby treating the disease or condition.

According to another aspect, there is provided a method of treating an HVEM positive disease or condition, the method comprising:
- a. inhibiting HVEM and BTLA interaction; and
- b. activating HVEM signaling in an immune cell, a disease cell or both; thereby treating an HVEM positive disease or condition.

According to another aspect, there is provided a method of determining suitability of a subject to be treated by a method of the invention, comprising obtaining a disease sample from the subject and determining HVEM levels in the sample, wherein positive expression of HVEM indicates the subject is suitable for a method of treatment of the invention.

According to another aspect, there is provided a method of detecting HVEM in a sample, the method comprising contacting the sample with an agent of the invention, or an antibody or antigen binding fragment thereof of the invention, thereby detecting HVEM.

According to another aspect, there is provided a kit comprising, the pharmaceutical composition of the invention and at least one of:
- a. an anti-PD-1/PD-L1 based immunotherapy;
- b. a label stating the pharmaceutical composition of the invention is for use with an anti-PD-1/PD-L1 based immunotherapy; and
- c. a secondary detection molecule for detecting an agent of the invention, or an antibody or antigen binding fragment thereof of the invention.

According to some embodiments, the agent does not substantially inhibit interaction between the HVEM and tumor necrosis factor superfamily member 14 (TNFSF14).

According to some embodiments, the agent inhibits interaction between the HVEM and CD160, lymphotoxin alpha (LTα) or both.

According to some embodiments, the agent does not directly induce apoptosis of a cell expressing HVEM upon binding to the HVEM expressed by the cell.

According to some embodiments, the agent is an antibody or antigen binding fragment thereof.

According to some embodiments, the agent of the invention comprises an IgG2, IgG4 or a modified IgG1 or IgG3 that is not cytotoxic to the cell.

According to some embodiments, the agent is a single chain antibody (scFv).

According to some embodiments, the downstream signaling through HVEM comprises nuclear factor kappa-light-chain enhancer of activated B cells (NF-kB) mediated transcription.

According to some embodiments, the downstream signaling through HVEM comprises increased cytotoxicity of an immune cell expressing the HVEM.

According to some embodiments, the increased cytotoxicity comprises increased secretion of a proinflammatory cytokine.

According to some embodiments, the cell is an immune cell, and the signaling induces immune activation.

According to some embodiments, the immune cell is a tumor infiltrating lymphocyte (TIL) or a peripheral blood mononuclear cell (PBMC).

According to some embodiments, the cell is a cancer cell, and the signaling comprises an anti-tumor effect.

According to some embodiments, the agent of the invention for use in treating a disease characterized by disease cells expressing HVEM.

According to some embodiments, the disease is an HVEM positive cancer or precancerous lesion.

According to some embodiments, the HVEM positive cancer is selected from melanoma, renal cancer, cervical cancer, prostate cancer, pancreatic cancer, lung cancer, ovarian cancer, colon cancer, breast cancer and head and neck cancer.

According to some embodiments, the disease is an infectious disease and wherein the infected cells comprise HVEM expression.

According to some embodiments, the antibody or antigen binding fragment thereof comprises three heavy chain CDRs (CDR-H) and three light chain CDRs (CDR-L), wherein: CDR-H1 comprises the amino acid sequence set forth in SEQ ID NO: 1 (SYAMS), CDR-H2 comprises the amino acid sequence as set forth in SEQ ID NO: 2 (AISGSGG-STYYADSVKG), CDR-H3 comprises the amino acid sequence as set forth in SEQ ID NO: 3 (APGDYTAYFDY), CDR-L1 comprises the amino acid sequence as set forth in SEQ ID NO: 4 (RASQSVSSYLA), CDR-L2 comprises the amino acid sequence as set forth in SEQ ID NO: 5 (GASSRAT), and CDR-L3 comprises the amino acid sequence as set forth in SEQ ID NO: 6 (QQYGSSPPYT).

According to some embodiments, the agent of the invention comprises a heavy chain comprising the sequence

```
                                    (SEQ ID NO: 7)
QVQLVQSGGGLVQPGGSLRLSCAASGFTFSSYAMSWVRQAPGKGLEWVSA

ISGSGGSTYYADSVKGRFTISRDNSKNTLYLQMNSLRAEDTAVYYCAKAP

GDYTAYFDYWGQGTLVTVSS.
```

According to some embodiments, the agent of the invention comprises a light chain comprising the sequence

```
                                    (SEQ ID NO: 8)
ELVLTQSPATLSLSPGERATLSCRASQSVSSYLAWYQQKPGQAPRLLIYG

ASSRATGIPDRFSGSGSGTDFTLTISRLEPEDFAVYYCQQYGSSPPYTFG

QGTKVEIK.
```

According to some embodiments, the agent of the invention comprises a heavy chain comprising the sequence MGWSCIILFLVATATGVHSQVQLVQSGG-GLVQPGGSLRLSCAASGFTFSSYAMSW VRQAPGK-GLEWVSAISGSGGGSTYYADSVKGRFTISRDNSKNT-LYLQMNSLRAEDT AVYYCAKAPGDYTAYFDYWGQGTLVTVSSAS-TKGPSVFPLAPCSRSTSESTAALG CLVKDYF-PEPVTVSWNSGALTSGVHTFPAVLQSSGLYS-LSSVVTVPSSSLGTKTYT CNVDHKPSNTKVDKRVESKYGPPCPPCPAPE-FLGGPSVFLFPPKPKDTLMISRTPEV TCVVVDVSQEDPEVQFNWYVDGVEVHNAKTKPRE-EQFNSTYRVVSVLTVLHQD WLNGKEYKCKVSNKGLPSSIEKTISKAKGQPREPQV YTLPPSQEEMTKNQVSLTCL VKGFYPSDIA-VEWESNGQPENNYKTTPPVLDSDGSFFLY-SRLTVDKSRWQEGNVF SCSVMHEALHN-HYTQKSLSLSLGK (SEQ ID NO: 9) and a light chain comprising the sequence MGWSCIILFLVATATGVH-SELVLTQSPATLSLSPGERATLSCRASQSVSSYLAWYQ QKPGQAPRLLIYGASSRAT-GIPDRFSGSGSGTDFTLTISRLEPEDFAVYYCQQYGSS PPYTFGQGTKVEIKRTVAAPSVFIFPPSDEQLKSG-TASVVCLLNNFYPREAKVQWK VDNALQSGNSQESVTEQDSKDSTYSLSSTLTL-SKADYEKHKVYACEVTHQGLSSP VTKSFNRGEC (SEQ ID NO: 10).

According to some embodiments, the antibody or antigen binding fragment of the invention comprises a heavy chain comprising the sequence

```
                                    (SEQ ID NO: 7)
QVQLVQSGGGLVQPGGSLRLSCAASGFTFSSYAMSWVRQAPGKGLEWVSA

ISGSGGSTYYADSVKGRFTISRDNSKNTLYLQMNSLRAEDTAVYYCAKAP

GDYTAYFDYWGQGTLVTVSS.
```

According to some embodiments, the antibody or antigen binding fragment of the invention comprises a light chain comprising the sequence

```
                                    (SEQ ID NO: 8)
ELVLTQSPATLSLSPGERATLSCRASQSVSSYLAWYQQKPGQAPRLLIYG

ASSRATGIPDRFSGSGSGTDFTLTISRLEPEDFAVYYCQQYGSSPPYTFG

QGTKVEIK.
```

According to some embodiments, the antibody or antigen binding fragment of the invention comprises a heavy chain comprising the sequence MGWSCIILFL-VATATGVHSQVQLVQSGGGLVQPGGSLRLS-CAASGFTFSSYAMSW VRQAPGKGLEWVSAISGSGG-STYYADSVKGRFTISRDNSKNTLYLQMNSLRAEDT AVYYCAKAPGDYTAYFDYWGQGTLVTVSSAS-TKGPSVFPLAPCSRSTSESTAALG CLVKDYF-PEPVTVSWNSGALTSGVHTFPAVLQSSGLYS-LSSVVTVPSSSLGTKTYT CNVDHKPSNTKVDKRVESKYGPPCPPCPAPE-

5

FLGGPSVFLFPPKPKDTLMISRTPEV
TCVVVDVSQEDPEVQFNWYVDGVEVHNAKTKPRE-
EQFNSTYRVVSVLTVLHQD
WLNGKEYKCKVSNKGLPSSIEKTISKAKGQPREPQV
YTLPPSQEEMTKNQVSLTCL VKGFYPSDIA-
VEWESNGQPENNYKTTPPVLDSDGSFFLY-
SRLTVDKSRWQEGNVF SCSVMHEALHN-
HYTQKSLSLSLGK (SEQ ID NO: 9) and a light chain
comprising the sequence

```
                                                (SEQ ID NO: 10)
MGWSCIILFLVATATGVHSELVLTQSPATLSLSPGERATLSCRASQSVSS

YLAWYQQKPGQAPRLLIYGASSRATGIPDRFSGSGSGTDFTLTISRLEPE

DFAVYYCQQYGSSPPYTFGQGTKVEIKRTVAAPSVFIFPPSDEQLKSGTA

SVVCLLNNFYPREAKVQWKVDNALQSGNSQESVTEQDSKDSTYSLSSTLT

LSKADYEKHKVYACEVTHQGLSSPVTKSFNRGEC.
```

According to some embodiments, the method of the invention further comprises administering an anti-PD-1/PD-L1 based immunotherapy.

According to some embodiments, the method of the invention further comprises administering adoptive cell therapy.

According to some embodiments, the adoptive cell therapy comprises adoptive TIL therapy.

According to some embodiments, the adoptive cell therapy comprises administering a chimeric antigen receptor (CAR) expressing immune cell, wherein the CAR targets a non-HVEM protein on a surface of the HVEM expressing cells.

According to some embodiments, the method of the invention further comprises inhibiting PD-1 and PD-L1 interaction.

According to some embodiments, the method of the invention further comprises not substantially inhibiting HVEM and TNFSF14 interaction.

According to some embodiments, the disease or condition is an HVEM positive cancer or precancerous lesion.

According to some embodiments, the HVEM positive cancer is selected from melanoma and renal cell carcinoma.

According to some embodiments, the disease or condition is an infectious disease and wherein the infected cells comprise HVEM expression.

According to some embodiments, the immune cell is a TIL or PBMC.

According to some embodiments, the immune cell is a CAR-T cell.

According to some embodiments, the method of the invention comprises administering the pharmaceutical composition of the invention.

According to some embodiments, positive expression of HVEM comprises an elevated HVEM level as compared to a healthy sample or predetermined threshold.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

6 human HVEM (CHO-K1 hrHVEM), mouse HVEM (CHO-K1 mrHVEM), cynomolgus HVEM (CHO-K1 crHVEM) or empty vector as control (CHO-K1 empty) were incubated for 1 hour on ice with 5 μg/ml of lysates containing HIS-tagged scFv1-6 or control lysate followed by staining with anti-HIS APC antibody (R&D Systems, USA) or isotype control antibody (R&D Systems, USA). Expression was assessed by flow cytometry using CytoFLEX instrument (Beckman Coulter, USA) and data analysis using FCS Express 6 software (DeNovo Software, US). Solid black line represents background staining (i.e. isotype control antibody) of CHO-K1 empty cells, dotted grey line represents specific antibody staining of CHO-K1 empty cells, dotted black line represents specific antibody staining of CHO-K1 hrHVEM cells, solid grey line represents specific antibody staining of CHO-K1 mrHVEM cells and dashed black line represents specific antibody staining of CHO-K1 crHVEM cells.

Figure 2A:
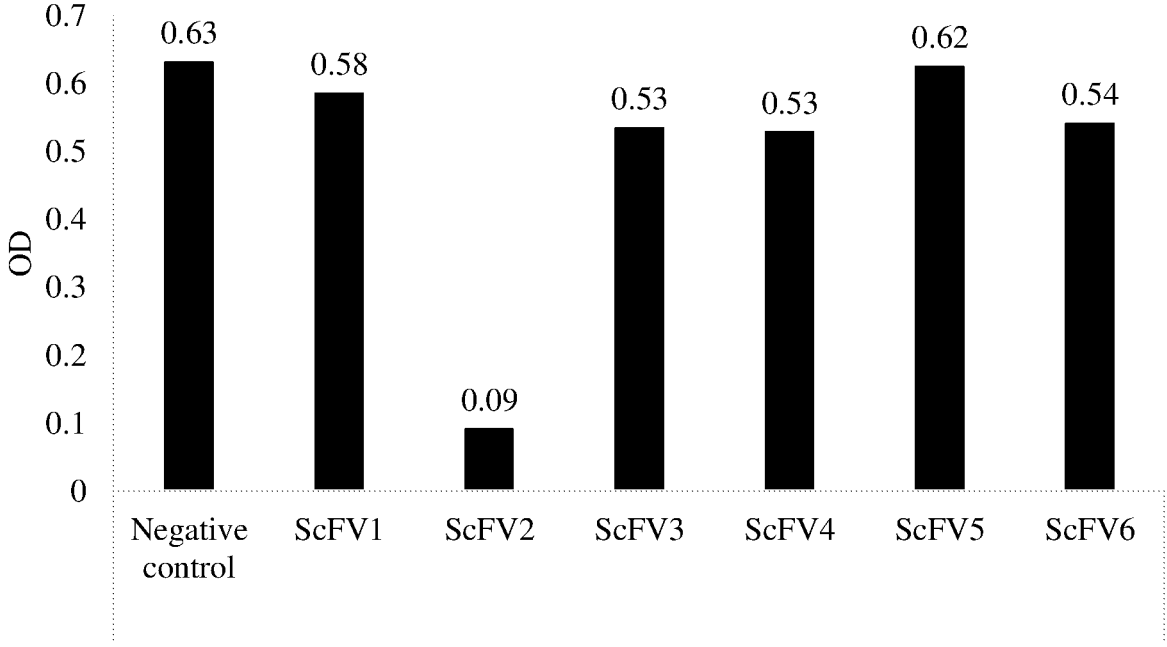
Figure 2B:
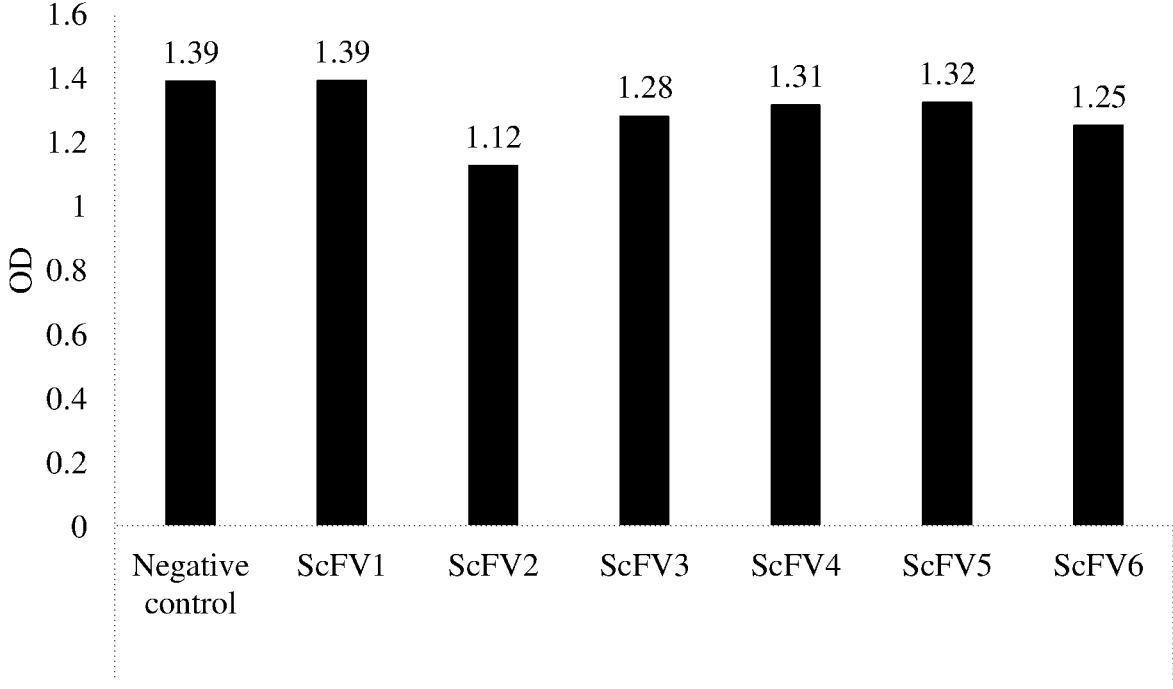

FIGS. 2A-2B. Bar graphs of hrHVEM binding-ELISA to (2A) hrBTLA and (2B) hrLIGHT in the presence of the six scFvs.

Figure 3:
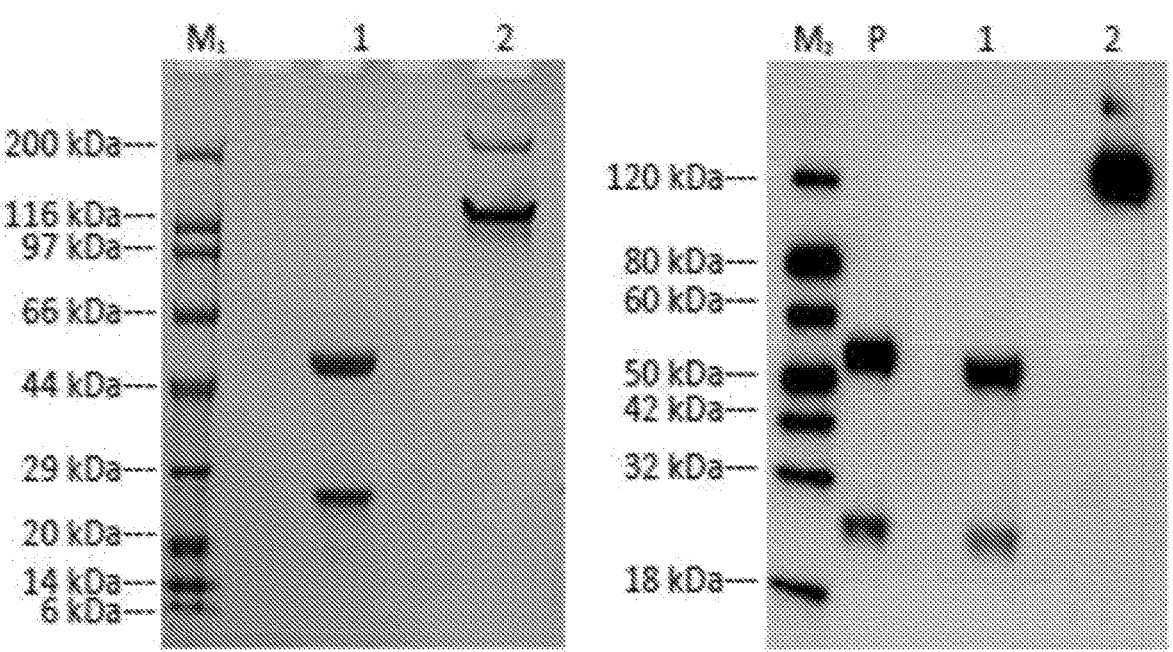

FIG. 3. SDS-PAGE and Western Blot analysis of scFv2-IgG4 (S228P): Purified protein was analyzed by SDS-PAGE (left panel) and western blot (right panel) to measure molecular weight and purity. Lanes M1 and M2 indicates protein marker. Lane 1 and 2 indicate reducing and non-reducing conditions, respectively. Lane P indicate human IgG1-k as positive control.

Figure 4A:
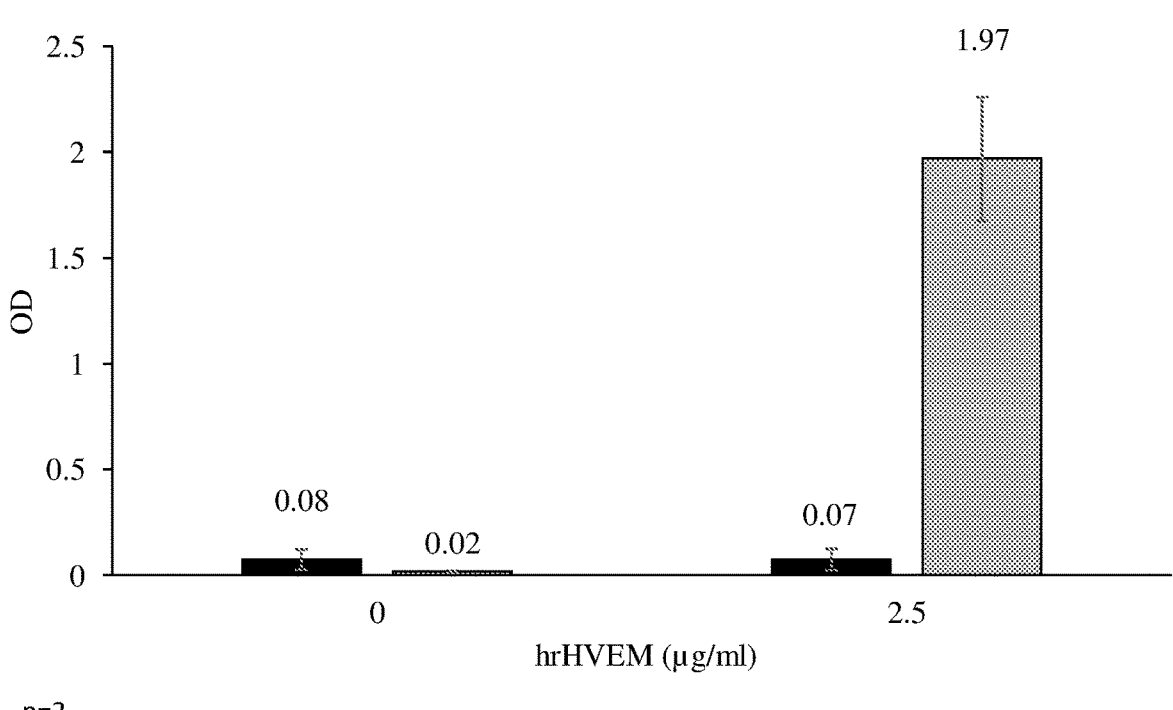
Figure 4B:
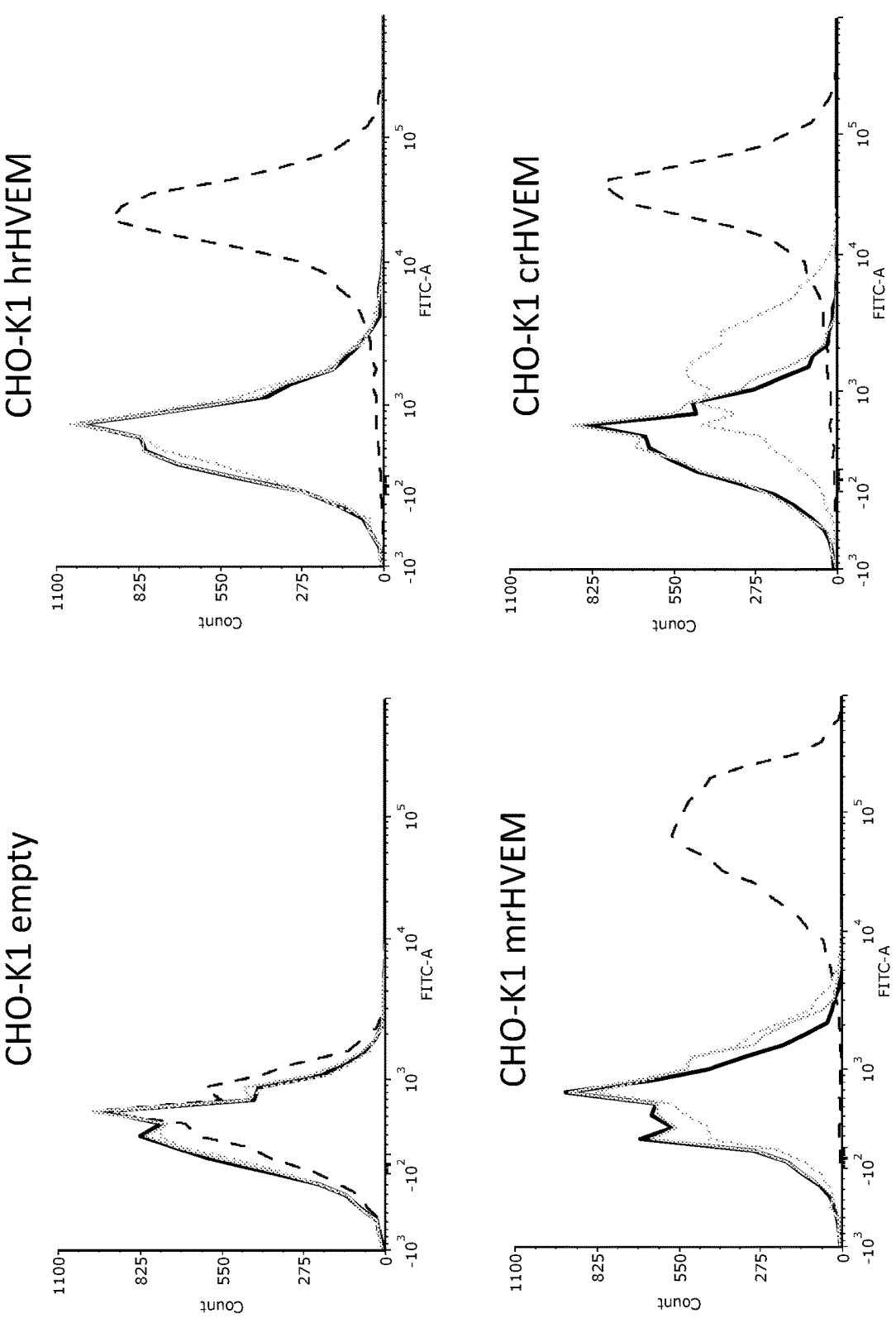

FIGS. 4A-4B. (4A) Bar graph of mAb of the invention binding to hrHVEM as measured by ELISA. (4B) Histograms of binding of the mAb of the invention or hIgG4 isotype control antibody to hrHVEM, mrHVEM and crHVEM. expressed on CHO-K1 cells. Solid black and grey lines represent background staining (i.e., secondary anti-Biotin FITC antibody) of hIgG4 isotype control antibody and the mAb of the invention, respectively. Dotted grey and dashed black lines represent specific antibody staining (i.e., anti-human IgG Fc Biotin antibody+anti-biotin FITC antibody) of hIgG4 isotype control antibody and the mAb of the invention, respectively.

FIGS. 5A-5F. (5A) Micrographs of HVEM staining on healthy human colon and spleen tissue samples using the mAb of the invention. (5B) Histograms of binding of a commercially available anti-HVEM antibody (R&D Systems AF356) to two different melanoma patient primary cell samples. Solid black and grey lines represent background staining (i.e, secondary anti-mouse APC antibody) and specific antibody staining, respectively. (5C) Histograms of binding of the mAb of the invention to three different melanoma patient primary cell samples. Solid and dashed lines represent background staining (i.e. secondary anti-Biotin FITC antibody) and specific antibody staining (i.e. anti-human IgG Fc Biotin antibody+anti-biotin FITC antibody), respectively. (5D) Histogram of the same staining as in 5B but on cells from a renal cell carcinoma (RCC) patient. (5E) Histogram of the same staining as in 5C, but on cells from the RCC patient. (5F) Table of HVEM expression in various healthy and tumor samples as determined using the mAb of the invention. "NA": "not applicable" as the tissue core was absent/destroyed.

FIGS. 6A-6D. Bar graphs of hrHVEM binding-ELISA to (6A) hrBTLA and (6B) hrLIGHT in the presence of the mAb of the invention or hIgG4 isotype control antibody, (6C) to commercially available anti-HVEM mAb (R&D Systems, MAB356), and (6D) hrBTLA in the presence of MAB356 or mIgG1 isotype control antibody.

7
8

Figure 7:
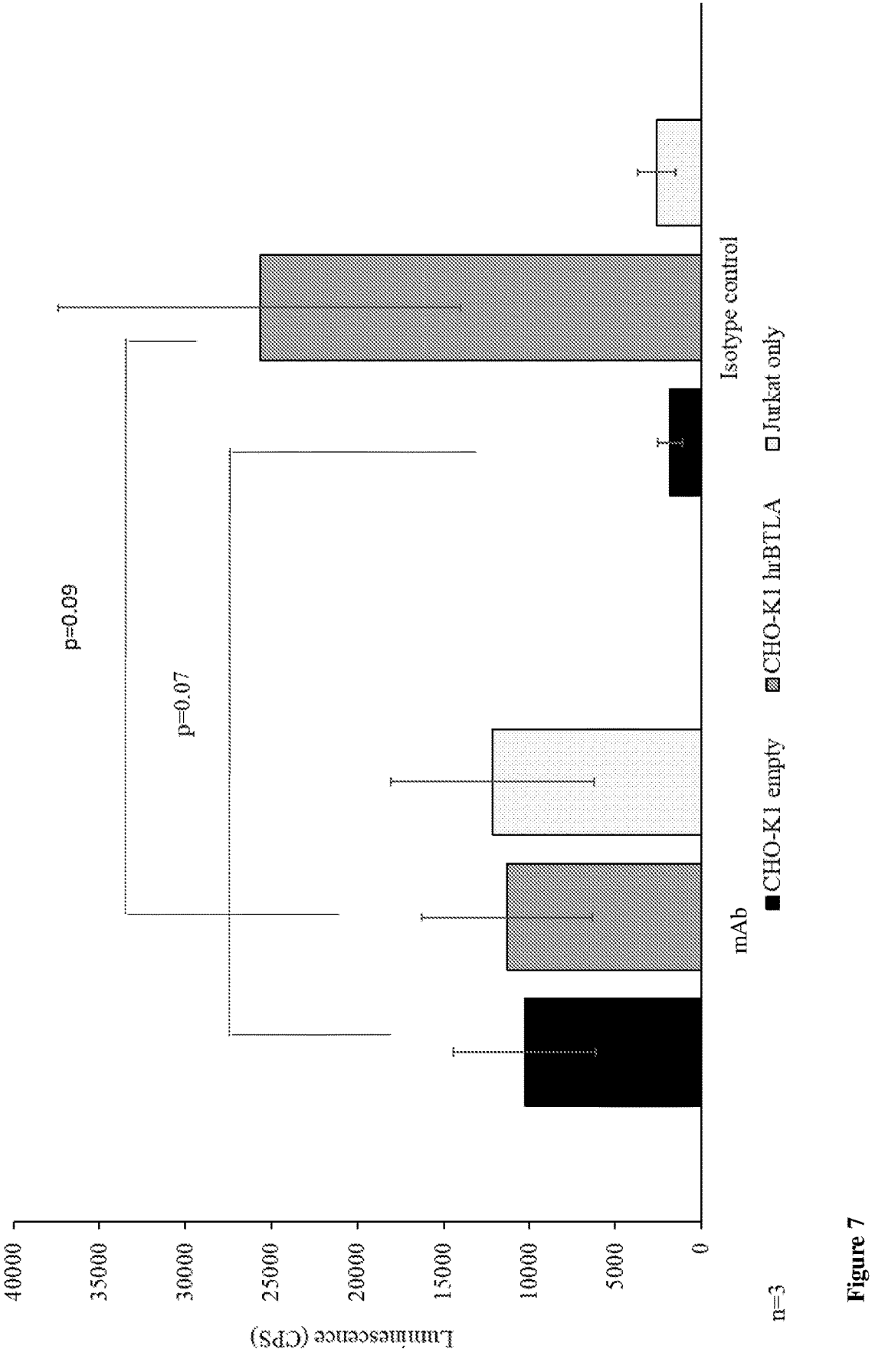

FIG. 7. Bar graphs of luciferase output from Jurkat cells expressing hrHVEM and an NF-kB luciferase reporter after pre-incubation with the mAb of the invention (left) and a control hIgG4 (right) followed by coincubation with empty CHO-K1 cells, CHO-K1 cells expressing hrBTLA and no cells.

Figure 8:
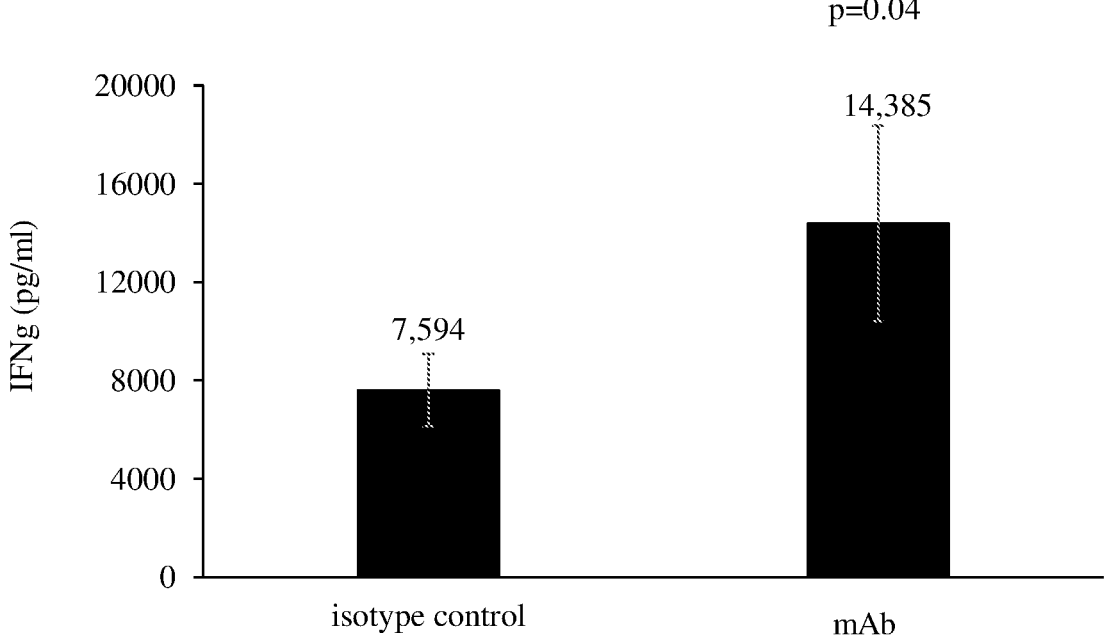
Figure 8:
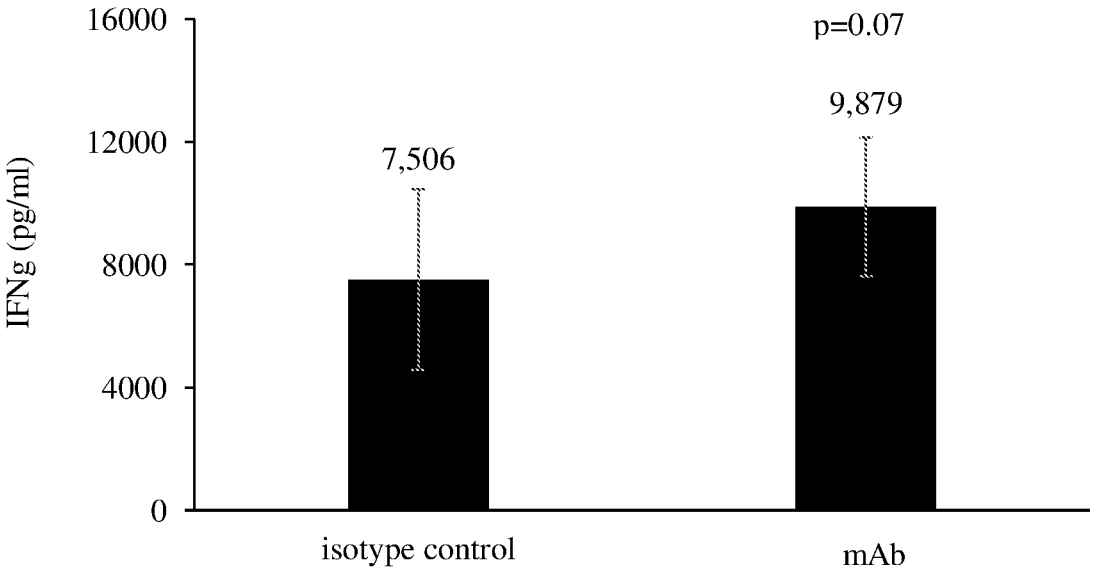

FIG. 8. Bar graphs showing IFNγ secretion by TILs post co-culture with melanoma cells from two separate patients pre-incubated with the mAb of the invention or hIgG4 isotype control.

FIGS. 9A-9E. (9A-B). Line graphs of specific killing of melanoma cells from (9A) a first primary patient sample, (9B) a second primary patient sample and of (9C) RCC cell from a primary patient sample at various time points during coincubation with autologous TILs. Black circle, white square, black triangle and black diamond lines represent incubation with hIgG4 isotype control antibody, mAb of the invention, anti-PD1 mAb or mAb of the invention+anti-PD1 mAb, respectively. (9D-E) Line graphs of specific killing of melanoma cells from a primary patient sample preincubated with (9D) the mAb of the invention or (9E) MAB356 at various time points during coincubation with autologous TILs. Black circle and white square represent incubation with isotype control antibody and mAb, respectively.

Figure 10A:
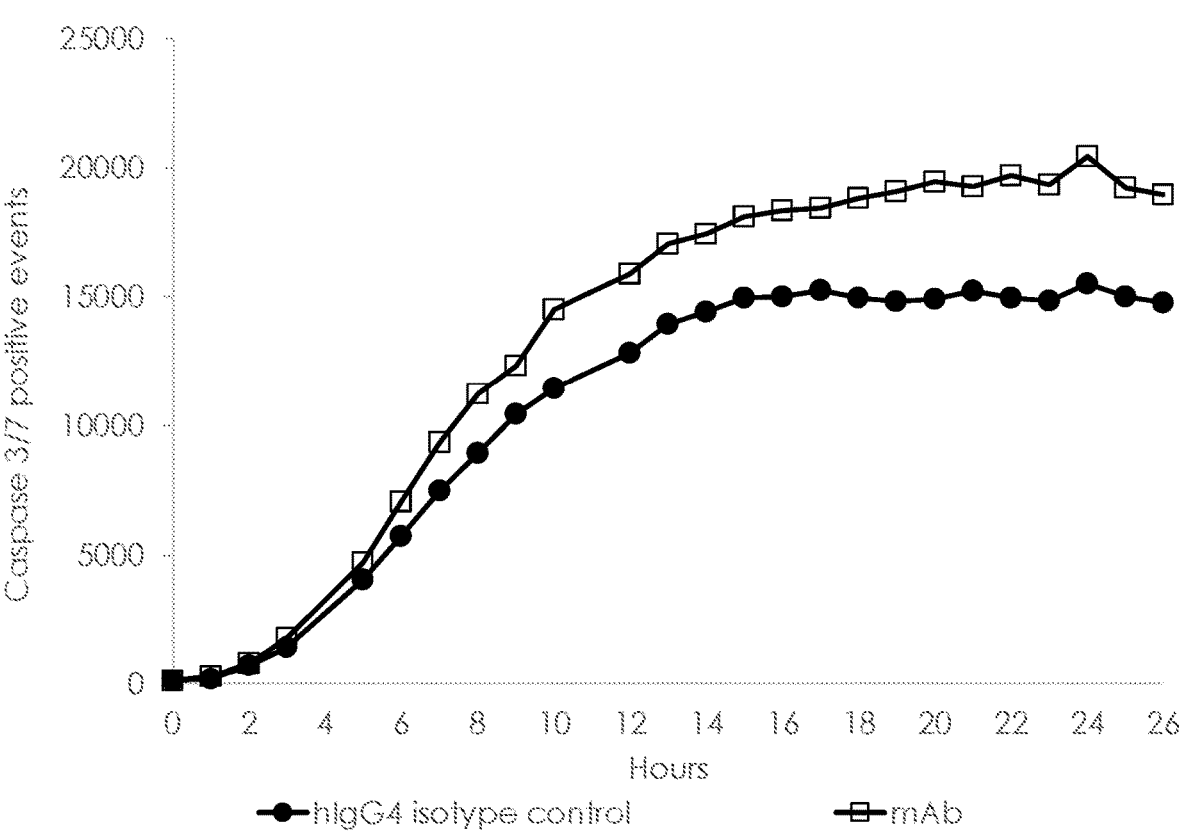
Figure 10B:
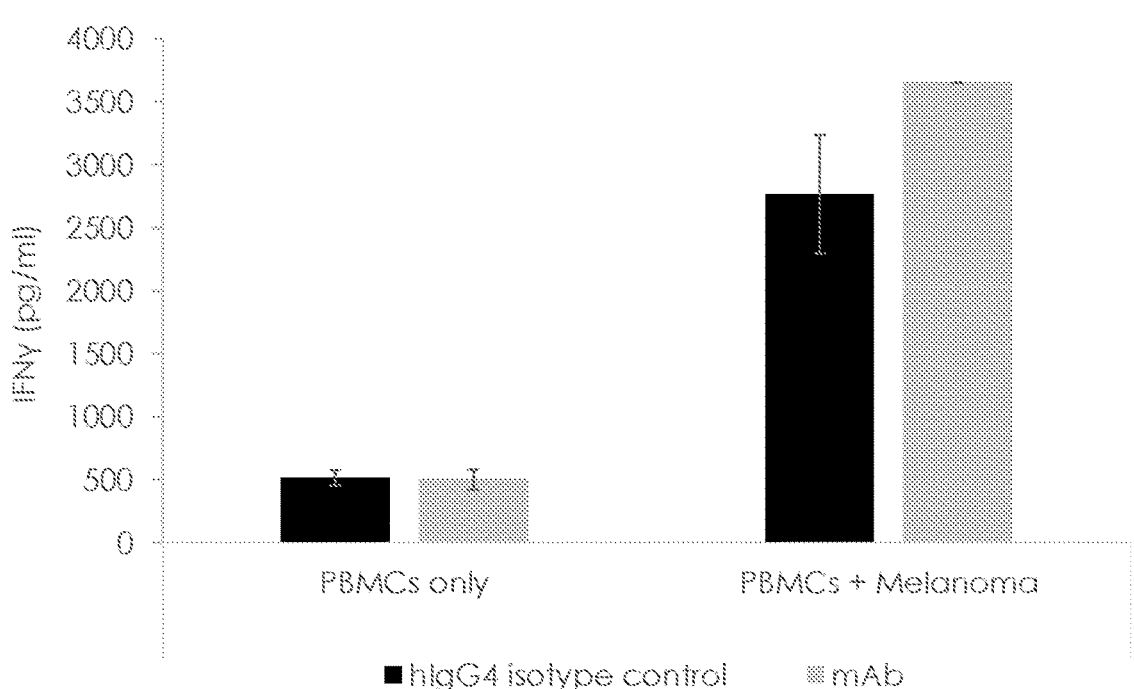

FIGS. 10A-10B. (10A) Line graph of specific killing of melanoma cells from a primary patient sample at various time points during coincubation with non-autologous PBMCs from a healthy donor. Black circles represent hIgG4 isotype control antibody and white squares represent mAb of the invention. (10B) Bar graph of IFNγ secretion from PBMCs cultured alone or with melanoma cells incubated with a hIgG4 isotype control antibody, or the mAb of the invention.

Figure 11:
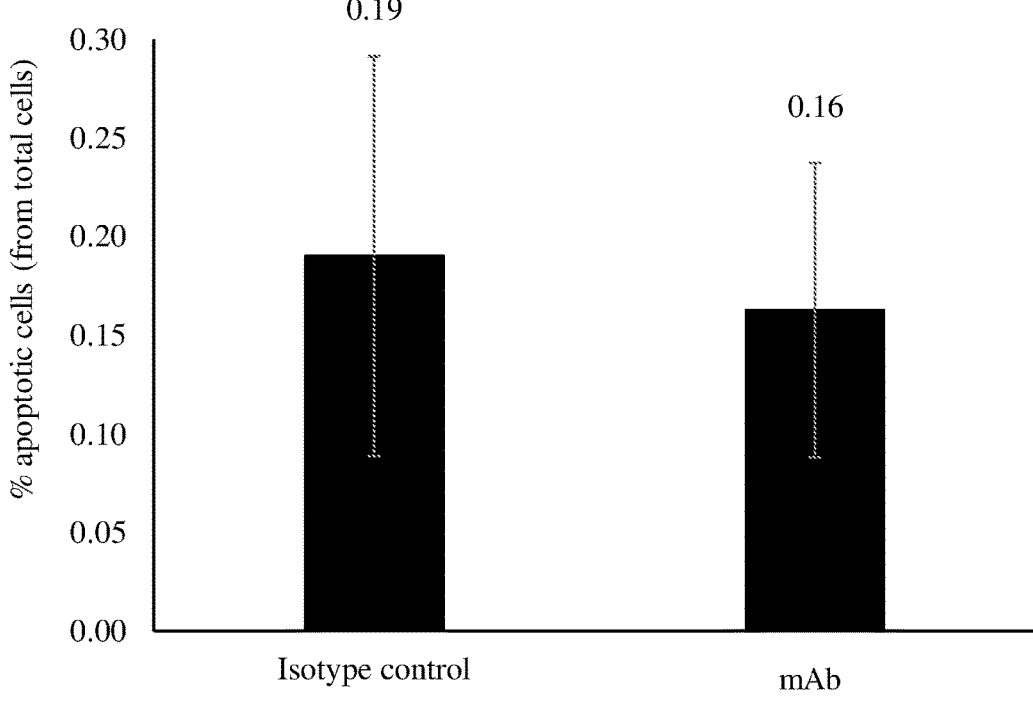
Figure 11:
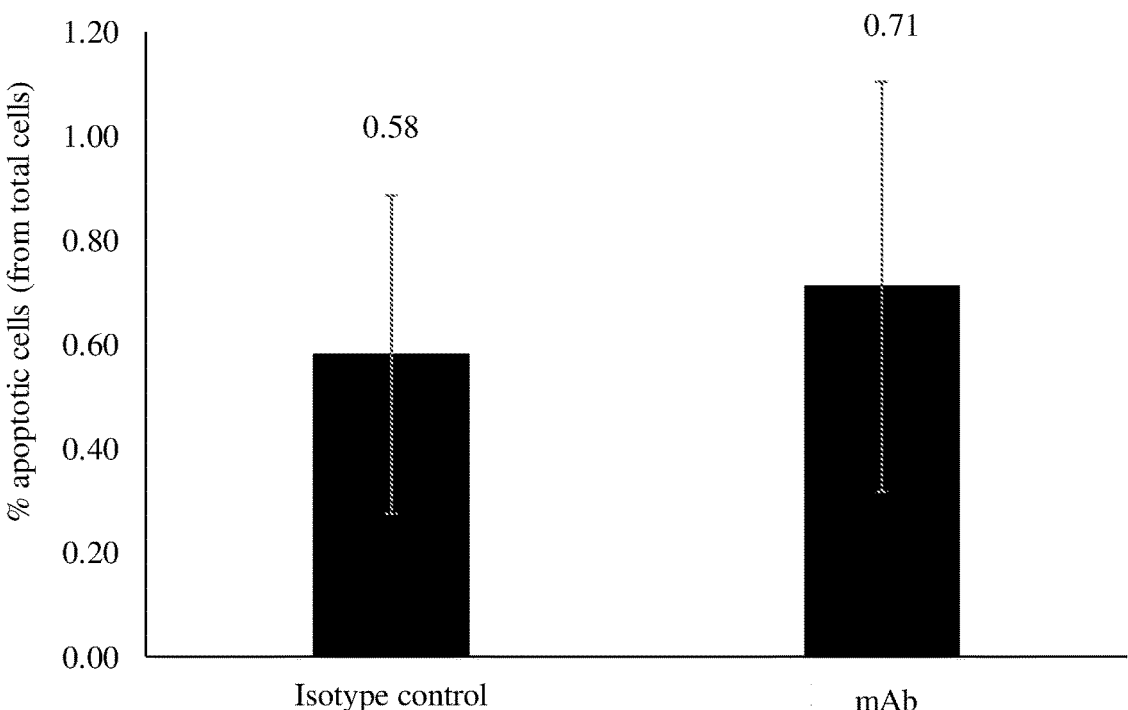

FIG. 11. Bar charts showing the percent of Caspase 3/7 positive events from total number of melanoma cells after 15 hours incubation, reflecting apoptosis of melanoma cells from two primary samples incubated with the mAb of the invention and a hIgG4 isotype control.

FIGS. 12A-12D. (12A) Histogram of 41BB FACS staining in T cells as a measure of activation. Thick solid black line represent background staining (i.e., APC-conjugated isotype control antibody), dotted black line represents 41BB staining of TILs incubated with media containing hIgG4 isotype control, thin solid black line represents 41BB staining of TILs incubated with media containing the mAb of the invention, dotted grey line represents 41BB staining of TILs incubated with melanoma cells pre-incubated with hIgG4 isotype control and thin solid grey line represents 41BB staining of TILs incubated with melanoma cell pre-incubated with the mAb of the invention. (12B-C) Bar graphs of the average number of T-cell clusters observed after TILs from melanoma patients were incubated for 20 hours with the (12B) mAb of the invention or hIgG4 isotype control antibody and (12C) MAB356 or mIgG1 isotype control. (12D) Expression of 41BB on PBMCs cultured with melanoma cells pre-incubated with hIgG4 isotype control or with the mAb of the invention, as measured by microscopy at various time points.

FIG. 13. Table of cytokine secretion after cytokine release assay with the mAb of the invention and two commercially available antibodies.

Figure 14:
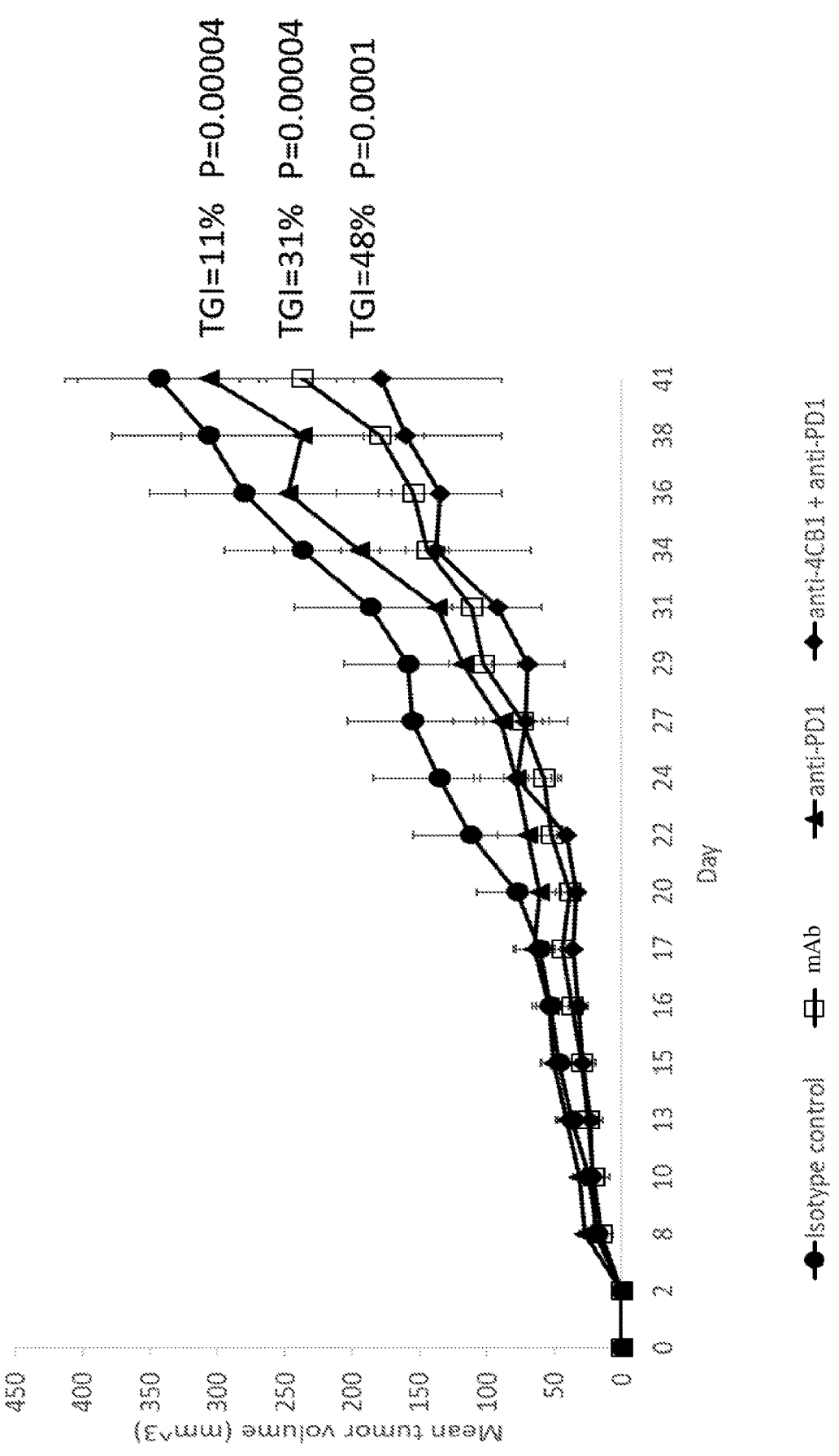

FIG. 14. Line graphs of mean tumor volume from various time points in mice implanted with human melanoma cells and treated with human autologous TILs. Black circle, white square, black triangle and black diamond lines represent incubation with hIgG4 isotype control antibody, mAb of the invention, anti-PD1 mAb or mAb of the invention+anti-PD1 mAb, respectively.

DETAILED DESCRIPTION OF THE INVENTION

The present invention, in some embodiments, provides agents that bind HVEM, inhibit HVEM-BTLA interaction and are also agonists of HVEM. The present invention further concerns methods of treating HVEM positive disease and kits comprising these agents.

It is well known that HVEM positive cancers can avoid immune surveillance by binding BTLA on the surface of immune cells. Engagement of BTLA produces an inhibitory signal within the immune cell, which reduces T cell proliferation and increases cancer survival. Inhibiting this signaling with antibodies that bind HVEM or antibodies that bind BTLA is known. The present invention is based on the surprising finding that antibodies that specifically bind HVEM and activate HVEM signaling provide another benefit to fighting cancer: increased immune cell activation. HVEM is also expressed on the surface of immune cells however, its role there is poorly understood. The antibody of the invention not only blocks the HVEM-BTLA interaction by binding HVEM on pathogenic cells thus freeing immune cells from inhibition, but it also binds HVEM on immune cells and induces NF-kB signaling in those immune cells which enhances activation characteristics.

By a first aspect, there is provided an agent that binds to Herpesvirus entry mediator (HVEM), inhibits interaction between HVEM and B- and T-lymphocyte attenuator (BTLA).

In some embodiments, the agent activates downstream signaling through the HVEM. In some embodiments, the agent inhibits downstream signaling through the BTLA. In some embodiments, the agent activates downstream signaling through the HVEM and inhibits downstream signaling through the BTLA. In some embodiments, inhibiting interaction between the HVEM and BTLA inhibits downstream signaling through the BTLA.

In some embodiments, HVEM is mammalian HVEM. In some embodiments, HVEM is rodent HVEM. In some embodiments, HVEM is monkey HVEM. In some embodiments, HVEM is human HVEM. In some embodiments, HVEM is any one of mouse, monkey and human HVEM. In some embodiments, HVEM is membrane bound HVEM. In some embodiments, HVEM is HVEM on a cell. In some embodiments, HVEM is HVEM on a cell surface. In some embodiments, HVEM is soluble HVEM.

In some embodiments, the cell is a pathogenic cell. In some embodiments, the cell is a cancerous cell. In some embodiments, the cell is a cell of a pathogen. In some embodiments, the cell is a bacterial cell. In some embodiments, the cell is a fungal cell. In some embodiments, the cell is a eukaryotic cell infected by a pathogen. In some embodiments, the cell is a cell infected by a bacterium. In some embodiments, the cell is a cell infected by a virus. In some embodiments, a pathogen is selected from a bacterium, a virus and a fungus.

In some embodiments, the cell is an immune cell. In some embodiments, the cell is a hematopoietic cell. In some embodiments, the immune cell is a T-cell. In some embodiments, the T-cell is a CD8 positive T-cell. In some embodiments, the T-cell is a cytotoxic CD8 positive T-cell. In some embodiments, the T-cell is a CD4 positive T-cell. In some embodiments, the T-cell is a CD4 positive helper T-cell. In some embodiments, the T-cell is selected from a CD8 positive and a CD4 positive T-cell. In some embodiments, the T-cell is a CD8 positive T-cell, a CD4 positive T-cell or both. In some embodiments, the immune cell is a tumor infiltrating lymphocyte (TIL). In some embodiments, the immune cell is not a peripheral blood immune cell. In some embodiments, the immune cell is a B-cell. In some embodiments, the immune cell is a natural killer (NK) cell. In some embodiments, the immune cell is a neutrophil. In some embodiments, the immune cell is a dendritic cell. In some embodiments, the immune cell is a macrophage. In some embodiments, the immune cell is a myeloid derived suppressor cell (MDSC). In some embodiments, the cell is selected from a T-cell, a B-cell, an NK cell, a neutrophil, a dendritic cell, an MDSC and a macrophage. In some embodiments, the cell is selected from a T-cell, a B-cell, an NK cell, a neutrophil, a dendritic cell, and a macrophage.

In some embodiments, the immune cell is a chimeric antigen receptor (CAR) expressing immune cell. In some embodiments, the CAR is a CAR-T cell. In some embodiments, the CAR is a CAR-NK cell. As used herein, the terms "CAR" refers to an engineered receptor which has specificity for at least one protein of interest (for example a protein expressed by an HVEM expressing cell) and is grafted onto an immune effector cell (such as a T cell or NK cell). In some embodiments, the CAR-T cell has the specificity of a monoclonal antibody grafted onto a T-cell. In some embodiments, the CAR-NK cell has the specificity of a monoclonal antibody grafted onto a NK-cell. In some embodiments, the T cell is selected from a cytotoxic T lymphocyte and a regulatory T cell. MART1 is an example of a target protein co-expressed with HVEM on target cells. In some embodiments, the CAR targets a protein expressed by the HVEM expressing cells. In some embodiments, the protein is not HVEM. In some embodiments, the CAR targets a protein on the surface of the HVEM expressing cells. In some embodiments, the protein is an antibody. In some embodiments, the CAR targets an antibody. In some embodiments, the CAR targets an antibody of the invention. In some embodiments, the CAR targets a cytotoxic antibody. In some embodiments, the CAR targets an antibody constant domain. In some embodiments, the CAR targets an Fc domain. In some embodiments, the CAR therapy further comprises administering an antibody that targets the HVEM expressing cells. In some embodiments, embodiments, the antibody targeted by the CAR is not the antibody of the invention.

CAR-T and CAR-NK cells and their vectors are well known in the art. Such cells target and are cytotoxic to the protein for which the receptor binds. In some embodiments, a CAR-T or CAR-NK cell targets at least one cancer protein. In some embodiments, a CAR-T or CAR-NK cell targets a plurality of cancer proteins.

Construction of CAR-T cells is well known in the art. In one non-limiting example, a monoclonal antibody to a cancer protein can be made and then a vector coding for the antibody will be constructed. The vector will also comprise a costimulatory signal region. In some embodiments, the costimulatory signal region comprises the intracellular domain of a known T cell or NK cell stimulatory molecule. In some embodiments, the intracellular domain is selected from at least one of the following: CD3Z, CD27, CD28, 4-1BB, OX40, CD30, CD40, PD-1, ICOS, lymphocyte function-associated antigen-1 (LFA-1), CD2, CD 7, LIGHT, NKG2C, B7-H3, and a ligand that specifically binds with CD83. In some embodiments, the vector also comprises a CD3Z signaling domain. This vector is then transfected, for example by lentiviral infection, into a T-cell.

In some embodiments, HVEM is Tumor necrosis factor receptor superfamily member 14 (TNFRSF14). In some embodiments, HVEM is CD270. In some embodiments, HVEM is a receptor of BTLA. In some embodiments, HVEM is a ligand of BTLA. In some embodiments, BTLA is CD272. In some embodiments, HVEM is a receptor of Tumor necrosis factor superfamily member 14 (TNFSF14). In some embodiments, HVEM is a ligand of TNFSF14. In some embodiments, the TNFSF14 is LIGHT. In some embodiments, TNFSF14 is CD258. In some embodiments, HVEM is a receptor of CD160. In some embodiments, HVEM is a ligand of CD160. In some embodiments, HVEM is a receptor of lymphotoxin alpha (LTα). In some embodiments, HVEM is a ligand of LTα. In some embodiments, LTα is TNF-β.

In some embodiments, the agent specifically binds to HVEM. In some embodiments, the agent binds no other protein other than HVEM. In some embodiments, the agent binds an extracellular domain of HVEM. In some embodiments, the agent binds in a ligand binding domain of HVEM. In some embodiments, the agent binds in a BTLA binding domain of HVEM. In some embodiments, the agent occludes a BTLA binding domain of HVEM. In some embodiments, the agent inhibits interaction between HVEM and BTLA. In some embodiments, the agent blocks interaction between HVEM and BTLA. In some embodiments, the agent inhibits HVEM mediated, BTLA induced immune suppression. In some embodiments, the agent binds HVEM and prohibits the bound HVEM from further binding BTLA. In some embodiments, the agent inhibits downstream signaling through BTLA. In some embodiments, the agent reduced downstream signaling through BTLA.

In some embodiments, the agent does not inhibit interaction between HVEM and TNFSF14. In some embodiments, the agent inhibits interaction between HVEM and TNFSF14. In some embodiments, the TNFSF14 is membranal TNFSF14 (mTNFS14). In some embodiments, the TNFSF14 is soluble TNFSF14 (sTNFS14). In some embodiments, that agent does not inhibit interaction between HVEM and one of mTNFS14 and sTNFS14 but does inhibit interaction with the other. In some embodiments, that agent does not inhibit interaction between both of mTNFS14 and sTNFS14 and HVEM. In some embodiments, inhibition is substantial inhibition. In some embodiments, inhibition is at least a 5, 10, 15, 20, 25, 30, 40, 50, 60, 70, 80, 90, 95, 97, 99 or 100% reduction. Each possibility represents a separate embodiment of the invention. In some embodiments, the agent does not block interaction between HVEM and TNFSF14. In some embodiments, the agent does not substantially block interaction between HVEM and TNFSF14. In some embodiments, the agent does not block/inhibit TNFSF14 mediated signaling. In some embodiments, the agent does not block/inhibit TNFSF14 mediated cell survival.

In some embodiments, the agent activates signaling through HVEM. In some embodiments, the agent is an HVEM agonist. In some embodiments, the agent induces signaling though HVEM. In some embodiments, signaling through HVEM is HVEM downstream signaling. In some embodiments, the agent binds HVEM on a cell and activates/induces HVEM signaling in the cell. In some embodiments, HVEM signaling comprises activation of nuclear factor kappa-light-chain-enhancer of activated B cells (NF-kB) signaling. In some embodiments, NF-kB signaling comprises control of genes with an NF-kB response element in their promoter. In some embodiments, the signaling comprises increased cytotoxicity of a cell. In some embodiments, the signaling comprises increased cytotoxicity of a cell expressing HVEM contacted by the agent. In some embodiments, increased cytotoxicity comprises increased secretion of a proinflammatory cytokine. In some embodiments, the proinflammatory cytokine is selected from IL-1, IL-1B, IL-4, IL-6, TNFα, IFNγ, MCP1, IL-12, IL-18, IL-23 and CM-CSF. In some embodiments, the proinflammatory cytokine is IFNγ. In some embodiments, the increase is as compared to a cell not contacted by the agent of the invention. In some embodiments, the increase is at least a 10, 20, 25, 30, 40, 50, 60, 70, 75, 80, 90, 95, 100, 110, 120, 130, 140, 150, 200, 250, 300, 350, 400, 450, or 500% increase. Each possibility represents a separate embodiment of the invention.

In some embodiments, the cell is an immune cell and the signaling comprises immune activation. In some embodiments, the immune cell is a lymphocyte. In some embodiments, the immune cell is a T cell. In some embodiments, the immune cell is a CD8+ T cell. In some embodiments, the immune cell is a CD4+ T cell. In some embodiments, the immune cell is not a gamma/delta T cell. In some embodiments, the immune cell is a gamma/delta T cell. In some embodiments, the immune cell is an NK cell. In some embodiments, activating HVEM signaling comprises activating the immune cell. In some embodiments, immune activation comprises increased proliferation. In some embodiments, immune activation comprises increased cytotoxicity. In some embodiments, immune activation comprises increased migration. In some embodiments, immune activation comprises increased homing. In some embodiments, immune activation comprises increased cell clustering. In some embodiments, immune activation is T cell activation. In some embodiments, immune activation comprises an increase in the number of Th1 T cells. In some embodiments, the increase is a relative increase as compared to Th2 T cells. In some embodiments, immune activation comprises an increase in CD8+ T cells. In some embodiments, immune activation comprises a decrease in T regulatory cells. In some embodiments, immune activation comprises an increase in the expression of a marker selected from: 41BB, CD69, CD25, CD107a, HLA-DR and secretion of a cytokine. In some embodiments, the cytokine is a proinflammatory cytokine. In some embodiments, T cell activation comprises increased T cell clustering.

In some embodiments, cell is a cancerous cell and the signaling comprises an anti-tumor effect. In some embodiments, the anti-tumor effect comprises increased apoptosis. In some embodiments, the anti-tumor effect comprises decreased proliferation. In some embodiments, the anti-tumor effect comprises increased chemotherapeutic sensitivity. In some embodiments, the anti-tumor effect comprises decreases motility. In some embodiments, the anti-tumor effect comprises decreases invasion. In some embodiments, the anti-tumor effect comprises decreased metastasis. In some embodiments, the anti-tumor effect comprises decreased self-renewal. In some embodiments, the effect is as compared to a cancer cell than was not contacted by the agent of the invention. In some embodiments, the decrease is at least a 10, 20, 25, 30, 40, 50, 60, 70, 75, 80, 90, 95, 97, 99 or 100% decrease. Each possibility represents a separate embodiment of the invention.

In some embodiments, the agent does not induce apoptosis. In some embodiments, inducing apoptosis is directly inducing apoptosis. In some embodiments, the agent does not directly induce apoptosis. As used herein, "direct induction" refers to a result that occurs as an immediate result of binding of the agent and does not feature downstream signaling within the bound cell. In some embodiments, the agent is not cytotoxic. In some embodiments, the agent is not cytotoxic in and of itself. In some embodiments, the agent does not induce antibody-directed cell cytotoxicity (ADCC). In some embodiments, the agent does not induce complement dependent cytotoxicity (CDC). In some embodiments, the agent does not comprise a cytotoxic moiety. In some embodiments, the agent does not induce apoptosis of a cell expressing HVEM upon binding of the HVEM expressed by the cell. In some embodiments, the agent does not induce apoptosis via interaction with another cell. In some embodiments, the agent does not directly induce killing of a cell expressing HVEM. In some embodiments, the agent does not target a cell for killing. In some embodiments, the agent does induce indirect apoptosis. In some embodiments, indirect apoptosis is apoptosis induced by downstream signaling through the HVEM receptor that leads to apoptosis. In some embodiments, indirect apoptosis is apoptosis that requires signal transduction. In some embodiments, indirect apoptosis is apoptosis that does not require the involvement of a second cell. In some embodiments, the agent does not induce apoptosis in an immune cell. In some embodiments, the agent induces apoptosis in a cancer cell.

In some embodiments, the agent inhibits interaction between HVEM and CD160. In some embodiments, the agent inhibits interaction between HVEM and LTα. In some embodiments, the agent inhibits interaction between HVEM and herpes simplex virus type 1 glycoprotein D (HSV1-gD). In some embodiments, the agent inhibits interaction between HVEM and at least two of CD160, HSV1-gD and LTα. In some embodiments, the agent blocks interaction between HVEM and CD160. In some embodiments, the agent blocks interaction between HVEM and LTα. In some embodiments, the agent blocks interaction between HVEM and HSV1-gD. In some embodiments, the agent blocks interaction between HVEM and at least two of CD160, HSV1-gD and LTα. In some embodiments, the agent inhibits/blocks interaction between HVEM and all of CD160, HSV1-gD and LTα. In some embodiments, the agent does not inhibit or block interaction between HVEM and at least one of CD160, HSV1-gD and LTα.

In some embodiments, the agent is an antibody or antigen binding fragment thereof. In some embodiments, the antibody or fragment thereof is a fab fragment. In some embodiments, the antibody or fragment thereof is a single chain antibody (scFv). In some embodiments, the antibody or fragment thereof is a single domain antibody. In some embodiments, the antibody is a human antibody. In some embodiments, the antibody is a humanized antibody. In some embodiments, the antibody is a monoclonal antibody. In some embodiments, the antibody is a blocking antibody.

As used herein, the term "antibody" refers to a polypeptide or group of polypeptides that include at least one binding domain that is formed from the folding of polypeptide chains having three-dimensional binding spaces with internal surface shapes and charge distributions complementary to the features of an antigenic determinant of an antigen. An antibody typically has a tetrameric form, comprising two identical pairs of polypeptide chains, each pair having one "light" and one "heavy" chain. The variable regions of each light/heavy chain pair form an antibody binding site. An antibody may be oligoclonal, polyclonal, monoclonal, chimeric, camelised, CDR-grafted, multi-specific, bi-specific, catalytic, humanized, fully human, anti-idiotypic and antibodies that can be labeled in soluble or bound form as well as fragments, including epitope-binding fragments, variants or derivatives thereof, either alone or in combination with other amino acid sequences. An antibody may be from any species. The term antibody also includes binding fragments, including, but not limited to Fv, Fab, Fab', F(ab')2 single stranded antibody (svFC), dimeric variable region (Diabody) and disulphide-linked variable region (dsFv). In particular, antibodies include immunoglobulin molecules and immunologically active fragments of immunoglobulin molecules, i.e., molecules that contain an antigen binding site. Antibody fragments may or may not be fused to another immunoglobulin domain including but not limited to, an Fc region or fragment thereof. The skilled artisan will further appreciate that other fusion products may be generated including but not limited to, scFv-Fc fusions, variable region (e.g., VL and VH)~Fc fusions and scFv-scFv-Fc fusions.

Immunoglobulin molecules can be of any type (e.g., IgG, IgE, IgM, IgD, IgA and IgY), class (e.g., IgG1, IgG2, IgG3, IgG4, IgA1 and IgA2) or subclass. In some embodiments, the antibody comprises IgG2 or IgG4. In some embodiments, the antibody comprises IgG2. In some embodiments, the antibody comprises IgG4. In some embodiments, the antibody comprises IgG1. In some embodiments, the antibody comprises IgG3. In some embodiments, the antibody comprises a modified IgG1 or IgG3 with reduced toxicity.

The basic unit of the naturally occurring antibody structure is a heterotetrameric glycoprotein complex of about 150,000 Daltons, composed of two identical light (L) chains and two identical heavy (H) chains, linked together by both noncovalent associations and by disulfide bonds. Each heavy and light chain also has regularly spaced intra-chain disulfide bridges. Five human antibody classes (IgG, IgA, IgM, IgD and IgE) exist, and within these classes, various subclasses, are recognized based on structural differences, such as the number of immunoglobulin units in a single antibody molecule, the disulfide bridge structure of the individual units, and differences in chain length and sequence. The class and subclass of an antibody is its isotype.

The amino terminal regions of the heavy and light chains are more diverse in sequence than the carboxy terminal regions, and hence are termed the variable domains. This part of the antibody structure confers the antigen-binding specificity of the antibody. A heavy variable (VH) domain and a light variable (VL) domain together form a single antigen-binding site, thus, the basic immunoglobulin unit has two antigen-binding sites. Particular amino acid residues are believed to form an interface between the light and heavy chain variable domains (Chothia et al., J. Mol. Biol. 186, 651-63 (1985); Novotny and Haber, (1985) Proc. Natl. Acad. Sci. USA 82 4592-4596).

The carboxy terminal portion of the heavy and light chains form the constant domains i.e. CH1, CH2, CH3, CL. While there is much less diversity in these domains, there are differences from one animal species to another, and further, within the same individual there are several different isotypes of antibody, each having a different function.

The term "framework region" or "FR" refers to the amino acid residues in the variable domain of an antibody, which are other than the hypervariable region amino acid residues as herein defined. The term "hypervariable region" as used herein refers to the amino acid residues in the variable domain of an antibody, which are responsible for antigen binding. The hypervariable region comprises amino acid residues from a "complementarity determining region" or "CDR". The CDRs are primarily responsible for binding to an epitope of an antigen. The extent of FRs and CDRs has been precisely defined (see, Kabat et al.).

Immunoglobulin variable domains can also be analyzed using the IMGT information system (www.//imgt.cines.fr/) (IMGT®/V-Quest) to identify variable region segments, including CDRs. See, e.g., Brochet, X. et al, Nucl. Acids Res. J6:W503-508 (2008).

As used herein, the term "humanized antibody" refers to an antibody from a non-human species whose protein sequences have been modified to increase similarity to human antibodies. A humanized antibody may be produced by production of recombinant DNA coding for the CDRs of the non-human antibody surrounded by sequences that resemble a human antibody. In some embodiments, the humanized antibody is a chimeric antibody. In some embodiments, humanizing comprises insertion of the CDRs of the invention into a human antibody scaffold or backbone. Humanized antibodies are well known in the art and any method of producing them that retains the CDRs of the invention may be employed.

The term "monoclonal antibody" or "mAb" as used herein refers to an antibody obtained from a population of substantially homogeneous antibodies, i.e., the individual antibodies comprising the population are identical and/or bind the same epitope, except for possible variants that may arise during production of the monoclonal antibody, such variants generally being present in minor amounts. In contrast to polyclonal antibody preparations that typically include different antibodies directed against different determinants (epitopes), each monoclonal antibody is directed against a single determinant on the antigen. In addition to their specificity, the monoclonal antibodies are advantageous in that they are uncontaminated by other immunoglobulins. The modifier "monoclonal" indicates the character of the antibody as being obtained from a substantially homogeneous population of antibodies and is not to be construed as produced by any specific preparation method. Monoclonal antibodies to be used in accordance with the methods provided herein, may be made by the hybridoma method first described by Kohler et al, Nature 256:495 (1975), or may be made by recombinant DNA methods (see, e.g., U.S. Pat. No. 4,816,567). The "monoclonal antibodies" may also be isolated from phage antibody libraries using the techniques described in Clackson et al, Nature 352:624-628 (1991) and Marks et al, J. Mol. Biol. 222:581-597 (1991), for example.

The mAb of the present invention may be of any immunoglobulin class including IgG, IgM, IgD, IgE or IgA. A hybridoma producing a mAb may be cultivated in vitro or in vivo. High titers of mAbs can be obtained in vivo production where cells from the individual hybridomas are injected intraperitoneally into pristine-primed Balb/c mice to produce ascites fluid containing high concentrations of the desired mAbs. mAbs of isotype IgM or IgG may be purified from such ascites fluids, or from culture supernatants, using column chromatography methods well known to those of skill in the art.

"Antibody fragments" comprise a portion of an intact antibody, preferably comprising the antigen binding region thereof. Examples of antibody fragments include Fab, Fab', F(ab')2, and Fv fragments; diabodies; tandem diabodies (taDb), linear antibodies (e.g., U.S. Pat. No. 5,641,870, Example 2; Zapata et al, Protein Eng. 8(10): 1057-1062 (1995)); one-armed antibodies, single variable domain antibodies, minibodies, single-chain antibody molecules; multispecific antibodies formed from antibody fragments (e.g., including but not limited to, db-Fc, taDb-Fc, taDb-CH3, (scFV)4-Fc, di-scFv, bi-scFv, or tandem (di,tri)-scFv); and Bi-specific T-cell engagers (BiTEs).

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-binding sites and is still capable of cross-linking antigen.

"Fv" is the minimum antibody fragment that contains a complete antigen-recognition and antigen-binding site. This region consists of a dimer of one heavy chain and one light chain variable domain in tight, non-covalent association. It is in this configuration that the three surfaces of the VH-VL dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear at least one free thiol group. F(ab')2 antibody fragments originally were produced as pairs of Fab' fragments that have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains.

Depending on the amino acid sequence of the constant domain of their heavy chains, antibodies can be assigned to different classes. There are five major classes of intact antibodies: IgA, IgD, IgE, IgG, and IgM, and several of these may be further divided into subclasses (isotypes), e.g., IgG1, IgG2, IgG3, IgG4, IgA, and IgA2. The heavy chain constant domains that correspond to the different classes of antibodies are called a, delta, e, gamma, and micro, respectively. The subunit structures and three-dimensional configurations of different classes of immunoglobulins are well known.

"Single-chain Fv" or "scFv" antibody fragments comprise the VH and VL domains of antibody, wherein these domains are present in a single polypeptide chain. In some embodiments, the Fv polypeptide further comprises a polypeptide linker between the VH and VL domains that enables the scFv to form the desired structure for antigen binding. For a review of scFv see Pluckthun in The Pharmacology of Monoclonal Antibodies, vol. 113, Rosenburg and Moore eds., Springer-Verlag, New York, pp. 269-315 (1994).

The term "diabodies" refers to small antibody fragments with two antigen-binding sites, which fragments comprise a heavy chain variable domain (VH) connected to a light chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies production is known in the art and is described in Natl. Acad. Sci. USA, 90:6444-6448 (1993).

The monoclonal antibodies of the invention may be prepared using methods well known in the art. Examples include various techniques, such as those in Kohler, G. and Milstein, C, Nature 256: 495-497 (1975); Kozbor et al, Immunology Today 4: 72 (1983); Cole et al, pg. 77-96 in MONOCLONAL ANTIBODIES AND CANCER THERAPY, Alan R. Liss, Inc. (1985).

Besides the conventional method of raising antibodies in vivo, antibodies can be generated in vitro using phage display technology. Such a production of recombinant antibodies is much faster compared to conventional antibody production and they can be generated against an enormous number of antigens. Furthermore, when using the conventional method, many antigens prove to be non-immunogenic or extremely toxic, and therefore cannot be used to generate antibodies in animals. Moreover, affinity maturation (i.e., increasing the affinity and specificity) of recombinant antibodies is very simple and relatively fast. Finally, large numbers of different antibodies against a specific antigen can be generated in one selection procedure. To generate recombinant monoclonal antibodies, one can use various methods all based on display libraries to generate a large pool of antibodies with different antigen recognition sites. Such a library can be made in several ways: One can generate a synthetic repertoire by cloning synthetic CDR3 regions in a pool of heavy chain germline genes and thus generating a large antibody repertoire, from which recombinant antibody fragments with various specificities can be selected. One can use the lymphocyte pool of humans as starting material for the construction of an antibody library. It is possible to construct naive repertoires of human IgM antibodies and thus create a human library of large diversity. This method has been widely used successfully to select a large number of antibodies against different antigens. Protocols for bacteriophage library construction and selection of recombinant antibodies are provided in the well-known reference text Current Protocols in Immunology, Colligan et al (Eds.), John Wiley & Sons, Inc. (1992-2000), Chapter 17, Section 17.1.

Non-human antibodies may be humanized by any methods known in the art. In one method, the non-human complementarity determining regions (CDRs) are inserted into a human antibody or consensus antibody framework sequence. Further changes can then be introduced into the antibody framework to modulate affinity or immunogenicity.

In some embodiments, antibodies and portions thereof include but are not limited to: antibodies, fragments of antibodies, Fab and F(ab')2, single-domain antigen-binding recombinant fragments and natural nanobodies. In some embodiments, the antigen binding fragment is selected from the group consisting of a Fv, Fab, F(ab')$_2$, scFv, scFv$_2$ or a scFv$_4$ fragment.

In some embodiments, the present invention provides nucleic acid sequences encoding the antibodies or antigen binding portions of the present invention.

For example, the polynucleotide may encode an entire immunoglobulin molecule chain, such as a light chain or a heavy chain. A complete heavy chain includes not only a heavy chain variable region (VH) but also a heavy chain constant region (CH), which typically will comprise three constant domains: CH1, CH2 and CH3; and a "hinge" region. In some situations, the presence of a constant region is desirable.

Other polypeptides which may be encoded by the polynucleotide include antigen-binding antibody fragments such as single domain antibodies ("dAbs"), Fv, scFv, Fab' and CHI and CK or CL domain has been excised. As minibodies are smaller than conventional antibodies they should achieve better tissue penetration in clinical/diagnostic use but being bivalent they should retain higher binding affinity than monovalent antibody fragments, such as dAbs. Accordingly, unless the context dictates otherwise, the term "antibody" as used herein encompasses not only whole antibody molecules, but also antigen-binding antibody fragments of the type discussed above. Each framework region present in the encoded polypeptide may comprise at least one amino acid substitution relative to the corresponding human acceptor framework. Thus, for example, the framework regions may comprise, in total, three, four, five, six, seven, eight, nine, ten, eleven, twelve, thirteen, fourteen, or fifteen amino acid substitutions relative to the acceptor framework regions. Given the properties of the individual amino acids comprising the disclosed protein products, some rational substitutions will be recognized by the skilled worker. Amino acid substitutions, i.e. "conservative substitutions," may be made, for instance, on the basis of similarity in polarity, charge, solubility, hydrophobicity, hydrophilicity, and/or the amphipathic nature of the residues involved.

Suitably, the polynucleotides described herein may be isolated and/or purified. In some embodiments, the polynucleotides are isolated polynucleotides.

As used herein, the term "non-naturally occurring" substance, composition, entity, and/or any combination of substances, compositions, or entities, or any grammatical variants thereof, is a conditional term that explicitly excludes, but only excludes, those forms of the substance, composition, entity, and/or any combination of substances, compositions, or entities that are well-understood by persons of ordinary skill in the art as being "naturally-occurring," or that are, or might be at any time, determined or interpreted by a judge or an administrative or judicial body to be, "naturally-occurring".

In some embodiments, the antibody comprises an IgG4. In some embodiments, the antibody comprises an IgG2. In some embodiments, the antibody comprises an IgG2 or an IgG4. In some embodiments, the antibody comprises an IgG1, IgG2, IgG3 or IgG4. In some embodiments, the antibody does not comprise an IgG1. In some embodiments, the antibody does not comprise an IgG3. In some embodiments, the antibody does not comprise an IgG1 or IgG3. In some embodiments, the antibody comprises a mutated IgG1 and/or IgG3, wherein the mutation inhibits induction of ADCC, CDC or both. In some embodiments, the mutation is in the FcRgamma binding motif.

In some embodiments, the antibody or antigen binding fragment thereof comprises three heavy chain CDRs (CDR-H) and three light chain CDRs (CDR-L), wherein: CDR-H1 comprises the amino acid sequence set forth in SEQ ID NO: 1 (SYAMS), CDR-H2 comprises the amino acid sequence as set forth in SEQ ID NO: 2 (AISGSGGSTYYADSVKG), CDR-H3 comprises the amino acid sequence as set forth in SEQ ID NO: 3 (APGDYTAYFDY), CDR-L1 comprises the amino acid sequence as set forth in SEQ ID NO: 4 (RASQSVSSYLA), CDR-L2 comprises the amino acid sequence as set forth in SEQ ID NO: 5 (GASSRAT), and CDR-L3 comprises the amino acid sequence as set forth in SEQ ID NO: 6 (QQYGSSPPYT). In some embodiments, the CDRs are according to the KABAT numbering system.

By another aspect, there is provided an antibody or antigen binding fragment thereof comprises three heavy chain CDRs (CDR-H) and three light chain CDRs (CDR-L), wherein: CDR-H1 comprises the amino acid sequence set forth in SEQ ID NO: 1 (SYAMS), CDR-H2 comprises the amino acid sequence as set forth in SEQ ID NO: 2 (AIS-GSGGSTYYADSVKG), CDR-H3 comprises the amino acid sequence as set forth in SEQ ID NO: 3 (APGDYTAY-FDY), CDR-L1 comprises the amino acid sequence as set forth in SEQ ID NO: 4 (RASQSVSSYLA), CDR-L2 comprises the amino acid sequence as set forth in SEQ ID NO: 5 (GASSRAT), and CDR-L3 comprises the amino acid sequence as set forth in SEQ ID NO: 6 (QQYGSSPPYT). In some embodiments, the CDRs are according to the KABAT numbering system.

In some embodiments, the antibody or antigen binding fragment thereof comprises three heavy chain CDRs (CDR-H) and three light chain CDRs (CDR-L), wherein: CDR-H1 comprises the amino acid sequence set forth in SEQ ID NO: 11 (GFTFSSYA), CDR-H2 comprises the amino acid sequence as set forth in SEQ ID NO: 12 (ISGSGGST), CDR-H3 comprises the amino acid sequence as set forth in SEQ ID NO: 13 (AKAPGDYTAYFDY), CDR-L1 comprises the amino acid sequence as set forth in SEQ ID NO: 14 (QSVSSY), CDR-L2 comprises the amino acid sequence as set forth in SEQ ID NO: 15 (GAS), and CDR-L3 comprises the amino acid sequence as set forth in SEQ ID NO: 16 (QQYGSSPPYT). In some embodiments, the CDRs are according to the IMGT numbering system.

By another aspect, there is provided an antibody or antigen binding fragment thereof comprises three heavy chain CDRs (CDR-H) and three light chain CDRs (CDR-L), wherein: CDR-H1 comprises the amino acid sequence set forth in SEQ ID NO: 11 (GFTFSSYA), CDR-H2 comprises the amino acid sequence as set forth in SEQ ID NO: 12 (ISGSGGST), CDR-H3 comprises the amino acid sequence as set forth in SEQ ID NO: 13 (AKAPGDYTAYFDY), CDR-L1 comprises the amino acid sequence as set forth in SEQ ID NO: 14 (QSVSSY), CDR-L2 comprises the amino acid sequence as set forth in SEQ ID NO: 15 (GAS), and CDR-L3 comprises the amino acid sequence as set forth in SEQ ID NO: 16 (QQYGSSPPYT). In some embodiments, the CDRs are according to the IMGT numbering system In some embodiments, the antibody comprises a heavy chain comprising the sequence QVQLVQSGG-GLVQPGGSLRLSCAASGFTFSSYAMSWVRQAPGK-GLEWVSAISGS GGSTYYADSVKGRFTISRDNSKNT-LYLQMNSLRAEDTAVYYCAKAPGDYTAYFD YWGQGTLVTVSS (SEQ ID NO: 7). In some embodiments, the heavy chain consists of the sequence of SEQ ID NO: 7. In some embodiments, the antibody comprises a heavy chain comprising the sequence MGWSCIILFL-VATATGVHSQVQLVQSGGGLVQPGGSLRLS-CAASGFTFSSYAMSW VRQAPGKGLEWVSAISGSGG-STYYADSVKGRFTISRDNSKNTLYLQMNSLRAEDT AVYYCAKAPGDYTAYFDYWGQGTLVTVSSAS-TKGPSVFPLAPCSRSTSESTAALG CLVKDYF-PEPVTVSWNSGALTSGVHTFPAVLQSSGLYS-LSSVVTVPSSSLGTKTYT CNVDHKPSNTKVDKRVESKYGPPCPPCPAPE-FLGGPSVFLFPPKPKDTLMISRTPEV TCVVVDVSQEDPEVQFNWYVDGVEVHNAKTKPRE-EQFNSTYRVVSVLTVLHQD WLNGKEYKCKVSNKGLPSSIEKTISKAKGQPREPQV YTLPPSQEEMTKNQVSLTCL VKGFYPSDIA-VEWESNGQPENNYKTTPPVLDSDGSFFLY-SRLTVDKSRWQEGNVF SCSVMHEALHN-HYTQKSLSLSLGK (SEQ ID NO: 9). In some embodiments, the heavy chain consists of the sequence of SEQ ID NO: 9.

In some embodiments, the antibody comprises a light chain comprising the sequence ELVLTQSPATLSLSPGER-ATLSCRASQSVSSYLAWYQQKPGQAPRLLIY-GASSRAT GIPDRFSGSGSGTDFTLTISRLEPED-FAVYYCQQYGSSPPYTFGQGTKVEIK (SEQ ID NO: 8). In some embodiments, the light chain consists of the sequence of SEQ ID NO: 8. In some embodiments, the antibody comprises a light chain comprising the sequence MGWSCIILFLVATATGVHSELVLTQSPATLSLSPGER-ATLSCRASQSVSSYLAWYQ QKPGQAPRLLIY-GASSRATGIPDRFSGSGSGTDFTLTISRLEPED-FAVYYCQQYGSS PPYTFGQGTKVEIKRTVAAPSVFIFPPSDEQLKSG-TASVVCLLNNFYPREAKVQWK VDNALQSGNSQESVTEQDSKDSTYSLSSTLTL-SKADYEKHKVYACEVTHQGLSSP VTKSFNRGEC (SEQ ID NO: 10). In some embodiments, the light chain consists of the sequence of SEQ ID NO: 10.

In some embodiments, the heavy chain and the light chain are joined by a linker. In some embodiments, the linker is an amino acid linker. In some embodiments, the linker is at most 1, 2, 3, 4, 5, 6, 7, 8, 9, 10, 12, 14, 15, 16, 18, 20, 22, 24 or 25 amino acids long. Each possibility represents a separate embodiment of the invention. In some embodiments, the linker is at least 1, 2, 3, 4, 5, 6, 7, 8, 9, 10, 12, 14, 15, 16, 18, 20, 22, 24 or 25 amino acids long. Each possibility represents a separate embodiment of the invention. In some embodiments, the linker is between 1-25, 5-25, 10-25, 15-25, 20-25, 1-20, 5-20, 10-20, 15-20, 1-15, 5-15, 10-15, 1-10, 5-10 or 1-5 amino acids long. Each possibility represents a separate embodiment of the invention.

By another aspect, there is provided a pharmaceutical composition comprising an agent of the invention.

In some embodiments, pharmaceutical composition further comprises a pharmaceutically acceptable carrier, excipient or adjuvant. In some embodiments, pharmaceutical composition a therapeutically effective amount of the agent of the invention.

As used herein, the term "carrier," "excipient," or "adjuvant" refers to any component of a pharmaceutical composition that is not the active agent. As used herein, the term "pharmaceutically acceptable carrier" refers to non-toxic, inert solid, semi-solid liquid filler, diluent, encapsulating material, formulation auxiliary of any type, or simply a sterile aqueous medium, such as saline. Some examples of the materials that can serve as pharmaceutically acceptable carriers are sugars, such as lactose, glucose and sucrose, starches such as corn starch and potato starch, cellulose and its derivatives such as sodium carboxymethyl cellulose, ethyl cellulose and cellulose acetate; powdered tragacanth; malt, gelatin, talc; excipients such as cocoa butter and suppository waxes; oils such as peanut oil, cottonseed oil, safflower oil, sesame oil, olive oil, corn oil and soybean oil; glycols, such as propylene glycol, polyols such as glycerin, sorbitol, mannitol and polyethylene glycol; esters such as ethyl oleate and ethyl laurate, agar; buffering agents such as magnesium hydroxide and aluminum hydroxide; alginic acid; pyrogen-free water; isotonic saline, Ringer's solution; ethyl alcohol and phosphate buffer solutions, as well as other non-toxic compatible substances used in pharmaceutical formulations. Some non-limiting examples of substances which can serve as a carrier herein include sugar, starch, cellulose and its derivatives, powered tragacanth, malt, gelatin, talc, stearic acid, magnesium stearate, calcium sulfate, vegetable oils, polyols, alginic acid, pyrogen-free water, isotonic saline, phosphate buffer solutions, cocoa butter (suppository base), emulsifier as well as other non-toxic pharmaceutically compatible substances used in other pharmaceutical formulations. Wetting agents and lubricants such as sodium lauryl sulfate, as well as coloring agents, flavoring agents, excipients, stabilizers, antioxidants, and preservatives may also be present. Any non-toxic, inert, and effective carrier may be used to formulate the compositions contemplated herein. Suitable pharmaceutically acceptable carriers, excipients, and diluents in this regard are well known to those of skill in the art, such as those described in The Merck Index, Thirteenth Edition, Budavari et al., Eds., Merck & Co., Inc., Rahway, N.J. (2001); the CTFA (Cosmetic, Toiletry, and Fragrance Association) International Cosmetic Ingredient Dictionary and Handbook, Tenth Edition (2004); and the "Inactive Ingredient Guide," U.S. Food and Drug Administration (FDA) Center for Drug Evaluation and Research (CDER) Office of Management, the contents of all of which are hereby incorporated by reference in their entirety. Examples of pharmaceutically acceptable excipients, carriers and diluents useful in the present compositions include distilled water, physiological saline, Ringer's solution, dextrose solution, Hank's solution, and DMSO. These additional inactive components, as well as effective formulations and administration procedures, are well known in the art and are described in standard textbooks, such as Goodman and Gillman's: The Pharmacological Bases of Therapeutics, 8th Ed., Gilman et al. Eds. Pergamon Press (1990); Remington's Pharmaceutical Sciences, 18th Ed., Mack Publishing Co., Easton, Pa. (1990); and Remington: The Science and Practice of Pharmacy, 21st Ed., Lippincott Williams & Wilkins, Philadelphia, Pa., (2005), each of which is incorporated by reference herein in its entirety. The presently described composition may also be contained in artificially created structures such as liposomes, ISCOMS, slow-releasing particles, and other vehicles which increase the half-life of the peptides or polypeptides in serum. Liposomes include emulsions, foams, micelles, insoluble monolayers, liquid crystals, phospholipid dispersions, lamellar layers and the like. Liposomes for use with the presently described peptides are formed from standard vesicle-forming lipids which generally include neutral and negatively charged phospholipids and a sterol, such as cholesterol. The selection of lipids is generally determined by considerations such as liposome size and stability in the blood. A variety of methods are available for preparing liposomes as reviewed, for example, by Coligan, J. E. et al, Current Protocols in Protein Science, 1999, John Wiley & Sons, Inc., New York, and see also U.S. Pat. Nos. 4,235,871, 4,501,728, 4,837,028, and 5,019,369.

The carrier may comprise, in total, from about 0.1% to about 99.99999% by weight of the pharmaceutical compositions presented herein.

The term "therapeutically effective amount" refers to an amount of a drug effective to treat a disease or disorder in a mammal. In some embodiments, a therapeutically effective amount is an amount effective, at dosages and for periods of time necessary, to achieve the desired therapeutic or prophylactic result. The exact dosage form and regimen would be determined by the physician according to the patient's condition.

In some embodiments, the agent is for use in treating a disease or condition. In some embodiments, the pharmaceutical composition is for use in treating a disease or condition. In some embodiments, the disease or condition is characterized by cells expressing HVEM. In some embodiments, the cell are disease cells characterized by expressing HVEM. In some embodiments, the cells are characterized by over-expressing HVEM. In some embodiments, overexpression is as compared to a healthy cell. In some embodiments, a healthy cell is a non-diseased cell. In some embodiments, overexpression is an increased expression. In some embodiments, the disease or condition is an HVEM positive disease or condition. In some embodiments, the disease or condition is a BTLA positive disease or condition.

In some embodiments, the disease or condition is an HVEM positive cancer. In some embodiments, the disease or condition is a BTLA positive cancer. In some embodiments, the disease or condition is an HVEM positive pre-cancerous lesion. In some embodiments, the cancer is melanoma. In some embodiments, the cancer is renal cell carcinoma. In some embodiments, the cancer is selected from melanoma, renal cancer, cervical cancer, prostate cancer, pancreatic cancer, lung cancer, ovarian cancer, colon cancer, breast cancer and head and neck cancer. In some embodiments, the renal cancer is renal cell carcinoma. A skilled artisan will appreciate that any cancer that expresses HVEM may be a therapeutic target. In some embodiments, the disease is an infectious disease. In some embodiments, the cells of the infection comprise HVEM expression. In some embodiments, an infected cell comprises HVEM expression. In some embodiments, the infectious disease is a bacterium and a bacterial cell comprises HVEM expression. In some embodiments, the infectious disease is a fungal infection and a fungal cell comprises HVEM expression. In some embodiments, the infectious disease is a virus and a virally infected subject cell comprises HVEM expression. In some embodiments, the virus is Herpes virus. In some embodiments, HVEM expression is HVEM overexpression. In some embodiments, HVEM expression is increased HVEM expression.

By another aspect, there is provided a method of treating an HVEM positive disease or condition, the method comprising inhibiting HVEM and BTLA interaction and activating HVEM signaling in an immune cell a disease cell or both.

In some embodiments, the method comprises administering the agent of the invention. In some embodiments, the method comprises administering the pharmaceutical composition of the invention.

By another aspect, there is provided a method of treating an HVEM positive disease or condition, the method comprising administering an agent of the invention.

By another aspect, there is provided a method of treating an HVEM positive disease or condition, the method comprising administering a pharmaceutical composition of the invention.

In some embodiments, the method further comprises not inhibiting HVEM-TNFSF14 interaction. In some embodiments, the method further comprises not substantially inhibiting HVEM-TNF SF14 interaction.

In some embodiments, the method further comprises inhibiting interaction between PD-1 and one of its ligands. In some embodiments, a PD-1 ligand is selected from PD-L1 and PD-L2. In some embodiments, the method further comprises inhibiting PD-1, PD-L1 or PD-L2. In some embodiments, the method further comprises inhibiting PD-1 to PD-L1 interaction. In some embodiments, the method further comprises inhibiting PD-1 to PD-L2 interaction. In some embodiments, the method further comprises inhibiting PD-1 to PD-L1 or PD-L2 interaction. In some embodiments, inhibiting interaction comprises administering an agent that inhibits PD-1 to PD-L1 interaction or PD-1 to PD-L2 interaction. In some embodiments, inhibiting interaction comprises administering an agent that inhibits interaction between PD-1 and at least one of its ligands. In some embodiments, at least one ligand is two ligands. In some embodiments, inhibiting interaction comprises PD-1/PD-L1 blockade. In some embodiments, inhibiting interaction comprises PD-1/PD-L1 or PD-L2 blockade. In some embodiments, inhibiting interaction comprises anti-PD-1/PD-L1 therapy. In some embodiments, inhibiting interaction comprises anti-PD-1/PD-L1 or PD-L2 therapy. In some embodiments, therapy is immunotherapy. In some embodiments, an agent that inhibits interaction is an anti-PD-1 or anti-PD-L1 antibody. In some embodiments, an agent that inhibits interaction is an anti-PD-1, anti-PD-L1 or anti-PD-L2 antibody. In some embodiments, an agent that inhibits interaction is a PD-1/PD-L1 inhibitor. In some embodiments, an agent that inhibits interaction is a PD-1/PD-L1/PD-L2 inhibitor. In some embodiments, the antibody is a blocking antibody. PD-L1/L2 and PD-1 therapies are well known in the art and include but are not limited to nivolumab (Opdivo), pembrolizumab (Keytruda), atezolizumab, avelumab, durvalumab, cemiplimab (Libtayo), pidilizumab, AMP-224, AMP-514 and PDR001.

In some embodiments, the method of treatment further comprises administering another therapeutic against the HVEM-expressing cell. In some embodiments, the other therapeutic is an anti-cancer therapeutic. In some embodiments, the therapeutic is a non-autologous immune cell. In some embodiments, the other therapeutic is an autologous immune cell. In some embodiments, the immune cell is a CAR expression immune cell. In some embodiments, the CAR is a CAR-T. In some embodiments, the CAR is a CAR-NK. In some embodiments, the autologous immune cell is TIL therapy. In some embodiments, the non-autologous immune cell is an adoptive cell therapy. In some embodiments, the autologous immune cell is an adoptive cell therapy. In some embodiments, the adoptive cell is a CAR cell. In some embodiments, the adoptive cell is a TIL.

In some embodiments, the composition of the invention and the another therapeutic are administering concomitantly. In some embodiments, the composition of the invention is administered before, after or at the same time as the another therapeutic.

By another aspect, there is provided a method of determining suitability of a subject to be treated by a method of the invention, the method comprising obtaining a sample from the subject and determining HVEM levels in the sample, wherein positive expression of HVEM indicates the subject is suitable for a method of treatment of the invention.

By another aspect, there is provide a method of detecting HVEM in a sample, the method comprising contacting the sample with an agent of the invention, or an antibody or antigen binding fragment thereof of the invention, thereby detecting HVEM.

In some embodiments, the contacting is under conditions suitable for binding of the agent or antibody or antigen binding fragment thereof to bind to HVEM. In some embodiments, the conditions are suitable for specific binding to HVEM. In some embodiments, binding is hybridizing. Conditions for antibody/agent binding will depend on the sample. A skilled artisan will appreciate the conditions needed for binding to a tissue sample (dependent on the method/type of fixation) are different than those of binding in a liquid solution, such as a whole cell lysate. Such binding conditions are well known in the art and a skilled artisan can select the proper conditions for a given sample.

In some embodiments, the sample is a tissue sample. In some embodiments, the sample is a paraffin embedded sample. In some embodiments, the sample is a perfused sample. In some embodiments, the sample is from a subject. In some embodiments, the sample is a healthy sample. In some embodiments, the sample is a diseased sample. In some embodiments, the sample is a diagnostic sample.

In some embodiments, the method further comprises detecting the agent of the invention, or an antibody or antigen binding fragment thereof of the invention. In some embodiments, the detection is immunohistochemical detection. In some embodiments, the detection is immunofluorescent detection. In some embodiments, the detection is FACS detection. In some embodiments, the detection further comprises contacting the sample with a secondary antibody that recognized the agent or antibody of the invention. In some embodiments, the detection comprises detecting the secondary antibody. In some embodiments, the detection comprises microscopy.

In some embodiments, the subject suffers from a disease or condition. In some embodiments, the subject is suspected to suffer from a disease or condition. In some embodiments, the subject is at risk of developing a disease or condition. In some embodiments, the subject suffers from a disease or condition which may comprise increased HVEM expression. In some embodiments, the subject suffers from a disease or condition which may be characterized by increased HVEM expression. In some embodiments, the subject suffers from cancer. In some embodiments, the cancer is a cancer that did not respond to first line therapy. In some embodiments, the cancer is a cancer relapse. In some embodiments, the cancer is a cancer that did not respond to PD-1/PD-L1 therapy.

In some embodiments, the sample is a disease sample. In some embodiments, the sample is a biological fluid. In some embodiments, the biological fluid is selected from blood, serum, plasma, urine, feces, bile, semen, tumor fluid, and cerebral spinal fluid. In some embodiments, the sample is a blood sample. In some embodiments, the sample is a cell sample. In some embodiments, the sample comprises cells. In some embodiments, the sample comprises disease cells. In some embodiments, the sample is a tumor sample. In some embodiments, the sample is a biopsy.

In some embodiments, positive expression of HVEM comprises HVEM expression. In some embodiments, positive expression of HVEM comprises elevated HVEM levels. In some embodiments, positive expression of HVEM comprises increased HVEM levels. In some embodiments, positive expression of HVEM comprises overexpression of HVEM. In some embodiments, positive expression of HVEM is as compared to healthy sample. In some embodiments, the healthy sample is from healthy tissue and/or cells adjacent to the disease tissue and/or cells. In some embodiments, a healthy sample comprises non-infected cells. In some embodiments, a healthy sample is for a healthy donor. In some embodiments, positive expression of HVEM is as compared to a predetermined threshold.

By another aspect, there is provided a kit comprising a pharmaceutical composition of the invention, or an agent of the invention.

In some embodiments, the kit further comprises a PD-1 based therapy. In some embodiments, the kit further comprises a PD-L1 based therapy. In some embodiments, the therapy is an immunotherapy. In some embodiments, the therapy is an anti-PD-1 therapy. In some embodiments, the therapy is an anti-PD-L1 therapy. In some embodiments, therapy is a PD-1/PD-L1 blockade therapy. In some embodiments, the therapy is a blocking antibody. In some embodiments, the therapy is an anti-PD-1 antibody. In some embodiments, the therapy is an anti-PD-L1 antibody. In some embodiments, the antibody is a blocking antibody.

In some embodiments, the kit further comprises a label stating the pharmaceutical composition of the invention is for use with a PD-1 and/or PD-L1 based therapy. In some embodiments, the kit further comprises a label stating the agent of the invention is for use with a PD-1 and/or PD-L1 based therapy.

In some embodiments, the kit further comprises a secondary detection molecule. In some embodiments, the detection molecule is for detection an agent of the invention. In some embodiments, the secondary detection molecule is an antibody that binds to an agent of the invention. In some embodiments, the detection molecule comprises a detectable moiety. Examples of detectable moieties include, but are not limited to a fluorescent moiety, a tag, a radiolabel, a dye and a chemiluminescent moiety. In some embodiments, the detectable moiety is a fluorescent moiety. Examples of fluorescent moieties include, but are not limited to GFP, RFP, YFP, APC, CY5, CY7, and Pacific Blue. Secondary detection molecules are well known in the art and any such molecule that will detect an agent of the invention may be used.

As used herein, the term "about" when combined with a value refers to plus and minus 10% of the reference value. For example, a length of about 1000 nanometers (nm) refers to a length of 1000 nm+−100 nm.

It is noted that as used herein and in the appended claims, the singular forms "a," "an," and "the" include plural referents unless the context clearly dictates otherwise. Thus, for example, reference to "a polynucleotide" includes a plurality of such polynucleotides and reference to "the polypeptide" includes reference to one or more polypeptides and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

In those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

Various embodiments and aspects of the present invention as delineated hereinabove and as claimed in the claims section below find experimental support in the following examples.

EXAMPLES

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Strategies for Protein Purification and Characterization—A Laboratory Course Manual" CSHL Press (1996); all of which are incorporated by reference. Other general references are provided throughout this document.

Materials and Methods

Generation of scFv against HVEM by phage display: Naïve human scFv library was incubated with synthetic/recombinant tags in order to subtract tag specific clones and with control CHO-K1 empty cells in order to subtract CHO-K1 cell binding clones. Then, phages were subjected to three biopanning rounds through incubation with CHO-K1 cells overexpressing hrHVEM. Clones were picked, rescued with the help of helper-phage and screened by phage ELISA against hrHVEM, mrHVEM and crHVEM. Clones were sequenced and positive unique clones were sub-cloned into pET25b protein expression vector. Lysates were prepared from 200 ml of induced culture. Bacterial cells were pelleted, washed with PBS and lysed by French press. Insoluble debris was removed by high-speed centrifugation and the lysate containing the soluble proteins, including the scFvs, was collected. The scFvs were cloned with HIS tags.

Generation of transfected CHO-K1 cells: CHO-K1 cells were seeded in 6-well plates at a density of 200K cells/well in Nutrient Mixture F-12 (Ham's) with L-glutamine media (Biological Industries, Israel) supplemented with 10% FBS (Biological Industries, Israel) and incubated overnight at 37° C. Following incubation, 2 µg plasmid DNA was transfected using 4 µl jetPRIME transfection reagent (Polyplus-transfection, France), according to manufacturer's instructions. Selection with 1 mg/ml G418 Sulfate antibiotics (Millipore, Germany) was performed two days post-transfection and cells were routinely cultured with addition of antibiotics.

Flow cytometry: Surface cell staining was performed on ≤1×10⁵ cells with the appropriate pure specific antibody diluted in FACS buffer (PBS, 0.02% sodium azide, 0.5% BSA) on ice for 30 minutes. Following incubation, cells were centrifuged for 5 minutes in 500 g at 4° C. and supernatant was removed. Cells were incubated for 30 minutes covered on ice with fluorophore-conjugated appropriate secondary antibody. In case of fluorophore-conjugated-primary antibody, direct staining was performed with no secondary antibody. Following incubation, cells were washed and re-suspended in 200 µl FACS buffer for flow cytometry analysis.

Mab Production:

a. Luciferase reporter assay: Luciferase activity was measured using Bright-Glo Luciferase Assay System (Promega, USA), according to manufacturer's instructions. Briefly, Luciferase Assay Reagent was prepared by combining and mixing one bottle of Buffer and one bottle of Substrate. Equal volumes of reagent and sample were mixed, and luminescence was measured 3 or 10 minutes after addition of reagent using appropriate instrument settings.

b. Plasmids Preparation: scFv2 was converted into full IgG4 antibody containing S228P mutation. Target DNA sequence was designed, optimized and synthesized. The complete sequence was sub-cloned into pcDNA3.4 vector. Transfection grade plasmid was maxi-prepared for Expi293F cell expression.

c. Cell Culture and Transient Transfection: Expi293F cells were grown in serum-free Expi293F™ Expression Medium (Thermo Fisher Scientific, USA). The cells were maintained in Erlenmeyer Flasks (Corning Inc., USA) at 37° C. with 8% CO2 on an orbital shaker (VWR Scientific, USA). One day before transfection, the cells were seeded at an appropriate density in Corning Erlenmeyer Flasks. On the day of transfection, DNA and transfection reagent were mixed at an optimal ratio and then added into the flask with cells ready for transfection. The recombinant plasmids encoding target protein was transiently transfected into suspension Expi293F cell cultures. The cell culture supernatant collected on day 6 post-transfection was used for purification.

Purification and Analysis: Cell culture broth was centrifuged and followed by filtration. Filtered cell culture supernatant was loaded onto an affinity purification column at an appropriate flowrate. After washing and elution with appropriate buffers, the eluted fractions were pooled, and buffer exchanged to final formulation buffer. The purified protein was analyzed by SDS-PAGE and Western blotting analysis for molecular weight and purity measurements. The concentration was determined by A280 method (antibody).

Cytotoxic assay: Nuclear RFP stained melanoma cells were seeded for overnight incubation to allow them to attach. Then, melanoma cells were pre-incubated with 20 µg/ml of the mAb of the invention or hIgG4 isotype control antibody (Invivogen, France) and TILs were pre-incubated with 20 µg/ml of anti-PD1 mAb (Nivolumab, BMS) or hIgG4 isotype control antibody (Invivogen, France). Pre-incubated TILs or medium only with anti-PD1 or hIgG4 isotype control mAb were added to the melanoma cells together with CellEvent Caspase-3/7 Green Detection Reagent (Invitrogen, USA). Plates were placed in the Incucyte ZOOM system (ESSEN Bioscience, USA) and scanned every hour. Caspase 3/7 positive events, reflecting specific killing of melanoma, were counted. Similar protocol was used for cytotoxic assay experiments with RCC cells and for cytotoxic assay experiment with MAB356.

T cell activation assay by flow cytometry: Melanoma cells or media only were incubated for 1 hour at 37° C. with 20 μg/ml mAb of the invention or hIgG4 isotype control antibody (Invivogen, France). After 1 hour, TILs were added to the melanoma cells or media and co-cultured for 4 hours at 37° C. After 4 hours, cells were surface stained with anti-CD3 (Biolegend, USA) and anti-41BB (Biolegend, USA) and expression was assessed by flow cytometry using CytoFLEX instrument (Beckman Coulter, USA) and data analysis was performed using FCS Express 6 software (DeNovo Software, US).

T cell activation assay by Incucyte ZOOM system: Nuclear RFP stained melanoma cells were seeded for overnight incubation to allow them to attach. After overnight incubation, melanoma cells were incubated for one-hour at 37° C. with 20 μg/ml mAb of the invention or hIgG4 isotype control. MART-1 electroporated PBMCs or medium were added to the melanoma cells together with anti-41BB (Biolegend, USA) labeled with FabFlour-488 labeling reagent (ESSEN Bioscience, USA). Plates were placed in the Incucyte ZOOM system and scanned every hour.

T cell cluster assay: Images were acquired by the Incucyte ZOOM system. The number of clusters was calculated through image analysis with image J version 1.52a. Images were smoothed, the contrast was enhanced and then transformed into 8-bit images. After image binarization the images were processed by applying the "close", "fill holes" and "erode" commands. The "analyze particles" command was then applied with the following parameters: size of 500 mm^2-infinity and Circularity between 0.1-1.

Example 1: Identification of HVEM as an Immunoblockade Target

A high-throughput genome-wide primary siRNA screen, consisting of ~8,300 genes, was run on 2 patient-derived melanoma cell systems. The effect on killing was assessed 96 hours post siRNA transfection by overnight co-culture with TILs, using an LDH-based cytotoxicity assay. Successful knockdown of positive control was assessed by FACS. A confirmatory screen, consisting of 360 genes, was validated on 8 melanoma cell systems using the same design as the primary screen, in which positive hits were defined based on their Z-score and percent of killing enhancement, corrected for the effect of the siRNA on proliferation. Finally, a validation screen, consisting of 54 genes, was performed on 5 melanoma cell systems. HVEM was discovered as a strong positive hit as a potential immunotherapeutic target.

Example 2: Selection of scFvs Against HVEM

Figure 1:
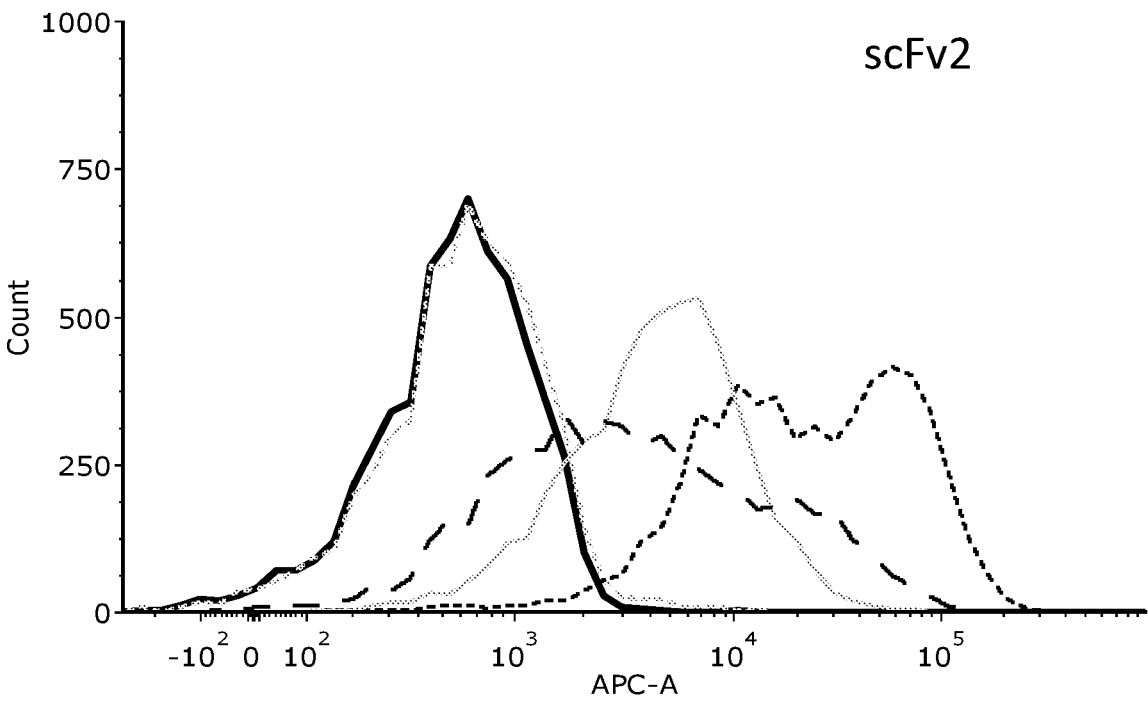
FIG. 1. Binding of lysates containing scFv to CHO-K1 cells overexpressing HVEM: CHO-K1 cells overexpressing
Figure 1:
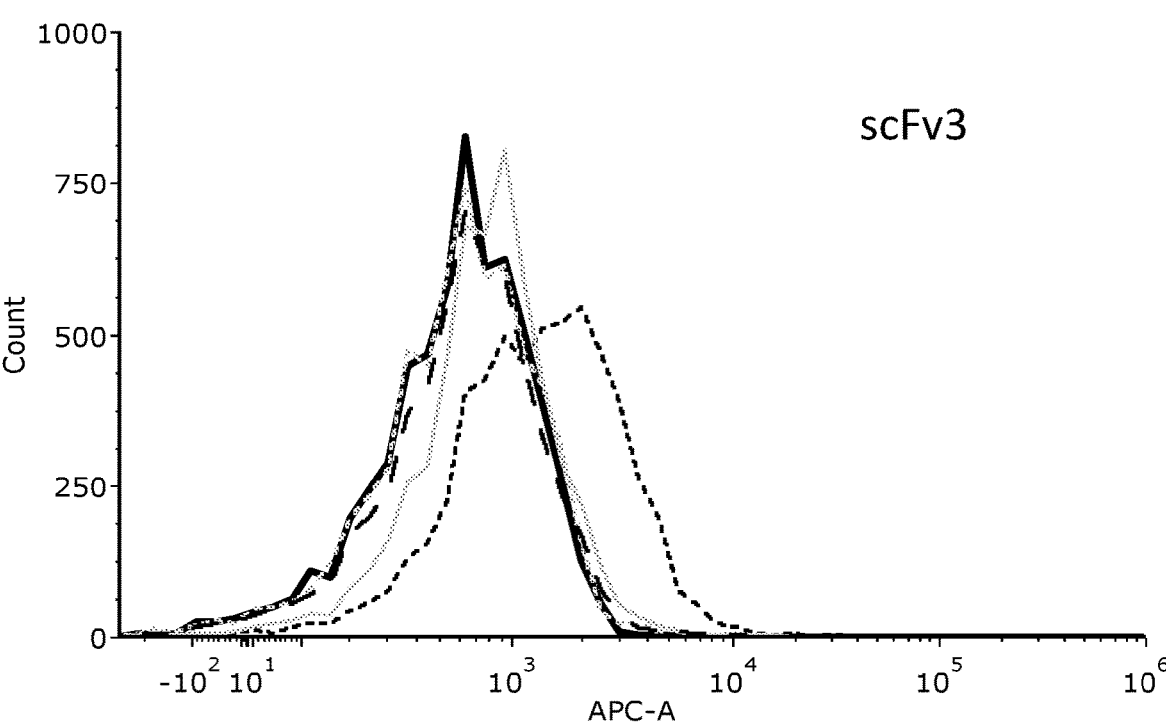
Figure 1:
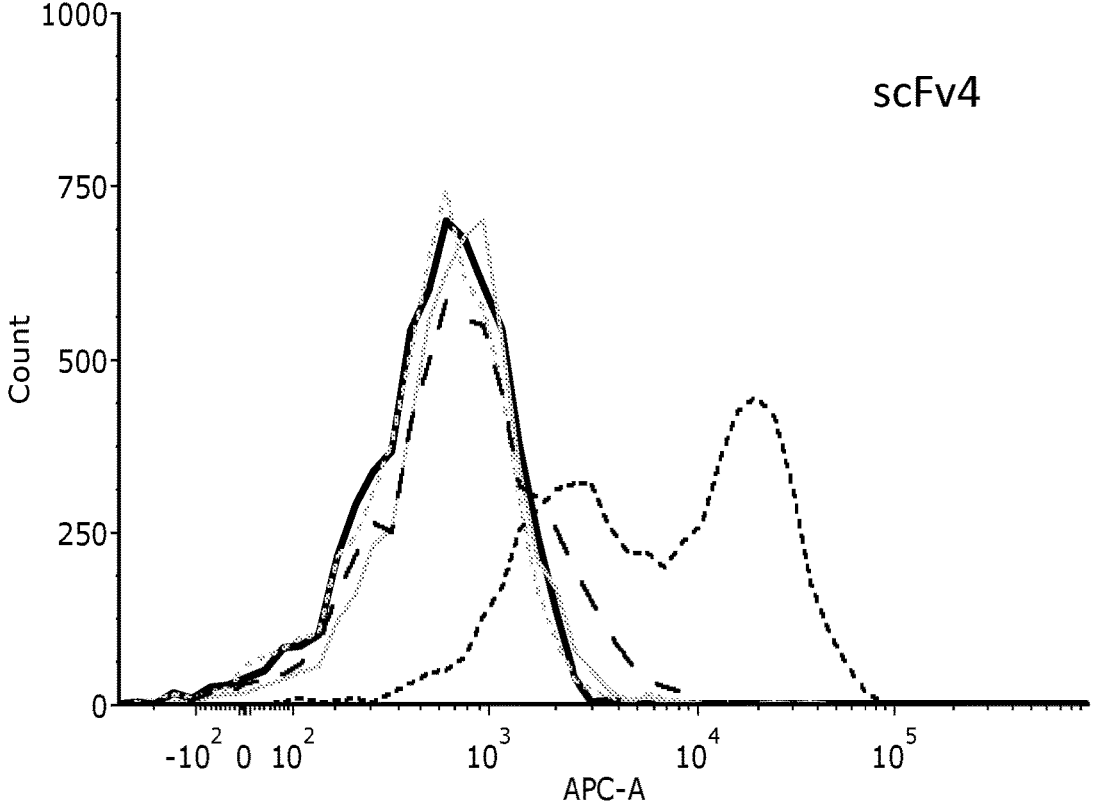
Figure 1:
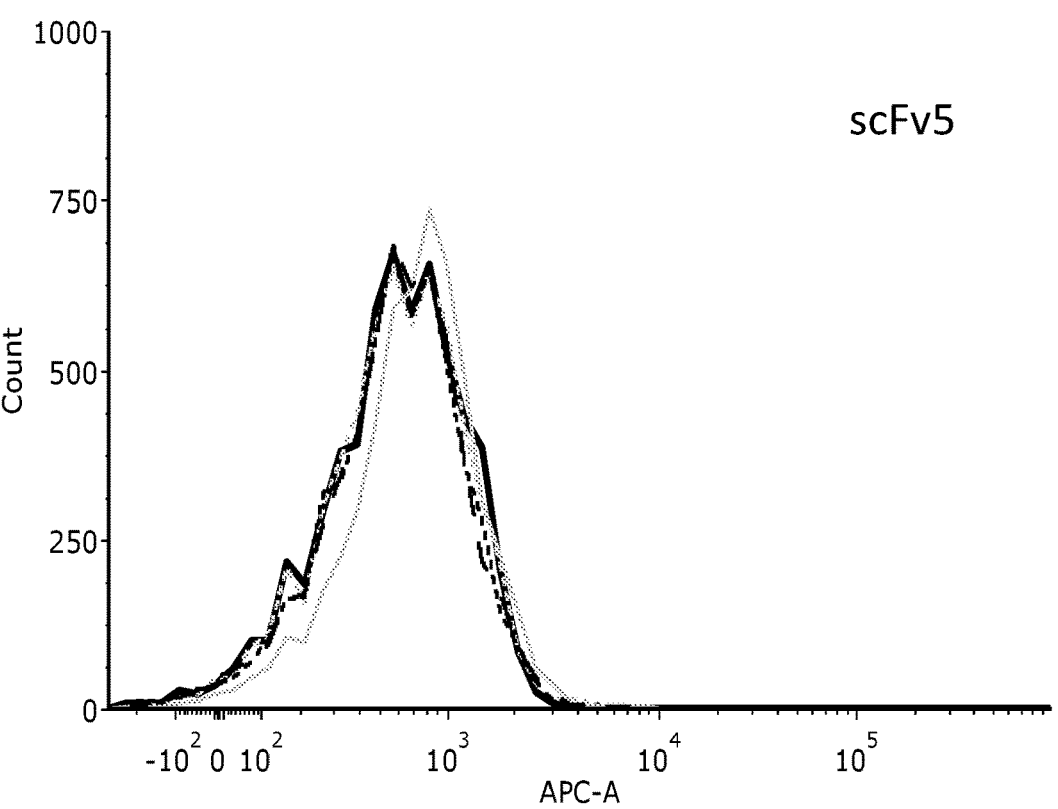
Figure 1:
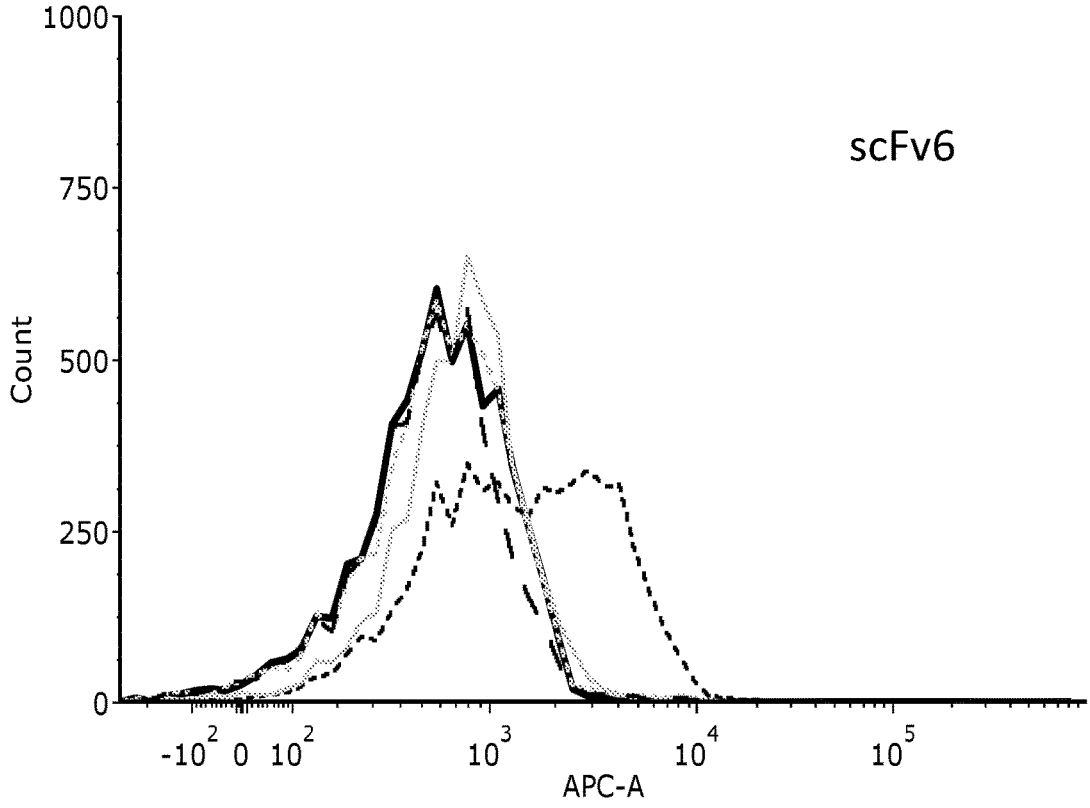

Having established HVEM as a potential target for therapeutic immunoblockade in the treatment of cancer, single chain antibody fragments (scFvs) that could bind HVEM were isolated and assayed. scFvs were isolated as described hereinabove (Materials and Methods). 6 selected scFvs were screened for binding to recombinant human, mouse and cynomolgus HVEM (see Table 1). Five of the six showed strong binding to human recombinant HVEM (hrHVEM) expressed in CHO-K1 cells as measured by cell ELISA. CHO-K1-empty cells were used as a negative control. Two of those five showed very strong binding to mouse recombinant HVEM (mrHVEM), while the other three displayed a much weaker binding. One of the five also showed strong binding to monkey (cynomolgus) HVEM, while three of the others showed a much weaker binding. FACS analysis was used to confirm these results. The scFvs contained a HIS tag and anti-HIS secondary APC-conjugated antibody was used for detection of surface binding. As predicted by ELISA, five of the scFvs were found to bind surface hrHVEM in CHO-K1 HVEM overexpressing cells, although two of the scFvs did so poorly (FIG. 1).

TABLE 1

| Cell ELISA with lysates containing scFv against CHO-K1 cells overexpressing HVEM. Numbers represent OD values. | | | | |
|---|---|---|---|---|
| Group | Control | Human | Mouse | Cynomolgus |
| 1 | 0.044 | 1.194 | 0.140 | 0.049 |
| 2 | 0.045 | 1.507 | 1.366 | 1.112 |
| 3 | 0.042 | 1.052 | 0.403 | 0.209 |
| 4 | 0.048 | 1.110 | 0.161 | 0.140 |
| 5 | 0.055 | 0.395 | 0.057 | 0.046 |
| 6 | 0.044 | 1.207 | 0.951 | 0.486 |

Next the scFvs were checked for their ability to inhibit interaction between HVEM and two of its ligands: BTLA and LIGHT (TNFSF14). ELISA plates were coated with 2.5 g/ml hrHVEM and incubated overnight at 4° C. Plates were then washed and blocked with 2% BSA for 1 hour at room temperature. scFv1-6 lysates and control lysate were added to the ELISA plates and incubated for 1 hour at room temperature. Plates were washed and blocked for 10 minutes followed by more washes. hrBTLA-Fc or hrLIGHT-HIS was added to the ELISA plates and incubated for 2 hours at room temperature. Plates were washed, blocked and incubated with mouse anti-BTLA biotin mAb or goat anti-LIGHT pAb for 1 hour at room temperature. Plates were washed and incubated for 30 minutes at room temperature with streptavidin peroxidase or bovine anti-goat HRP antibody. Finally, plates were washed and TMB followed by addition of sulfuric acid stop solution. Absorbance was read at 450 nM and 570 nM using Spark 10M plate-reader. Unexpectedly, though scFvs 1, 3, 4 and 6 had bound hrHVEM, these antibodies did not inhibit HVEM-BTLA binding. By contrast, scFv2 nearly completely inhibited BTLA binding (FIG. 2A). Notably, none of the antibodies significantly inhibited binding of LIGHT to HVEM (FIG. 2B). Due to its binding human, mouse and monkey rHVEM, and its ability to block HVEM-BTLA interaction, scFv2 was selected for all future work.

Example 3: Anti-HVEM IgG Antibody

Though the single-chain antibody scFv2 was effective at blocking HVEM-BTLA interaction, a full IgG monoclonal antibody (mAb) was designed from the scFv2 light and heavy chain, and specifically the CDRs. scFv2 was sequenced and the light and heavy chains were cloned into an IgG4 backbone barring the S228P mutation. The full sequence of the heavy chain of this mAb is presented in SEQ ID NO: 9 and the light chain is presented in SEQ ID NO: 10. The presence of a full IgG antibody was confirmed by SDS-PAGE and western blot (FIG. 3).

Next the binding of the new mAb to recombinant HVEM from human, mouse and monkey was assessed as before. Binding to hrHVEM was assessed as before by ELISA. The new mAb strongly bound hrHVEM (FIG. 4A). Binding was also assessed by FACS as before. CHO-K1 empty, CHO-K1 hrHVEM, CHO-K1 mrHVEM and CHO-K1 crHVEM cells were incubated for 1 hour on ice with 20 μg/ml of the antibody or hIgG4 isotype control antibody followed by staining with anti-human IgG FC Biotin and anti-Biotin FITC. Expression was assessed by flow cytometry using CytoFLEX instrument and data analysis using FCS Express 6 software. The new mAb strongly bound to rHVEM from all three species (FIG. 4B).

Figure 5A:
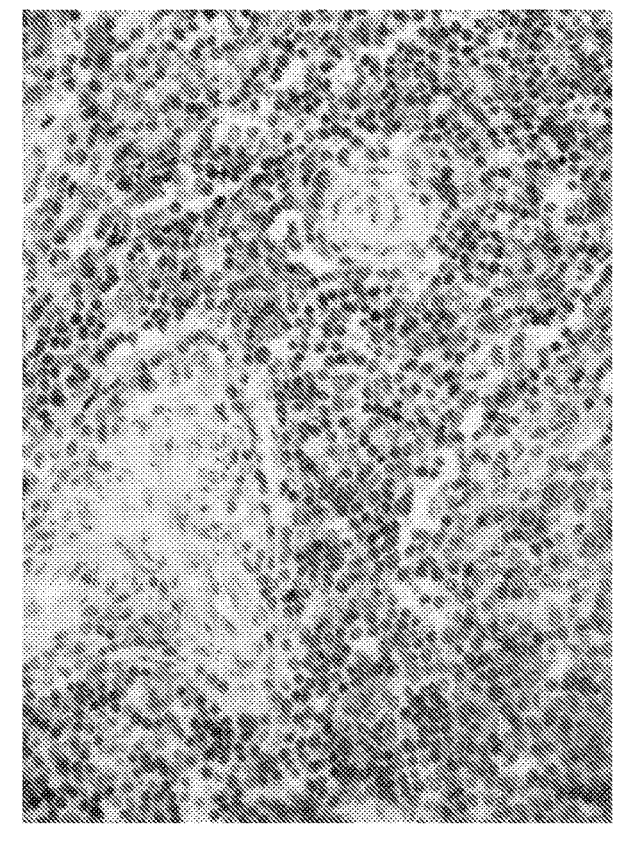
Figure 5A:
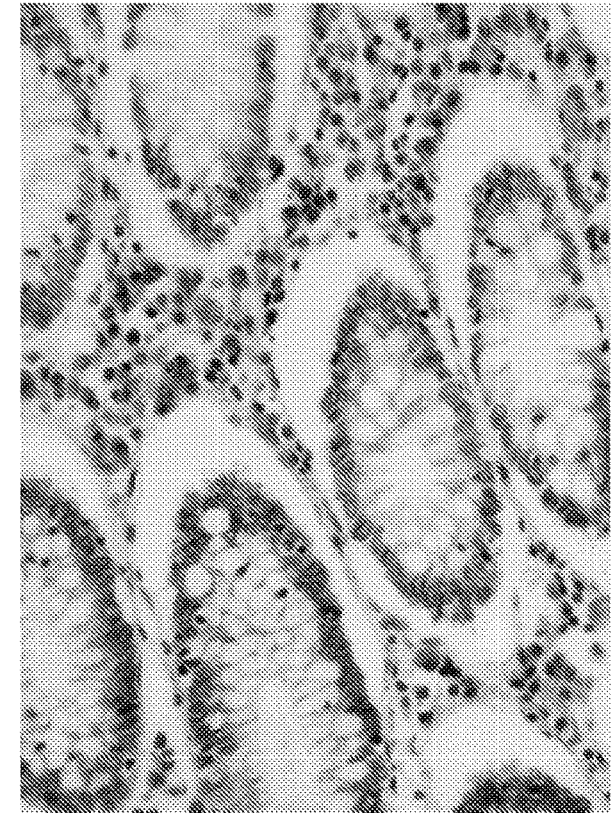
Figures 5B, 5C:
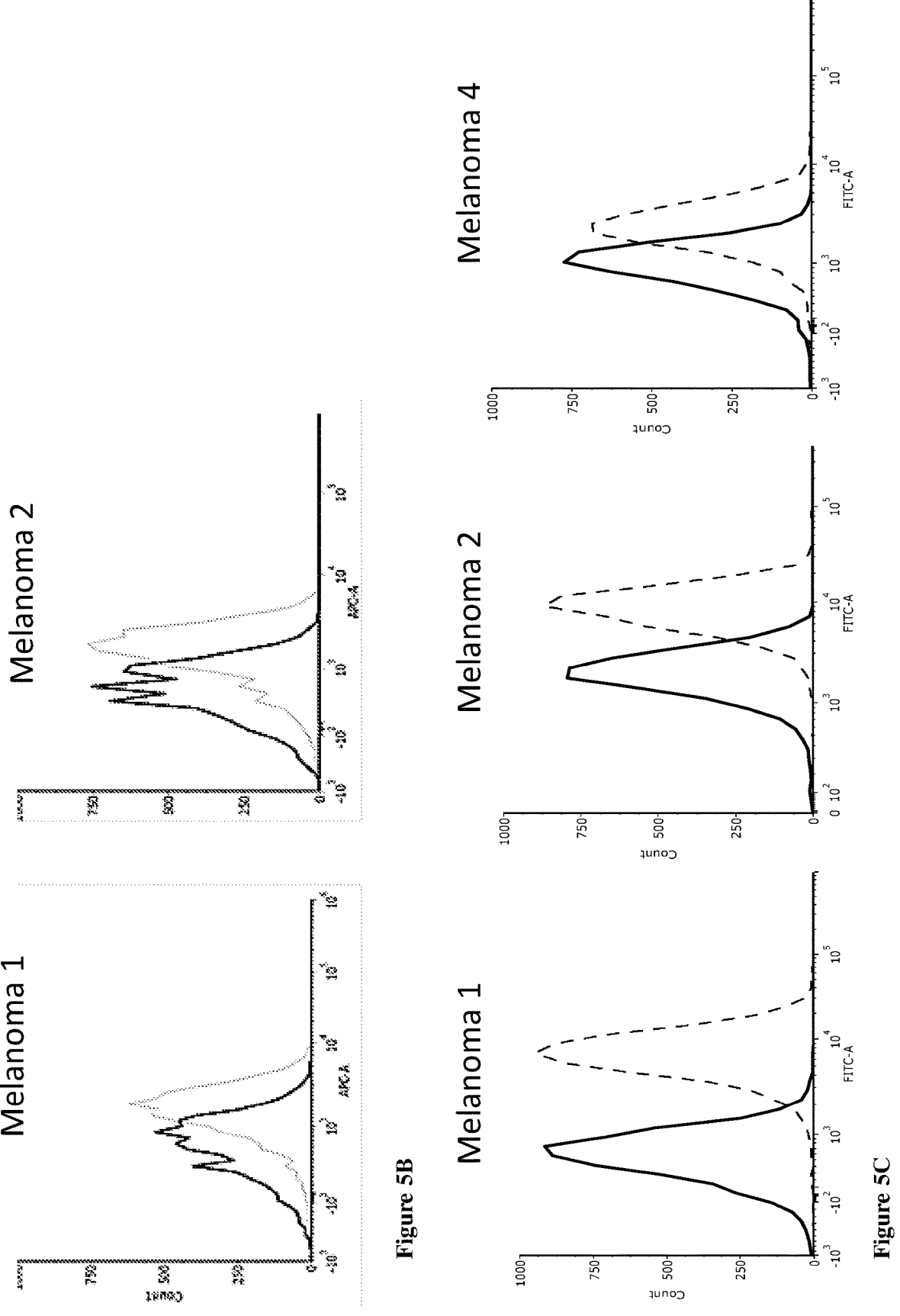
Figure 5D:
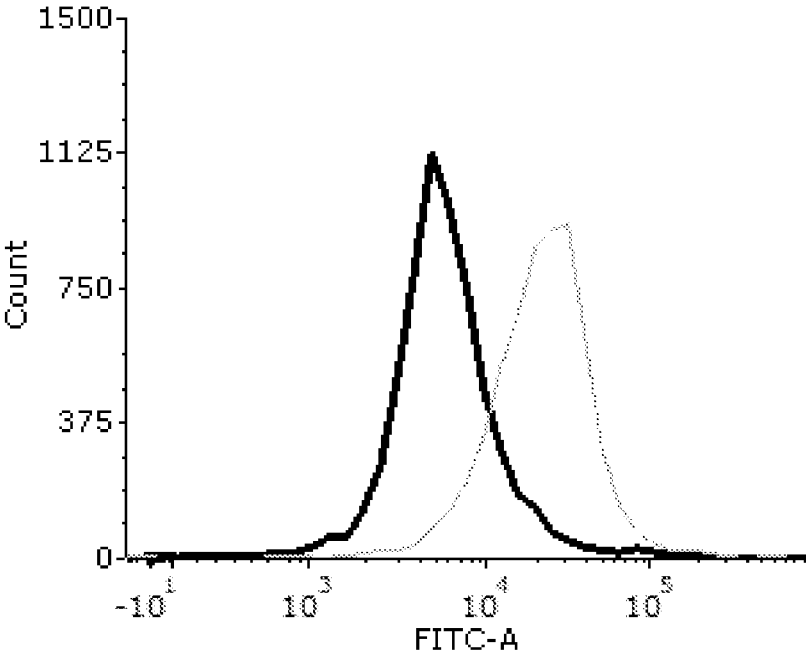
Figure 5E:
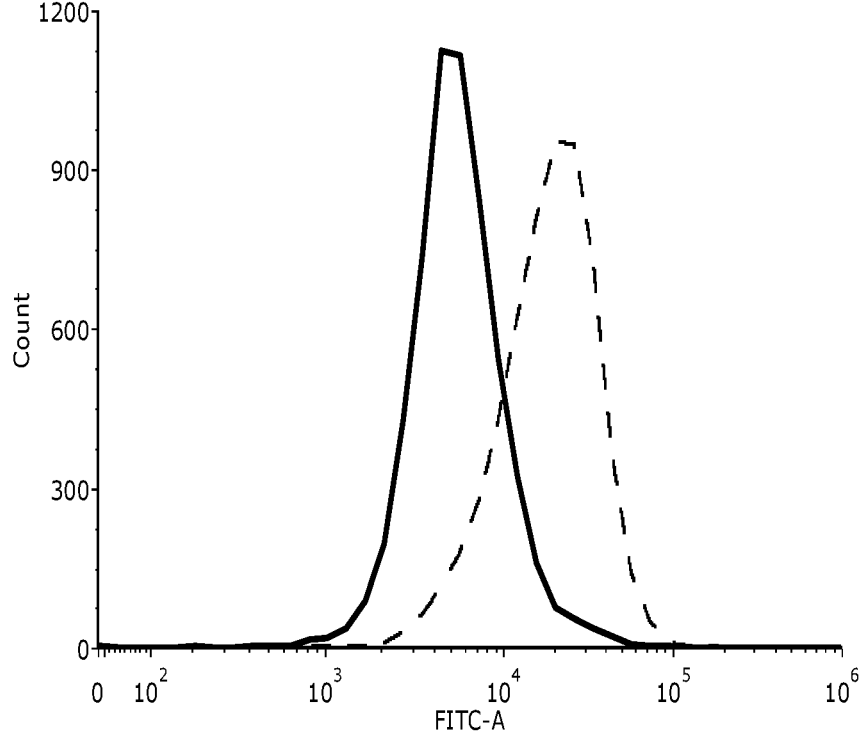

Since the new mAb could bind recombinant human HVEM, its ability to bind to endogenous HVEM on the surface of healthy and cancer cells was tested. First immunohistochemistry was performed with the mAb of the invention on healthy human colon and spleen tissue, where robust staining was observed (FIG. 5A). Next, melanoma cells from three primary patient samples which were known to express HVEM (FIG. 5B) were incubated with 20 μg/ml of the mAb of the invention for 1 hour on ice followed by staining with anti-human IgG FC Biotin and anti-Biotin FITC. Expression was assessed by FACS as before. The new mAb bound to all three tested melanoma samples (FIG. 5C). Binding to a renal cell carcinoma (RCC) patient sample was also tested. Again, a commercially available anti-HVEM antibody (R&D Systems AF356) was used to confirm that the cancer cells expressed HVEM (FIG. 5D). Binding of the new mAb to the surface of these was comparable to the commercial antibody (FIG. 5E). Finally, a tumor microarray was probed with the mAb of the invention (FIG. 5F). 12 different indications were tested, including 1 healthy tissue sample and 5 different tumor samples per indication. Healthy pancreas, lung, breast, bladder and ovary were negative for HVEM; while lymph node, larynx/oral cavity/tongue, brain, kidney, liver and stomach were all positive to varying degrees. Though not all tumors expressed HVEM, at least one tumor sample from each organ type was positive.

Figure 6A:
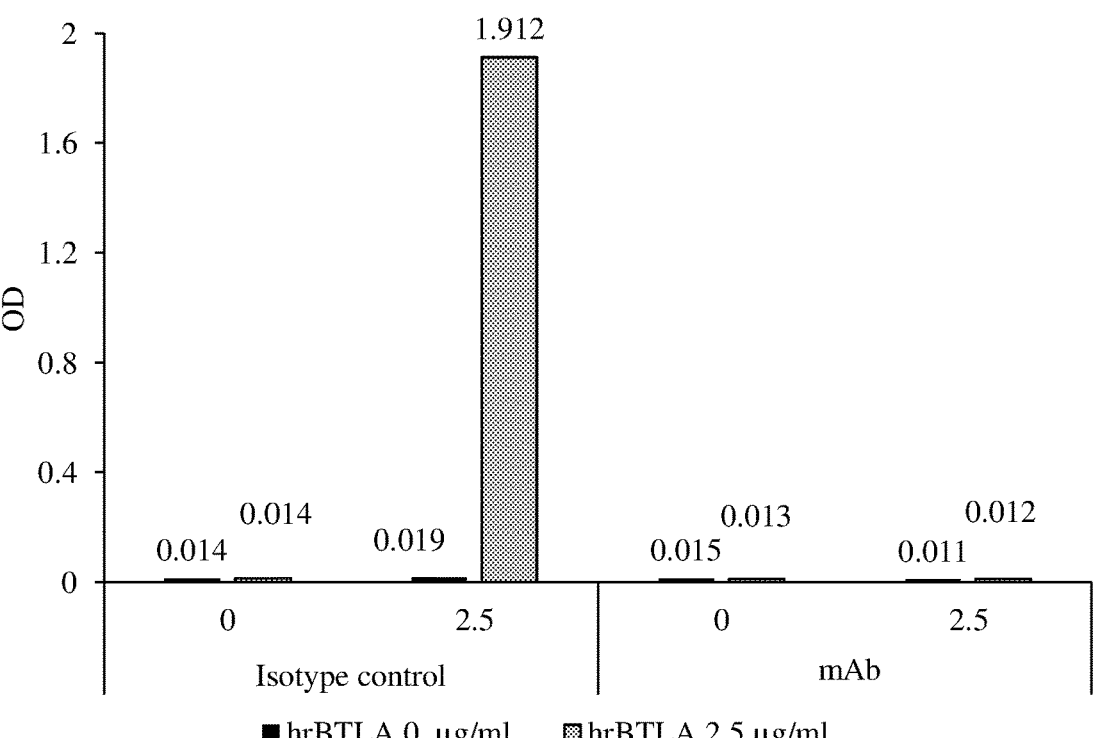
Figure 6B:
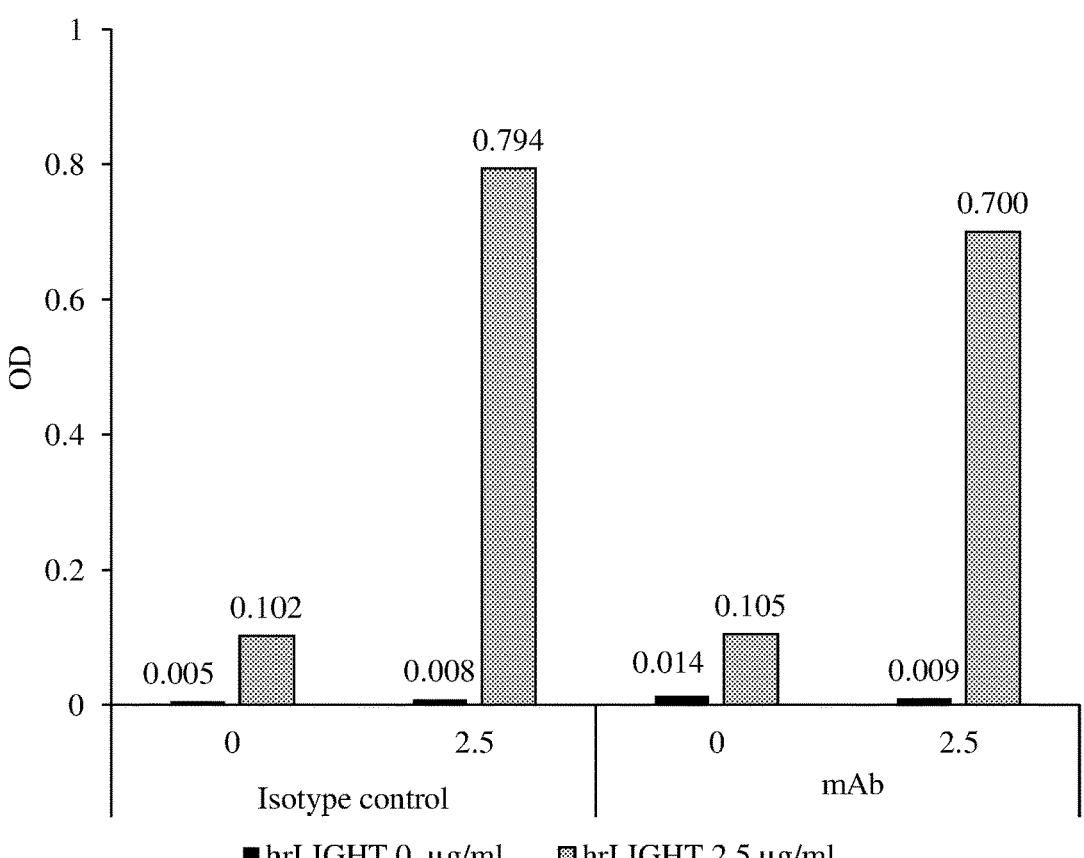
Figure 6C:
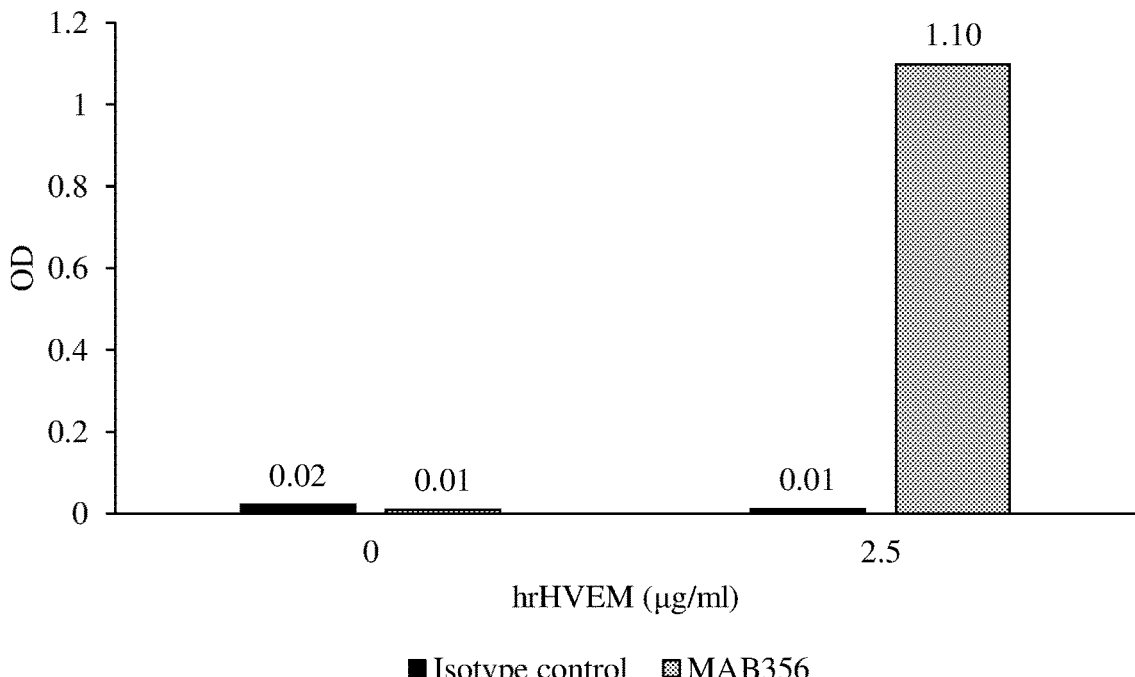
Figure 6D:
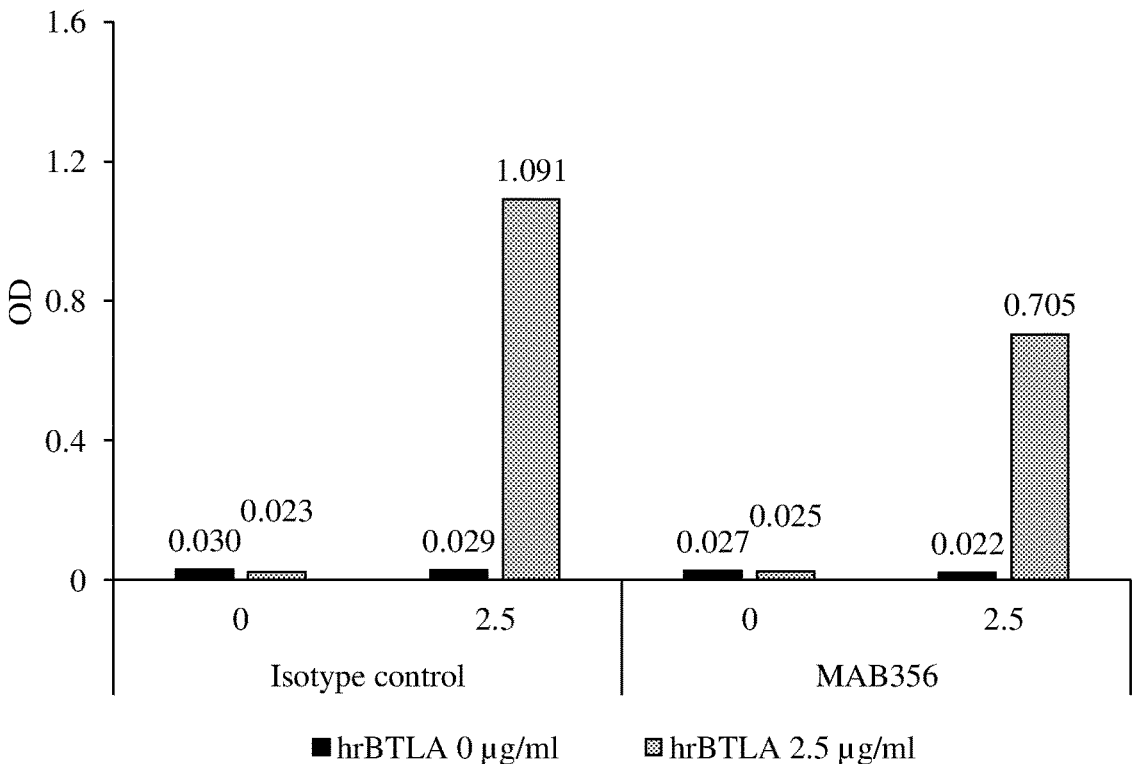

The ability of the full mAb to inhibit BTLA binding to HVEM was also assessed as before. In the presence of the mAb of the invention, BTLA did not bind to HVEM as measured by ELISA (FIG. 6A). Addition of an isotype control IgG served as a positive control in which BTLA strongly bound HVEM. Also as seen for the scFv, the mAb did not inhibit binding of LIGHT to HVEM (FIG. 6B). In contrast, the commercially available anti-HVEM mAB, MAB356, was able to strongly bind hrHVEM as expected (FIG. 6C), but the presence of MAB356 only slightly disrupts HVEM and BTLA interaction, as compared to the addition of mIgG1 isotype control antibody (FIG. 6D). Thus, the mAb of the invention is greatly superior to MAB356 for inhibition of BTLA-HVEM interaction.

Downstream signaling through HVEM was examined next. HVEM activation by ligand binding induces NF-kB signaling. To assess the impact of the mAb of the invention on HVEM signaling, Jurkat T cells expressing hrHVEM and an NF-kB luciferase reporter were pre-incubated with 20 μg/ml of mAb or hIgG4 isotype control for 1 hour on ice. Cells were washed and then co-incubated for 6 hours at 37° C. with CHO-K1-empty, CHO-K1-hrBTLA or no cells at all. Luciferase activity was tested using the Bright-Glo Luciferase Assay System and luminescence was measured 10 minutes after reagent addition, using Spark 10M platereader. Luciferase was induced in Jurkat cells pre-incubated with control antibody only when the CHO cells expressed BTLA (FIG. 7, right). This is to be expected as NF-kB signaling should only be induced by a ligand of HVEM. Interestingly, when pre-incubation was done with the mAb of the invention the very strong induction of luciferase was not seen when coincubation was done with CHO-K1-hrBTLA cells (FIG. 7, left middle bar). This is due to the mAb blocking HVEM-BTLA interaction. However, the level of luciferase after pre-incubation with the mAb is not at baseline either. Rather, the mAb itself induces a mild activation of HVEM and NF-kB signaling (FIG. 7, left). The same level of activation is seen regardless of whether CHO cells are co-incubated at all, which confirms that this activation is caused by the mAb itself and not the cells.

Example 4: The mAb of the Invention Augments T Cell Cytotoxicity Toward Cancer Cells Since the mAb binds HVEM and blocks its binding to BTLA, it was theorized that it would alleviate the inhibitory effect BTLA signaling has on T cells. To test this, adhered melanoma cells were incubated for 1 hour at 37° C. with 20 μg/ml of the mAb of the invention or hIgG4 isotype control antibody. After 1 hour, tumor infiltrating lymphocytes (TILs) were added to the melanoma cells and co-incubated for 24 hours at 37° C. Following the incubation, supernatants were collected from co-culture samples or from TIL only samples as a control for background IFNγ secretion. IFNγ secretion was measured by ELISA using Human IFNγ ELISA Max Deluxe kit. Pre-incubation with the mAb of the invention resulted in a near doubling of the amount of IFNγ secretion in one melanoma cell system, and a still significant, albeit lower, increase in a second system (FIG. 8), indicating that T cell inhibition is indeed relieved by the antibody.

Figure 9A:
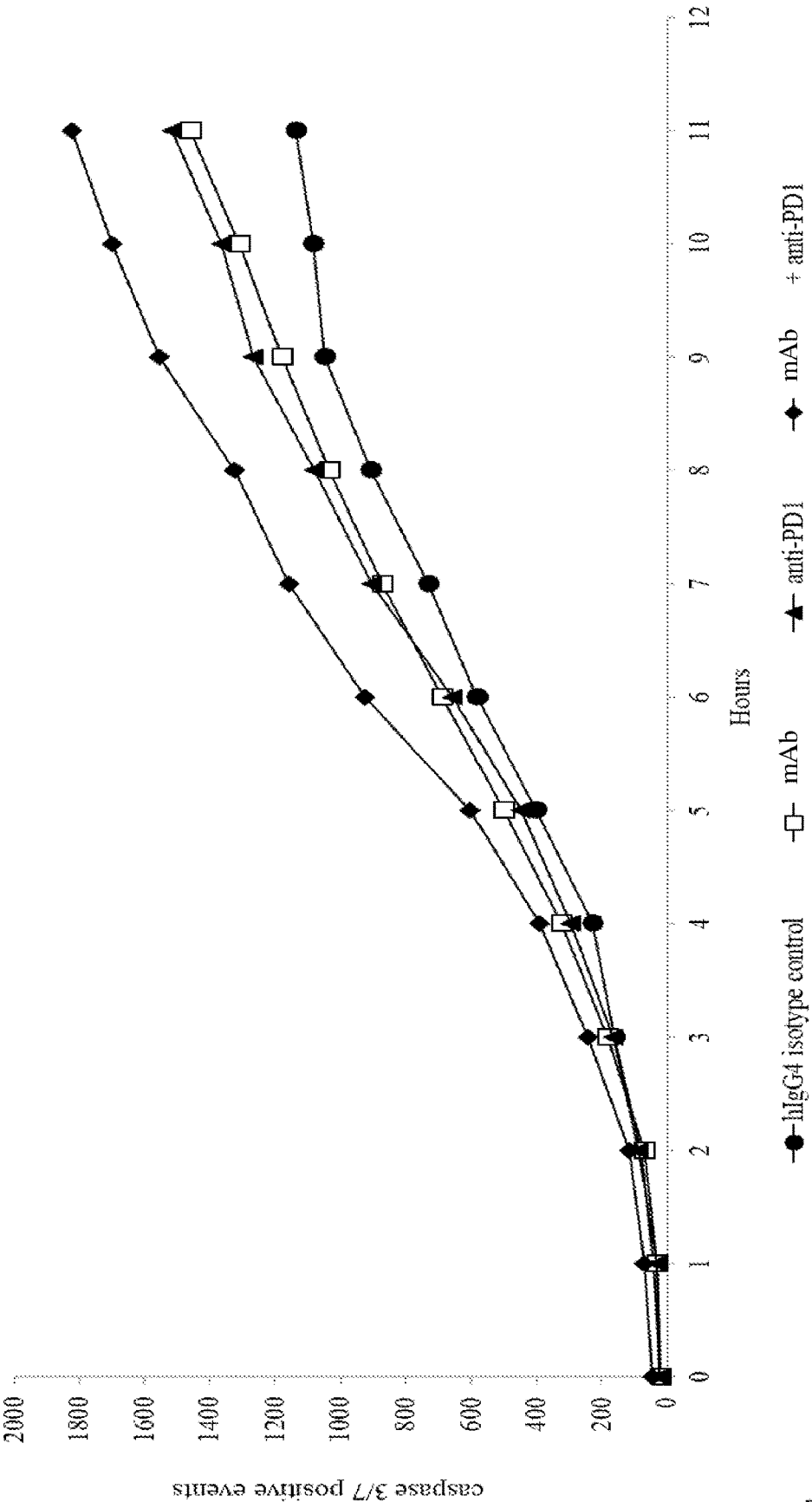
Figure 9B:
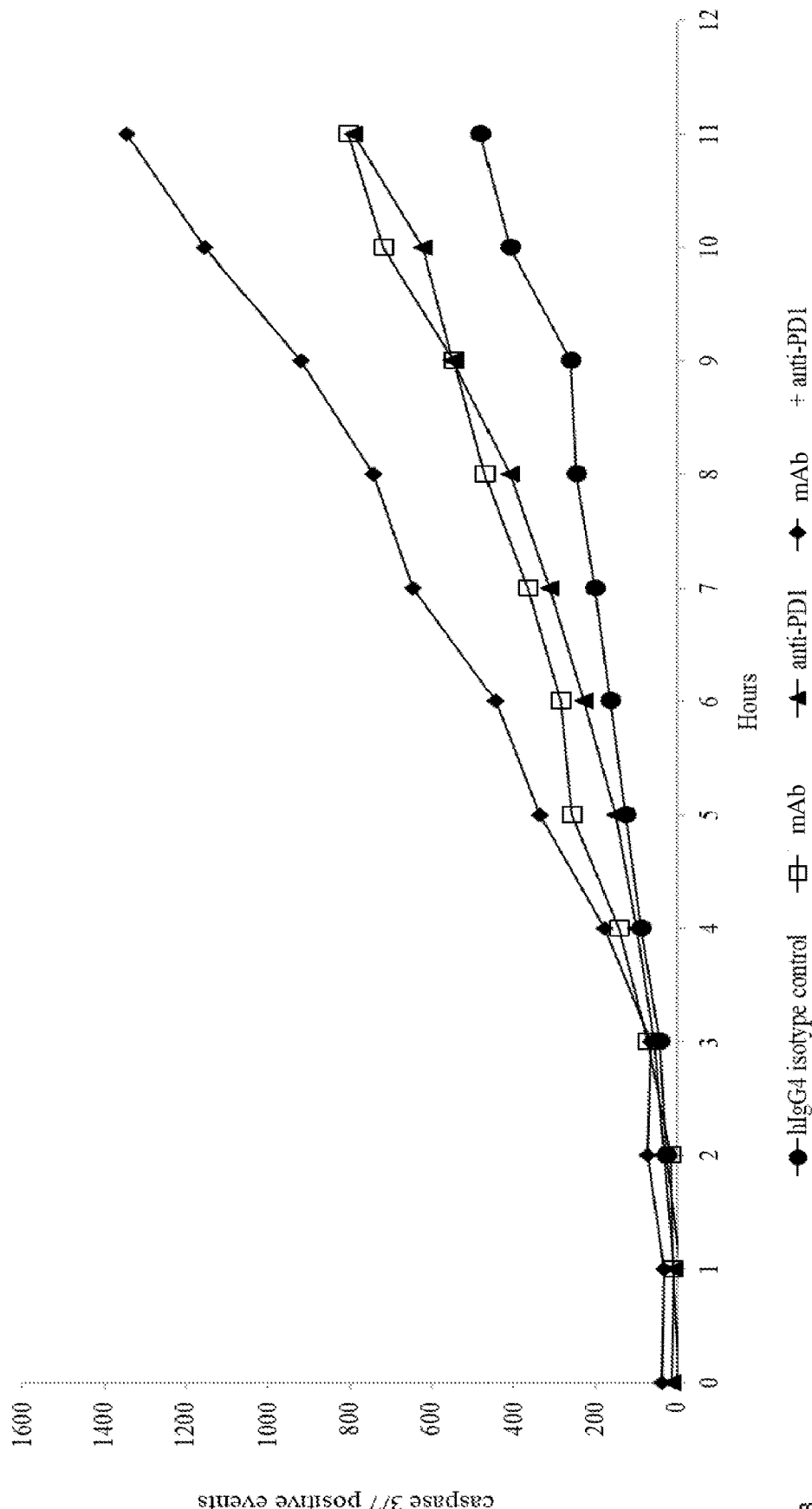
Figure 9C:
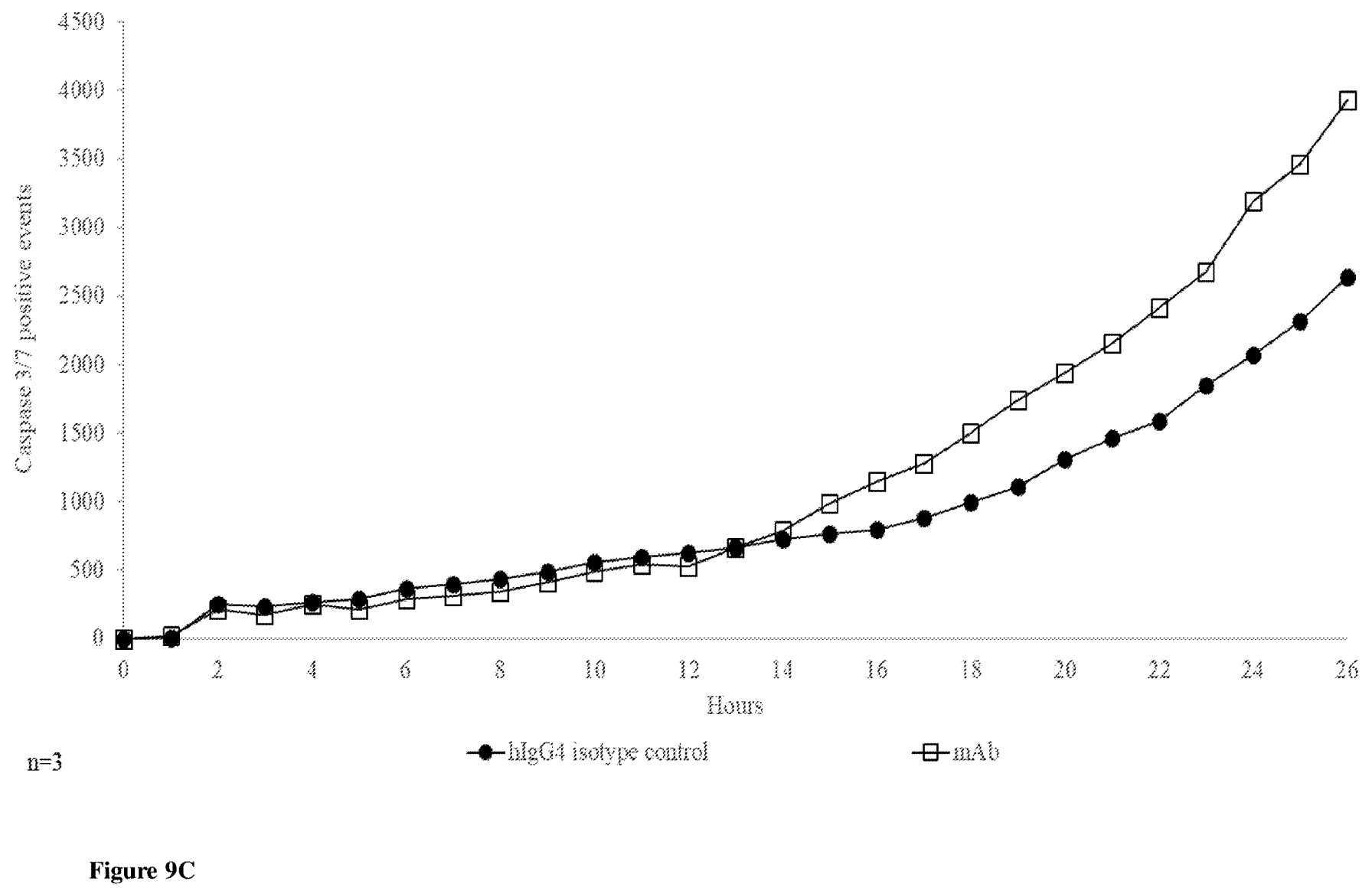
Figure 9D:
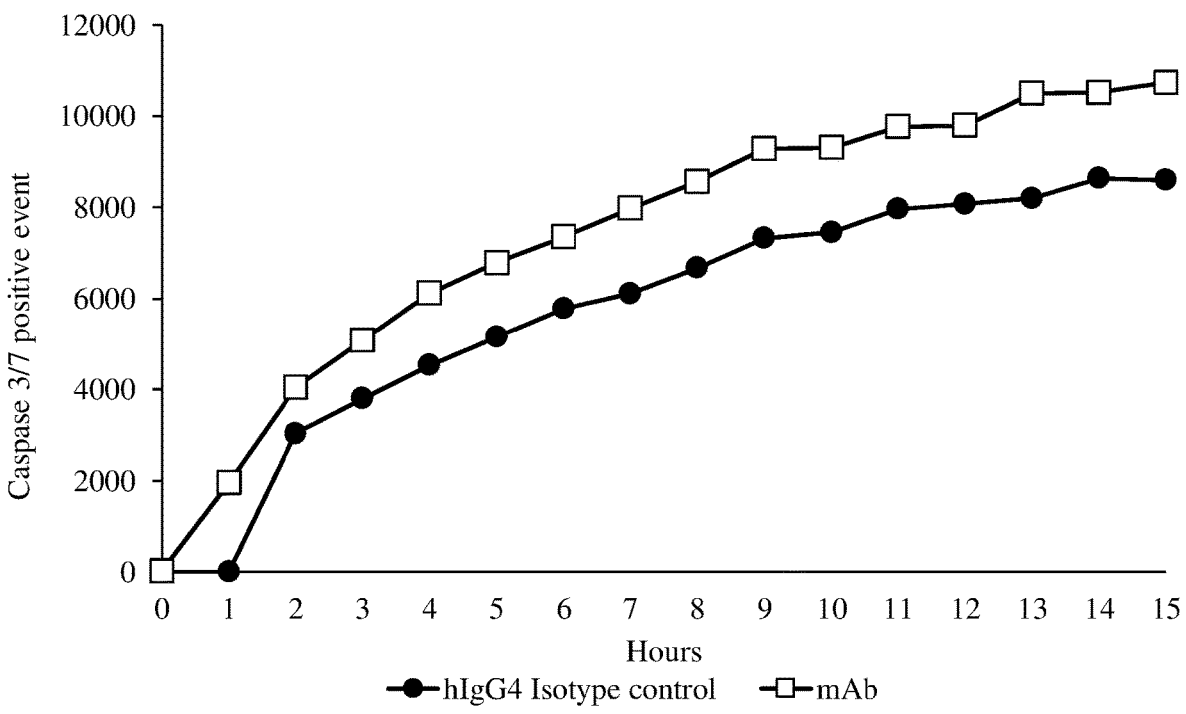

Next, specific killing of primary patient melanoma cells in the presence of autologous TILs was measured. Adhered melanoma cells from two patients were pre-incubated with the mAb of the invention or isotype control. At the same time TILs were pre-incubated with anti-PD-1 antibody or isotype control. Melanoma cells and TILs were then co-incubated in all possible combinations, and specific killing of melanoma cells was measured every hour for 11 hours (FIG. 9A-B). In the first cell system, addition of the mAb of the invention resulted in a nearly 30% increase in total cell killing after 11 hours as compared to cells treated with an isotype control. A similar level of killing was observed with anti-PD1 treatment (33% increase). Combined treatment with both antibodies resulted in a 60% additive increase in overall killing. The combined effect was reinforced by the results obtained with cells from a second patient. Once again, the mAb of the invention and anti-PD1 had similar effects, increasing killing by 67 and 64% respectively. Unexpectedly the combined treatment with both antibodies had a synergistic effect, with the total killing increasing by 180% as compared to the control co-culture. This demonstrates that the two antibodies together can produce a synergistic effect on immune checkpoint inhibition.

Figure 9E:
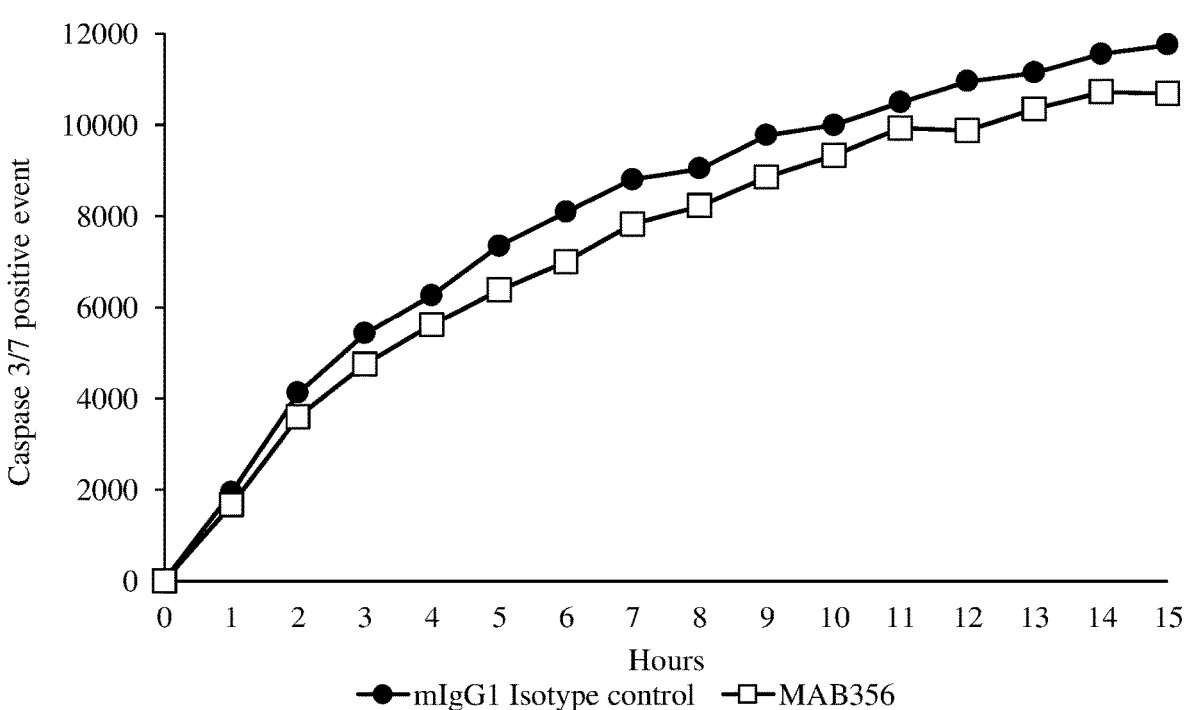

Next, MAB356 was tested in the same system. Melanoma cell killing by TILs was tested as above with melanoma cells from the first patient. Melanoma cells were preincubated with MAB356 or the mAb of the invention or appropriate isotype control and then mixed with autologous TILs. Specific killing of melanoma cells was measured every hour for 15 hours. Addition of the mAb of the invention resulted in a 22% increase in total cell killing after 15 hours as compared to cells treated with hIgG4 isotype control (FIG. 9D), while addition of commercial MAB356 resulted in a 9% decrease in total cell killing as compared to cells treated with mIgG1 isotype control (FIG. 9E). This clearly shows the superiority of the mAb of the invention over MAB356.

A similar experiment was performed with cells from an RCC patient. Cancer cells were adhered overnight, pre-incubated for 1 hour with the mAb of the invention or isotype control before being co-cultured with TILs from the same patient. Cell death in the cancer cells was measured by caspase 3/7 positive events, and after 26 hours the mAb of the invention was found to increase total cell killing by 47% as compared to the isotype control (FIG. 9C).

Example 5: The mAb of the Invention Augments Non-Autologous Immune Cell Cytotoxicity Toward Cancer Cells Having shown that the cytotoxicity of TILs from a cancer patient can be enhanced using the mAb of the invention, the ability to enhance non-autologous immune cells was tested. PBMCs from healthy donors were collected and made to express the alpha and beta chains of a human MART1 TCR. Nuclear RFP stained melanoma cells which express MART1 were adhered overnight, pre-incubated for an hour with the mAb of the invention or isotype control before being co-cultured with the PBMCs. Cell death in the cancer cells was measured by caspase 3/7 positive events, and after 26 hours the mAb of the invention was found to increase total cell killing by 28% as compared to the isotype control (FIG. 10A).

Proinflammatory cytokine secretion from the PBMCs was also measured. Specifically, interferon gamma (IFNγ) secretion was measured in the media from PBMCs cultured with media containing the mAb of the invention or isotype control or cultured with the melanoma cells pre-incubated with the mAb of the invention or isotype control. IFNγ levels were measured 24 hours after culture began. As expected, incubation with melanoma cells greatly increased IFNγ secretion, but incubation with melanoma cells pre-incubated with the mAb of the invention further increased secretion by 32%, as compared to melanoma cells pre-incubated with isotype control (FIG. 10B).

In order to rule out the possibility that the increased cytotoxicity was directly caused by the antibody, and not due to increased T cell killing, the direct cytotoxic effect of the mAb was measured. Nuclear RFP stained adhered melanoma cells were incubated for 1 hour at 37° C. with 20 μg/ml of the mAb of the invention or hIgG4 isotype control antibody. After 1 hour, CellEvent Caspase-3/7 Green Detection Reagent was added to the melanoma cells. Plates were placed in the Incucyte ZOOM system (ESSEN Bioscience, USA) and scanned every hour for 15 hours. No increase in cell death was observed in two different melanoma cells that were incubated with the mAb (FIG. 11), indicating that the antibody itself is not cytotoxic and that the increased cancer killing observed in the last experiment was rather due to increased T cell cytotoxicity.

Example 6: The mAb of the Invention Induces a Basal Mild Activation of TILs

Figure 12A:
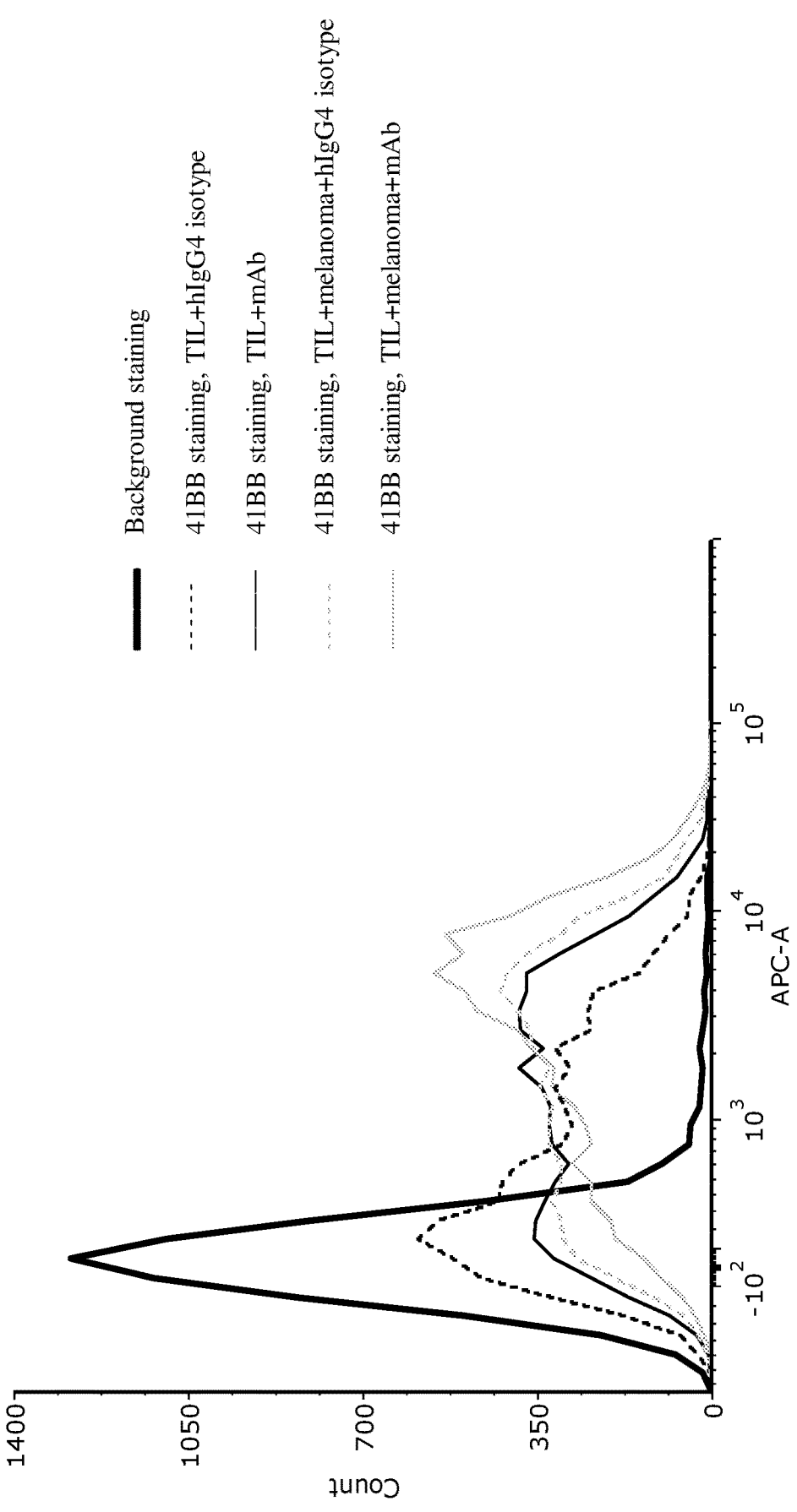

While alleviating BTLA induced suppression in T cells, the mAb of the invention also binds HVEM on the T cells themselves. Since the mAb increases NF-kB induced transcription via HVEM signaling, the direct binding of the mAb may directly increase T cell activation. To test this, TILs were stimulated with the mAb or isotype control, both alone and in the presence of autologous melanoma cells and the activation of the T cells was monitored (FIG. 12A). The percentage of activated T cells was increased in the presence of the mAb both with and without melanoma cells. This indicates that the binding of the antibody to HVEM on the T cells does induce activation on its own. As such, the antibody has at least a double effect, both blocking the immune surveillance escape mechanism of the cancer cells while at the same time directly activating the T cells.

Figure 12B:
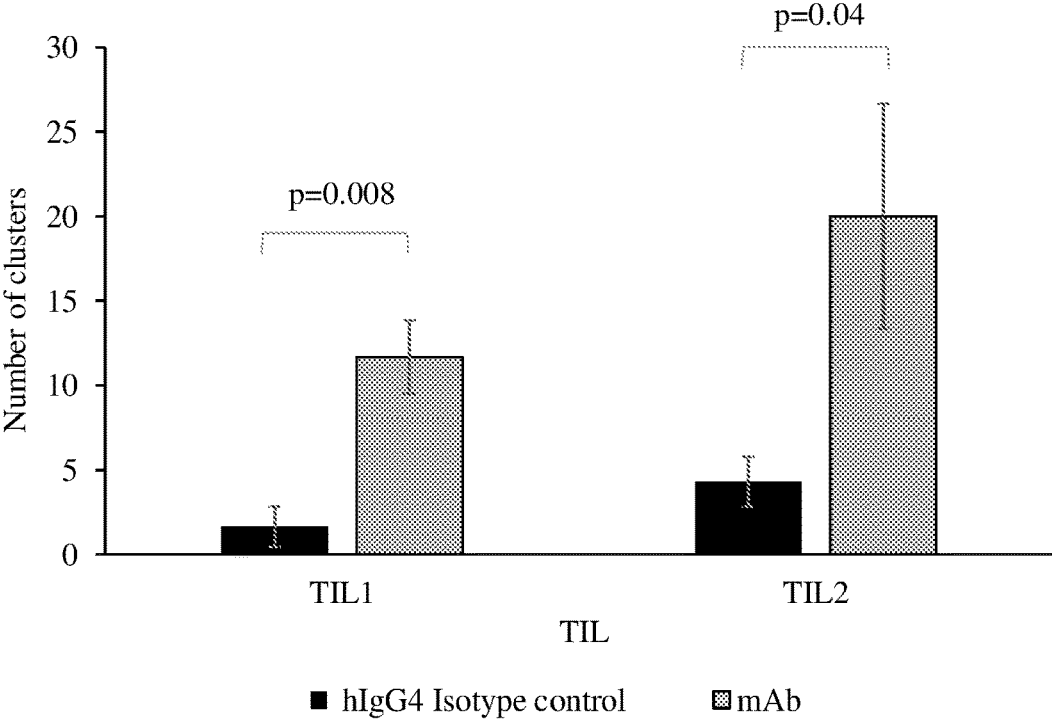
Figure 12C:
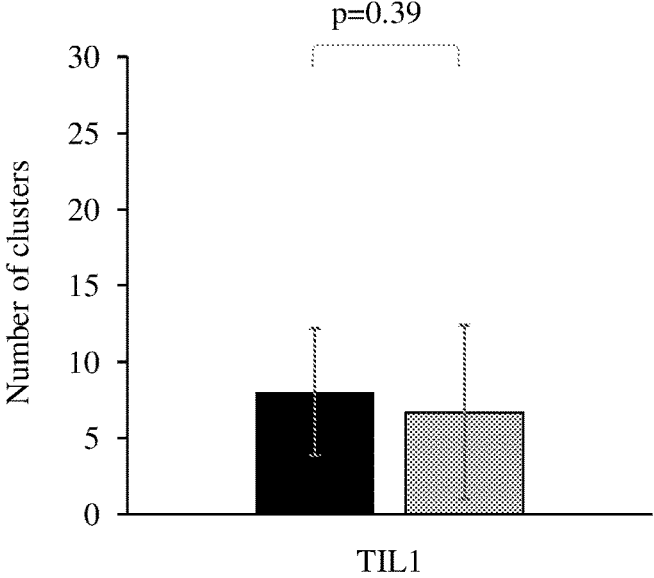

Signaling through HVEM was also tested by measuring T cell clustering. Cell clustering is a hallmark of activated T cells. TILs from two different melanoma patients were incubated with the mAb of the invention or hIgG4 isotype control for 20 hours and then cluster numbers were measured. For both samples tested, the mAb of the invention significantly increased T cell clustering, (FIG. 12B). When MAB356 was tested, no change to T cell clustering was observed as compared to the mIgG1 control (FIG. 12C). This indicates that while binding of the mAb of the invention to HVEM on T cells induces signaling and low-level activation, the commercially available MAB356's binding does not.

Figure 12D:
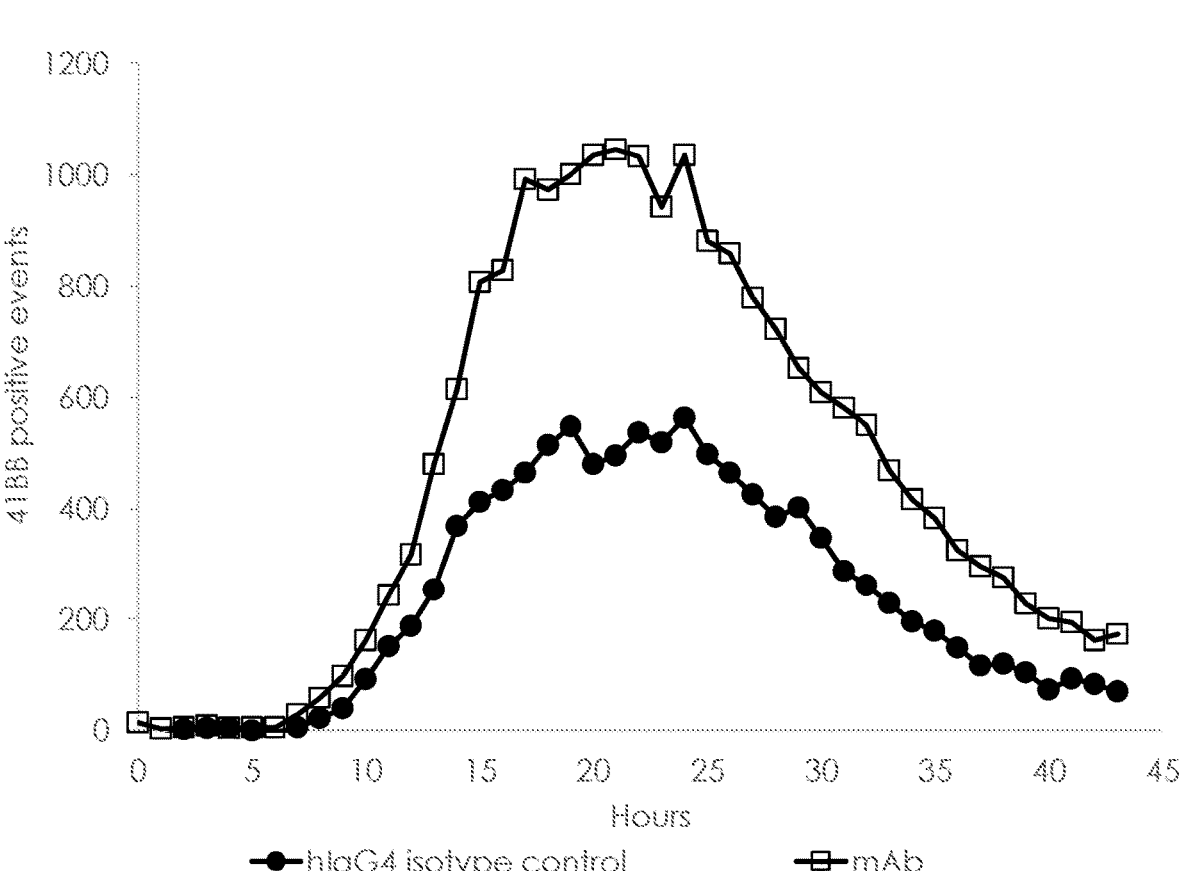

Activation of PBMCs in the presence of melanoma cells was also measured. As before, the PBMCs expressed MART-1 specific TCR so as to target the melanoma cells. For these non-autologous cells as well, the mAb greatly increased activation as measured by 41BB expression on the cells (FIG. 12D).

Cytokine release syndrome is always a concern when an immune checkpoint inhibitor is administered. As shown hereinabove the mAb of the invention is able to induce a mild activation of TILs even in the absence of cancer cells. To further elucidate the extent of this activation a cytokine release assay was performed. Whole blood was collected from 10 healthy donors and the mAb of the invention was tested at concentrations of 0.1, 1, 10 and 100 ug/ml. After 24 hours, samples were measured for expression of five cytokines: IL-6, IL-8, IL-10, IFNγ and TNFα. Two commercially available anti-cancer antibodies Erbitux (EGFR inhibitor) and Lemtrada (anti-CD52) were used as controls. The results of the analysis are summarized in FIG. 13. Unlike Lemtrada that induced a robust cytokine response, the mAb of the invention produced only a mild response that was comparable to Erbitux.

Example 7: In Vivo Cancer Treatment with the mAb of the Invention

Human melanoma cells were implanted subcutaneously in the flank of SCID-NOD mice (day 0). When the tumors reached ~45 mm^3 (day 17), mice were assigned to four treatment groups (3 mice/group) and human autologous TILs were administered intravenously. TILs were again administered on day 34. On day 17, concomitantly with the TIL administration hIL-2 was administered subcutaneously for five consecutive days and then twice a week. On day 18, and then twice a week, mice were administered intravenously hIgG4 isotype control (black circles), mAb of the invention (white squares), anti-PD1 (black triangles) or a combination of both antibodies (black diamonds). Treatment with the mAb of the invention resulted in in tumor growth inhibition (TGI) of 31%, while treatment with anti-PD1 resulted in TGI of only 11%, as compared to treatment with isotype control. The combined treatment had a synergistic effect that resulted in a TGI of 48% (FIG. 14). No adverse side effects were observed in any of the mice. These results demonstrate that the antibody of the invention is effective for in vivo treatment of cancer and that the combined treatment with an anti-PD1 antibody has a synergistic effect that enhances treatment.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:

1. An antibody or antigen binding fragment thereof comprises three heavy chain CDRs (CDR-H) and three light chain CDRs (CDR-L), wherein: CDR-H1 comprises the amino acid sequence set forth in SEQ ID NO: 1 (SYAMS), CDR-H2 comprises the amino acid sequence as set forth in SEQ ID NO: 2 (AISGSGGSTYYADSVKG), CDR-H3 comprises the amino acid sequence as set forth in SEQ ID NO: 3 (APGDYTAYFDY), CDR-L1 comprises the amino acid sequence as set forth in SEQ ID NO: 4 (RASQSVSSYLA), CDR-L2 comprises the amino acid sequence as set forth in SEQ ID NO: 5 (GASSRAT), and CDR-L3 comprises the amino acid sequence as set forth in SEQ ID NO: 6 (QQYGSSPPYT).

2. The antibody or antigen binding fragment thereof of claim 1, comprising a heavy chain comprising the sequence (SEQ ID NO: 7)
QVQLVQSGGGLVQPGGSLRLSCAASGFTFSSYAMSWVRQAPGKGLEWVSA

ISGSGGSTYYADSVKGRFTISRDNSKNTLYLQMNSLRAEDTAVYYCAKAP

GDYTAYFDYWGQGTLVTVSS.

3. The antibody or antigen binding fragment thereof of claim 1, comprising a light chain comprising the sequence (SEQ ID NO: 8)
ELVLTQSPATLSLSPGERATLSCRASQSVSSYLAWYQQKPGQAPRLLIYG

ASSRATGIPDRFSGSGSGTDFTLTISRLEPEDFAVYYCQQYGSSPPYTFG

QGTKVEIK.

4. The antibody or antigen binding fragment thereof of claim 1, comprising a heavy chain comprising the sequence MGWSCIILFLVATATGVHSQVQLVQSGG-GLVQPGGSLRLSCAASGFTFSSYA MSWVRQAPGK-GLEWVSAISGSGGSTYYADSVKGRFTISRDNSKNT-LYLQMN SLRAEDTAVYYCAKAPGDYTAYFDYWGQGTLVTVS-SASTKGPSVFPLAPCS RSTSESTAALGCLVKDYF-PEPVTVSWNSGALTSGVHTFPAVLQSSGLYSLSSV VTVPSSSLGTKTYTCNVDHKPSNTKVDKRVESKY-GPPCPPCPAPEFLGGPSVF LFPPKPKDTLMISRTPE-VTCVVVDVSQEDPEVQFNWYVDGVEVHNAKTKPR EEQFN-STYRVVSVLTVLHQDWLNGKEYKCKVSNKGLPSSIE KTISKAKGQPR EPQVYTLPPSQEEMTKNQVSLT-CLVKGFYPSDIAVEWESNGQPENNYKTTPP VLDSDGSFFLY-SRLTVDKSRWQEGNVFSCSVMHEALHN-HYTQKSLSLSLGK (SEQ ID NO: 9) and a light chain comprising the sequence (SEQ ID NO: 10)
MGWSCIILFLVATATGVHSELVLTQSPATLSLSPGERATLSCRASQSVSS

YLAWYQQKPGQAPRLLIYGASSRATGIPDRFSGSGSGTDFTLTISRLEPE

DFAVYYCQQYGSSPPYTFGQGTKVEIKRTVAAPSVFIFPPSDEQLKSGTA

SVVCLLNNFYPREAKVQWKVDNALQSGNSQESVTEQDSKDSTYSLSSTLT

LSKADYEKHKVYACEVTHQGLSSPVTKSFNRGEC.

5. A pharmaceutical composition comprising an antibody or antigen binding fragment thereof of claim 1 and a pharmaceutically acceptable carrier, excipient or adjuvant.

6. A method of treating a disease or condition characterized by HVEM positive cells in a subject in need thereof, the method comprising administering the pharmaceutical composition of claim 5, thereby treating said disease or condition.

7. The method of claim 6, further comprising administering an anti-PD-1/PD-L1 based immunotherapy.

8. The method of claim 6, further comprising administering adoptive cell therapy, adoptive tumor infiltrating lymphocyte (TIL) therapy, or a chimeric antigen receptor (CAR) expressing immune cell, wherein said CAR targets a non-HVEM protein on a surface of said HVEM expressing cells.

9. The method of claim 6, wherein said disease or condition is an HVEM positive cancer or precancerous lesion.

10. The method of claim 9, wherein said HVEM positive cancer is selected from skin cancer, lung cancer and colon cancer.

11. The method of claim 6, wherein said disease or condition is an infectious disease and wherein said infected cells comprise HVEM expression.

12. A method of determining suitability of a subject to be treated by a method of claim 6, comprising obtaining a disease sample from said subject and determining HVEM levels in said sample, wherein elevated expression of HVEM as compared to a healthy sample or predetermined threshold indicates the subject is suitable for a method of treatment of claim 6.

13. A method of detecting HVEM in a sample, the method comprising contacting said sample with an antibody or antigen binding fragment thereof of claim 1, thereby detecting HVEM.

14. A kit comprising, the pharmaceutical composition of claim 5 and at least one of:
a. an anti-PD-1/PD-L1 based immunotherapy;
b. a label stating the pharmaceutical composition of the invention is for use with an anti-PD-1/PD-L1 based immunotherapy; and
c. a secondary detection molecule.

* * * * *

SEQUENCE LISTING

<160> NUMBER OF SEQ ID NOS: 16

<210> SEQ ID NO 1
<211> LENGTH: 5
<212> TYPE: PRT
<213> ORGANISM: Artificial
<220> FEATURE:
<223> OTHER INFORMATION: Synthetic

<400> SEQUENCE: 1

Ser Tyr Ala Met Ser
1               5

<210> SEQ ID NO 2
<211> LENGTH: 17
<212> TYPE: PRT
<213> ORGANISM: Artificial
<220> FEATURE:
<223> OTHER INFORMATION: Synthetic

<400> SEQUENCE: 2

Ala Ile Ser Gly Ser Gly Gly Ser Thr Tyr Tyr Ala Asp Ser Val Lys
1               5                   10                  15

Gly

<210> SEQ ID NO 3
<211> LENGTH: 11
<212> TYPE: PRT
<213> ORGANISM: Artificial
<220> FEATURE:
<223> OTHER INFORMATION: Synthetic

<400> SEQUENCE: 3

Ala Pro Gly Asp Tyr Thr Ala Tyr Phe Asp Tyr
1               5                   10

<210> SEQ ID NO 4
<211> LENGTH: 11
<212> TYPE: PRT
<213> ORGANISM: Artificial
<220> FEATURE:
<223> OTHER INFORMATION: Synthetic

<400> SEQUENCE: 4

Arg Ala Ser Gln Ser Val Ser Ser Tyr Leu Ala
1               5                   10

<210> SEQ ID NO 5
<211> LENGTH: 7
<212> TYPE: PRT
<213> ORGANISM: Artificial
<220> FEATURE:
<223> OTHER INFORMATION: Synthetic

<400> SEQUENCE: 5

Gly Ala Ser Ser Arg Ala Thr
1               5

<210> SEQ ID NO 6
<211> LENGTH: 10
<212> TYPE: PRT
<213> ORGANISM: Artificial
<220> FEATURE:
<223> OTHER INFORMATION: Synthetic

<400> SEQUENCE: 6

```
Gln Gln Tyr Gly Ser Ser Pro Pro Tyr Thr
1               5                   10

<210> SEQ ID NO 7
<211> LENGTH: 120
<212> TYPE: PRT
<213> ORGANISM: Artificial
<220> FEATURE:
<223> OTHER INFORMATION: Synthetic

<400> SEQUENCE: 7

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Pro Gly Asp Tyr Thr Ala Tyr Phe Asp Tyr Trp Gly Gln
                100                 105                 110

Gly Thr Leu Val Thr Val Ser Ser
            115                 120

<210> SEQ ID NO 8
<211> LENGTH: 108
<212> TYPE: PRT
<213> ORGANISM: Artificial
<220> FEATURE:
<223> OTHER INFORMATION: Synthetic

<400> SEQUENCE: 8

Glu Leu Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Gly Ala Ser Ser Arg Ala Thr Gly Ile Pro Asp Arg Phe Ser Gly
        50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Pro Pro
                85                  90                  95

Tyr Thr Phe Gly Gln Gly Thr Lys Val Glu Ile Lys
            100                 105

<210> SEQ ID NO 9
<211> LENGTH: 466
<212> TYPE: PRT
<213> ORGANISM: Artificial
<220> FEATURE:
<223> OTHER INFORMATION: Synthetic

<400> SEQUENCE: 9

Met Gly Trp Ser Cys Ile Ile Leu Phe Leu Val Ala Thr Ala Thr Gly
```

-continued

```
1               5                   10                  15

Val His Ser Gln Val Gln Leu Val Gln Ser Gly Gly Gly Leu Val Gln
            20                  25                  30

Pro Gly Gly Ser Leu Arg Leu Ser Cys Ala Ala Ser Gly Phe Thr Phe
            35                  40                  45

Ser Ser Tyr Ala Met Ser Trp Val Arg Gln Ala Pro Gly Lys Gly Leu
            50                  55                  60

Glu Trp Val Ser Ala Ile Ser Gly Ser Gly Gly Ser Thr Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Lys Ala Pro Gly Asp Tyr Thr Ala Tyr Phe Asp Tyr
            115                 120                 125

Trp Gly Gln Gly Thr Leu Val Thr Val Ser Ser Ala Ser Thr Lys Gly
            130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
                180                 185                 190

Pro Ala Val Leu Gln Ser Ser Gly Leu Tyr Ser Leu Ser Ser Val Val
                195                 200                 205

Thr Val Pro Ser Ser Ser Leu Gly Thr Lys Thr Tyr Thr Cys Asn Val
                210                 215                 220

Asp His Lys Pro Ser Asn Thr Lys Val Asp Lys Arg Val Glu Ser Lys
225                 230                 235                 240

Tyr Gly Pro Pro Cys Pro Pro Cys Pro Ala Pro Glu Phe Leu Gly Gly
                245                 250                 255

Pro Ser Val Phe Leu Phe Pro Pro Lys Pro Lys Asp Thr Leu Met Ile
                260                 265                 270

Ser Arg Thr Pro Glu Val Thr Cys Val Val Val Asp Val Ser Gln Glu
                275                 280                 285

Asp Pro Glu Val Gln Phe Asn Trp Tyr Val Asp Gly Val Glu Val His
            290                 295                 300

Asn Ala Lys Thr Lys Pro Arg Glu Glu Gln Phe Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Gly Leu Pro Ser Ser Ile Glu
                340                 345                 350

Lys Thr Ile Ser Lys Ala Lys Gly Gln Pro Arg Glu Pro Gln Val Tyr
                355                 360                 365

Thr Leu Pro Pro Ser Gln Glu Glu Met Thr Lys Asn Gln Val Ser Leu
            370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Arg Leu Thr Val Asp
                420                 425                 430
```

```
Lys Ser Arg Trp Gln Glu Gly Asn Val Phe Ser Cys Ser Val Met His
        435             440             445

Glu Ala Leu His Asn His Tyr Thr Gln Lys Ser Leu Ser Leu Ser Leu
    450             455             460

Gly Lys
465

<210> SEQ ID NO 10
<211> LENGTH: 234
<212> TYPE: PRT
<213> ORGANISM: Artificial
<220> FEATURE:
<223> OTHER INFORMATION: Synthetic

<400> SEQUENCE: 10

Met Gly Trp Ser Cys Ile Ile Leu Phe Leu Val Ala Thr Ala Thr Gly
1               5                   10                  15

Val His Ser Glu Leu Val Leu Thr Gln Ser Pro Ala Thr Leu Ser Leu
            20                  25                  30

Ser Pro Gly Glu Arg Ala Thr Leu Ser Cys Arg Ala Ser Gln Ser Val
        35                  40                  45

Ser Ser Tyr Leu Ala Trp Tyr Gln Gln Lys Pro Gly Gln Ala Pro Arg
    50                  55                  60

Leu Leu Ile Tyr Gly Ala Ser Ser Arg Ala Thr Gly Ile Pro Asp Arg
65                  70                  75                  80

Phe Ser Gly Ser Gly Ser Gly Thr Asp Phe Thr Leu Thr Ile Ser Arg
                85                  90                  95

Leu Glu Pro Glu Asp Phe Ala Val Tyr Tyr Cys Gln Gln Tyr Gly Ser
            100                 105                 110

Ser Pro Pro Tyr Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 11
<211> LENGTH: 8
<212> TYPE: PRT
<213> ORGANISM: Artificial
<220> FEATURE:
<223> OTHER INFORMATION: Synthetic
```

-continued

```
<400> SEQUENCE: 11

Gly Phe Thr Phe Ser Ser Tyr Ala
1               5

<210> SEQ ID NO 12
<211> LENGTH: 8
<212> TYPE: PRT
<213> ORGANISM: Artificial
<220> FEATURE:
<223> OTHER INFORMATION: Synthetic

<400> SEQUENCE: 12

Ile Ser Gly Ser Gly Gly Ser Thr
1               5

<210> SEQ ID NO 13
<211> LENGTH: 13
<212> TYPE: PRT
<213> ORGANISM: Artificial
<220> FEATURE:
<223> OTHER INFORMATION: Synthetic

<400> SEQUENCE: 13

Ala Lys Ala Pro Gly Asp Tyr Thr Ala Tyr Phe Asp Tyr
1               5                   10

<210> SEQ ID NO 14
<211> LENGTH: 6
<212> TYPE: PRT
<213> ORGANISM: Artificial
<220> FEATURE:
<223> OTHER INFORMATION: Synthetic

<400> SEQUENCE: 14

Gln Ser Val Ser Ser Tyr
1               5

<210> SEQ ID NO 15
<211> LENGTH: 3
<212> TYPE: PRT
<213> ORGANISM: Artificial
<220> FEATURE:
<223> OTHER INFORMATION: Synthetic

<400> SEQUENCE: 15

Gly Ala Ser
1

<210> SEQ ID NO 16
<211> LENGTH: 10
<212> TYPE: PRT
<213> ORGANISM: Artificial
<220> FEATURE:
<223> OTHER INFORMATION: Synthetic

<400> SEQUENCE: 16

Gln Gln Tyr Gly Ser Ser Pro Pro Tyr Thr
1               5                   10
```